(12) United States Patent
Fukuda et al.

(10) Patent No.: US 9,610,359 B2
(45) Date of Patent: Apr. 4, 2017

(54) METHODS AND COMPOSITIONS RELATED TO ANNEXIN 1-BINDING COMPOUNDS

(75) Inventors: Michiko Fukuda, La Jolla, CA (US); Kazuhiro Sugihara, Higashi-ku (JP); Naohira Kanayama, Higashi-ku (JP)

(73) Assignees: Burnham Institute for Medical Research, La Jolla, CA (US); Hamamatsu University School of Medicine, Shizuoka (JP)

( * ) Notice: Subject to any disclaimer, the term of this patent is extended or adjusted under 35 U.S.C. 154(b) by 0 days.

(21) Appl. No.: 13/515,930

(22) PCT Filed: Dec. 23, 2010

(86) PCT No.: PCT/US2010/062072
§ 371 (c)(1),
(2), (4) Date: Jun. 14, 2012

(87) PCT Pub. No.: WO2011/079304
PCT Pub. Date: Jun. 30, 2011

(65) Prior Publication Data
US 2012/0251453 A1 Oct. 4, 2012

Related U.S. Application Data

(60) Provisional application No. 61/289,833, filed on Dec. 23, 2009.

(51) Int. Cl.
| | | |
|---|---|---|
| *A61K 38/08* | (2006.01) | |
| *A61K 49/00* | (2006.01) | |
| *C07K 7/06* | (2006.01) | |
| *A61P 35/00* | (2006.01) | |
| *A61K 47/48* | (2006.01) | |

(52) U.S. Cl.
CPC .............................. *A61K 47/48276* (2013.01)

(58) Field of Classification Search
CPC .. A61K 38/00; A61K 31/70; A61K 47/48238; A61K 51/1027; A61K 39/0011; A61K 31/00; A61K 51/088; A61K 47/48438; A61K 38/177; A61K 49/0056; A61K 38/08; A61K 51/1018; A61K 49/14; A61K 2300/00; A61K 38/17; A61K 31/198; A61K 38/16; A61K 38/10; A61K 45/06; A61K 39/3955; A61K 39/39558; A61K 39/395; A61K 47/48; C07K 7/06; C07K 2317/732; C07K 2317/24; C07K 2317/92; C12Q 1/68; G01N 33/68; G01N 33/50
USPC ................. 435/320.1, 375; 514/44 A, 44 R; 530/350, 387.3
See application file for complete search history.

(56) References Cited

U.S. PATENT DOCUMENTS

| | | | |
|---|---|---|---|
| 4,016,100 | A | 4/1977 | Suzuki |
| 4,089,801 | A | 5/1978 | Schneider |
| 4,235,871 | A | 11/1980 | Papahadjopoulos |
| 4,418,052 | A | 11/1983 | Wong |
| 4,485,054 | A | 11/1984 | Mezei |
| 4,761,288 | A | 8/1988 | Mezei |
| 4,853,228 | A | 8/1989 | Wallach |
| 5,011,686 | A | 4/1991 | Pang |
| 5,013,497 | A | 5/1991 | Yiournas |
| 5,024,829 | A | 6/1991 | Berger |
| 5,474,848 | A | 12/1995 | Wallach |
| 5,628,936 | A | 5/1997 | Wallach |
| 5,653,996 | A | 8/1997 | Hsu |
| 5,786,322 | A | 7/1998 | Barrett |

(Continued)

FOREIGN PATENT DOCUMENTS

| | | | | |
|---|---|---|---|---|
| WO | WO 00/41711 | * | 7/2000 | ............. A61K 38/04 |
| WO | 0244184 | | 6/2002 | |
| WO | WO2005002516 A2 | * | 1/2005 | |

OTHER PUBLICATIONS

Greiner et al. Synthesis of the protein cutting reagent iron (S)-1-(p-bromoacetamidobenzyl)ethylenediaminetetraacetate and conjugation to cysteine side chains. Bioconjug Chem. Jan.-Feb. 1997;8(1):44-8.*

(Continued)

*Primary Examiner* — Satyanarayana R Gudibande
*Assistant Examiner* — Jia-Hai Lee
(74) *Attorney, Agent, or Firm* — Lewis Kohn & Walker LLP; David M. Kohn; Kari Moyer-Henry

(57) ABSTRACT

Disclosed are conjugates comprising the annexin 1-binding peptide IFLLWQR covalently linked to a therapeutic or detectable agent. Also disclosed are compositions comprising a moiety and a peptide comprising an amino acid sequence that can bind to a carbohydrate receptor on a cell. Also disclosed are isolated nucleic acids comprising a nucleic acid sequence encoding a peptide comprising an amino acid sequence that can bind to a carbohydrate receptor on a cell. Also disclosed are methods comprising administering to a subject a composition comprising a moiety and a peptide comprising an amino acid sequence that can bind to a carbohydrate receptor on a cell. Also disclosed are methods of targeting a tumor cell in a subject comprising administering to the subject a peptide comprising an amino acid sequence that can bind to a carbohydrate receptor on a cell. Also disclosed are methods of targeting a tumor cell in a subject comprising administering to the subject a composition comprising a moiety and a peptide comprising an amino acid sequence that can bind to a carbohydrate receptor on a cell. The disclosed targeting is useful for treatment of, for example, cancer.

13 Claims, 24 Drawing Sheets

(56) References Cited

U.S. PATENT DOCUMENTS

| | | | |
|---|---|---|---|
| 5,897,945 A | 4/1999 | Lieber | |
| 6,530,944 B2 | 3/2003 | West | |
| 6,759,199 B2 | 7/2004 | Mirkin | |
| 7,427,600 B2 * | 9/2008 | Mickle | A61K 31/192 514/1.1 |
| 7,470,658 B2 | 12/2008 | Fukuda | |
| 2003/0017170 A1 * | 1/2003 | Fukuda et al. | 424/185.1 |
| 2004/0009122 A1 | 1/2004 | Klaveness | |
| 2004/0202650 A1 * | 10/2004 | Gribben et al. | 424/131.1 |

OTHER PUBLICATIONS

Akaji et al. Total Synthesis of Human Insulin by Regioselective Disulfide Formation Using the Silyl Chloride-Sulfoxide Method. J. Am. Chem. Soc. 1993,115. 11384-11392.*
Michael Brinkley. A Brief Survey of Methods for Preparing Protein Conjugates with Dyes, Haptens, and Cross-Linking Reagents. Bioconjugate Chem. 1992, 3, 2-13.*
Lumiprobe Inc. Protocol: Maleimide labeling of proteins and other thiolated biomolecules. Lumiprobe Inc. 2008.*
Akaji et al. Total Synthesis of Human Insulin by Regioselective Disulfide Formation Using the Silyl Chloride-Sulfoxide Method. J. Am. Chem. Soc. 1993,115. 1 1384-1 1392.*
Liang et al. Synthesis of doxorubicin-peptide conjugate with multidrug resistant tumor cell killing activity. Bioorg Med Chem Lett. Nov. 15, 2005;15(22):5071-5.*
Hatakeyama et al. Targeted drug delivery to tumor vasculature by a carbohydrate mimetic peptide. Proc Natl Acad Sci U S A. Dec. 6, 2011;108(49):19587-92.*
Satio et al. Drug delivery strategy utilizing conjugation via reversible disulfide linkages: role and site of cellular reducing activities. Adv Drug Deliv Rev. Feb. 10, 2003;55(2):199-215.*
Prasad et al. Delivering multiple anticancer peptides as a single prodrug using lysyl-lysine as a facile linker J. Pept. Sci. 2007; 13: 458-467.*
Fricker LD. Neuropeptide-processing enzymes: applications for drug discovery. AAPS J. Oct. 5, 2005;7(2):E449-55.*
Allam, et al., "Cholera toxin triggers apoptosis in human lung cancer cell lines", Cancer Res., 57:2615-8 (1997).
Arap, et al., "Cancer treatment by targeted drug delivery to tumor vasculature in a mouse model", Science, 279:377-80 (1998).
Bailey, et al., "Boron-Containing Antibacterial Agents: Effects on Growth and Morphology of Bacteria Under Various Culture Conditions", Antimicrob Agents Chemother, 17: 549-53 (1980).
Bangham, et al., "Diffusion of univalent ions across the lamellae of swollen phospholipids", J Mol. Biol. 13:238-52 (1965).
Barenholz, et al., "A new method for preparation of phospholipid vesicles (liposomes)—French press", FEBS Lett. 99:210-4 (1979).
Batzri, et al., "Single bilayer liposomes prepared without sonication", Biochim et Biophys Acta 298:1015-9 (1973).
Bellone, et al., "Vascular targeting, chemotherapy and active immunotherapy: teaming up to attack cancer", Trends Immunol., 29:235-41 (2008).
Borgstrom, et al., "Importance of VEGF for breast cancer angiogenesis in vivo: implications from intravital microscopy of combination treatments with an anti-VEGF neutralizing monoclonal antibody and doxorubicin", Anticancer Res. 19:4203-14 (1999).
Callow, et al., "Thermodynamic modeling and cryomicroscopy of cell-size, unilamellar, and paucilamellar liposomes", Cryobiology, 22(3):251-67 (1985).
Chan, et al. "Prospective randomized trial of docetaxel versus doxorubicin in patients with metastatic breast cancer.",, J. Clin. Oncol. 17:2341-54 (1999).
Clarke, et al., "Gene expression profiling of human colon cancer cells following inhibition of signal transduction by 17-allylamino-17-demethoxygeldanamycin, an inhibitor of the hsp90 molecular chaperone", Oncogene, 19: 4125-33 (2000).
Crown, "The platinum agents: a role in breast cancer treatment", Seminars Oncol. 28:28-37 (2001).
Davis, et al., "Isolation of angiopoietin-1, a ligand for the TIE2 receptor, by secretion-trap expression cloning", Cell, 87:1161-9 (1996).
De Maria, et al., "Requirement for GD3 ganglioside in CD95- and ceramide-induced apoptosis", Science, 277:1652-5 (1997).
De Roos, et al., "Myocardial infarct sizing and assessment of reperfusion by magnetic resonance imaging: a review", Int. J. Card. Imaging., 7:133 (1991).
del Rio, et al., "APAP, a sequence-pattern recognition approach identifies substance P as a potential apoptotic peptide", FEBS Lett., 494:213-9 (2001).
Deamer, et al., "Large volume liposomes by an ether vaporization method", Biochim Biophys Acta., 443:629-34 (1976).
Donate, et al., "Pharmacology of the novel antiangiogenic peptide ATN-161 (Ac-PHSCN-NH2): observation of a U-shaped dose-response curve in several preclinical models of angiogenesis and tumor growth", Clin Cancer Res., 14:2137-44 (2008).
Duckert, et al., "Prediction of proprotein convertase cleavage sites", Protein Eng Des Sel., 17(1):107-12 (2004).
Eiseman, et al., "Pharmacokinetics and pharmacodynamics of 17-demethoxy 17-[[(2-dimethylamino)ethyl]amino]geldanamycin (17DMAG, NSC 707545) in C.B-17 SCID mice bearing MDA-MB-231 human breast cancer xenografts", Cancer Chemother Pharmacol; 55:21-32 (2005).
Ellerby, et al., "Anti-cancer activity of targeted pro-apoptotic peptides", Nat Med., 5:1032-8 (1999).
Fisher, et al., "Tamoxifen for prevention of breast cancer: report of the National Surgical Adjuvant Breast and Bowel Project P-1 Study", J. Natl. Cancer Instit. 90:1371-88 (1998).
Fitzpatrick and Garnett, "Design, synthesis and in vitro testing of methotrexate carrier conjugates linked via oligopeptide spacers", Anticancer Drug Des. 10:1-9 (1995).
Folkman, "Addressing tumor blood vessels", Nat Biotechnol., 15:510 (1997).
Folkman and Shing, "Angiogenesis", J. Biol. Chem. 267:10931-4 (1992).
Fukuda, et al., "A peptide mimic of E-selectin ligand inhibits sialyl Lewis X-dependent lung colonization of tumor cells", Cancer Res., 60:450-6 (2000).
Fukuda, "Screening of peptide-displaying phage libraries to identify short peptides mimicking carbohydrates", Methods Enzymol., 416:51-60 (2006).
Fukuda, et al., "202 Targeted Drug delivery to tumor vasculature by a Carbohydrate-mimicry peptide", NCI Translates—NCI translational, Science meeting., p. 209, (2009).
Groziak, "Boron Therapeutics on the horizon", Am J Ther., 8:321-8 (2001).
Hagedorn and Bikfalvi, "Target molecules for anti-angiogenic therapy: from basic research to clinical trials", Crit. Rev. Oncol. Hematol. 34:89-110 (2000).
Hakomori, "Glycosylation defining cancer malignancy: new wine in an old bottle", PNAS, 99:10231-3 (2002).
Hannon, et al., "Aberrant inflammation and resistance to glucocorticoids in annexin 1-/- mouse",. Faseb J., 17:253-5 (2003).
Hatakeyama, et al., "Identification of mRNA splicing factors as the endothelial receptor for carbohydrate-dependent lung colonization of cancer cells", PNAS, 106:3095-3100 (2009a).
Hatakeyama, et al., "Cancer targeting chemotherapy by annexin A1 binding IF7 peptide conjugated with geldanamycin", J Urol., Lippincott Williams and Wilkins, Baltimore, MD, 181(4):71-72 (2009b).
Hatakeyama, et al., "Highly efficient drug delivery targeted to malignant tumors by carbohydrate mimicry peptide IF7", Glycobiology, Annual zmeeting opf the Soc for Glycobiology, San Diego, Ca Nov. 12-15, 19(11):1326 (2009c).
Homandberg, et al., "Heparin-binding fragments of fibronectin are potent inhibitors of endothelial cell growth", Am. J. Path., 120:327-32 (1985).
Homandberg, et al., "Heparin-binding fragments of fibronectin are potent inhibitors of endothelial cell growth: structure-function correlations",Biochim. Biophys. Acta., 874:61-71 (1986).

(56) References Cited

OTHER PUBLICATIONS

Izumoto, et al., "Phase II clinical trial of Wilms tumor 1 peptide vaccination for patients with recurrent glioblastoma multiforme", J Neurosurg, 108: 963-71 (2008).
Kim, et al., "Preparation of multivesicular liposomes", Biochim Biophys Acta., 728:339-48 (1983).
Kirsch, et al., "Anti-angiogenic treatment strategies for malignant brain tumors", J. Neurooncol., 50:149-63 (2000).
Koehler and Hess, "A New, specific and reversible bifunctional alkylborinic acid inhibitor of acetylcholinesterase", Biochem., 13:5345-50 (1974).
Kreitman and Pastan,"Recombinant toxins containing human granulocyte-macrophage colony-stimulating factor and either pseudomonas exotoxin or diphtheria toxin kill gastrointestinal cancer and leukemia cells", Blood, 90:252-9 (1997).
Landon, et al., "Is phage display technology on target for developing peptide-based cancer drugs", Curr Drug Discov Technol., 1:113-32 (2004).
Lehr, et al. "Dorsalskinfold chamber technique for intravital microscopy in nude mice", Am J Pathol., 143:1055-62 (1993).
Mandler, et al., "Immunoconjugates of geldanamycin and anti-HER2 monoclonal antibodies: antiproliferative activity on human breast carcinoma cell lines", J Natl Cancer Inst., 92: 1573-81, (2000).
Martin, et al., "Cancer gene therapy by thyroid hormone-mediated expression of toxin genes", Cancer Res. 60:3218-24 (2000).
Meyer-Losic, et al., "DTS-108, A Novel Peptidic Prodrug of SN38: In vivo Efficacy and Toxicokinetic Studies", Clin Cancer Res., 14: 2145-53 (2008).
Mitsiades, et al., "Antimyeloma activity of heat shock protein-90 inhibition", Blood, 107: 1092-100 (2006).
Murphy, et al., "Nanoparticle-mediated drug delivery to tumor vasculature suppresses metastasis", PNAS, 105:9343-8 (2008).
Nakamori, et al., "Increased expression of sialyi Lewisx antigen correlates with poor survival in patients with colorectal carcinoma: clinicopathological and immunohistochemical study", Cancer Res., 53:3632-7 (1993).
Neri and Bicknell, "Tumour vascular targeting", Nat Rev Cancer, 5: 436-46 (2005).
Oh, et al., "Subtractive proteomic mapping of the endothelial surface in lung and solid tumours for tissue-specific therapy", Nature, 429:629-635 (2004).
Oh, et al., "Live dynamic imaging of caveolae pumping targeted antibody rapidly and specifically across endothelium in the lung", Nat Biotechnol., 25: 327-37 (2007).
Oku, et al., "Anti-neovascular therapy using novel peptides homing to angiogenic vessels", Oncogene, 21:2662-9 (2002).
OReilly, et al., "Angiostatin: a novel angiogenesis inhibitor that mediates the suppression of metastases by a Lewis lung carcinoma", Cell, 79:315-28 (1994).
OReilly, et al., "Endostatin: an endogenous inhibitor of angiogenesis and tumor growth", Cell, 88:277-85 (1997).
OReilly, et al., "Antiangiogenic activity of the cleaved conformation of the serpin antithrombin", Science, 285:1926-8 (1999).
Osborne and Coronado-Heinsohn, "Targeting the epidermal growth factor receptor in breast cancer cell lines with a recombinant ligand fusion toxin (DAB389EGF).", Cancer J. Sci. Am. 2:175-80 (1996).
Otvos, "Peptide-based drug design: here and now", Methods Mol Biol 494:1-8 (2008).
Panaretou, et al., "Activation of the ATPase activity of hsp90 by the stress-regulated cochaperone ahal", Mol Cell, 10: 1307-18 (2002).

Papahadjopoulos, et al., "Surface properties of acidic phospholipids: interaction of monolayers and hydrated liquid crystals with uni- and bi-valent metal ions", Biochim Biophys Acta., 163(2):240-54 (1968).
Paridaens, et al., "Paclitaxel versus doxorubicin as first-line single-agent chemotherapy for metastatic breast cancer: a European Organization for Research and Treatment of Cancer Randomized Study with cross-over", J. Clin. Oncol., 18:724-33 (2000).
Powers, et al., "Indium-111 platelet scintigraphy in cerebrovascular disease", Neurology., 32:938-43 (1982).
Ruoslahti and Rajotte, "An address system in the vasculature of normal tissues andTumors", Annu Rev Immunol., 18: 813-27 (2000).
Slavin, et al., "Fibroblast growth factors: at the heart of angiogenesis", Cell Biol., 19:431-44 (1995).
Schnitzer, "Caveolae: from basic trafficking mechanisms to targeting transcytosis for tissue-specific drug and gene delivery in vivo", Adv Drug Deliv Rev., 49:265-80 (2001).
Schnitzer, et al., "Endothelial caveolae have the molecular transport machinery for vesicle budding, docking, and fusion including VAMP, NSF, SNAP, annexins, and GTPases", J Biol Chem., 270: 14399-404 (1995).
Scott, et al., "A family of concanavalin A-binding peptides from a hexapeptide epitope library", PNAS, 89:5398-5402 (1992).
Simpelkamp and Jones, "Borinic acid inhibitors as probes of the factors involved in binding at the active sites of subtilisin Carlsberg and a-chymotrypsin", Bioorganic Med Chem Lttrs, 2(11):1391-4 (1992).
Solit, et al., "Inhibition of heat shock protein 90 function down-regulates Akt kinase and sensitizes tumors to Taxol", Cancer Res., 63: 2139-44 (2003).
Solit, et al., "17-Allylamino-17-demethoxygeldanamycin induces the degradation of androgen receptor and HER-2/neu and inhibits the growth of prostate cancer xenografts", Clin Cancer Res., 8:986-93 (2002).
Suri, et al., "Requisite role of angiopoietin-1, a ligand for the TIE2 receptor, during embryonic angiogenesis", Cell, 87:1171-80 (1996).
Suzuki-Anekoji, et al., "Targeted drug delivery to tumor vasculature by the IF7 peptide in mouse gliomamodel", Joint meeting, Soc. for Glycobiology & Am. Soc for Matrix Biol.,Conference Abstracts (2012).
Taki, et al., "A new approach for drug discovery from glycobiology and phage-displayed peptide library technology", Biochim Biophys Acta., 1780:497-503 (2008).
Thakur, et al., "Indium-LLL labeled platelets: studies on preparation and evaluation of in vitro and in vivo functions", Thromb Res., 9:345-57 (1976).
Vasilevskaya, et al., "Geldanamycin and its 17-allylamino-17-demethoxy analogue antagonize the action of Cisplatin in human colon adenocarcinoma cells: differential caspase activation as a basis for interaction", Cancer Res., 63: 3241-6 (2003).
Weinand, et al., "Design, Synthesis and Biological Evaluation of Selective Boron-containing Thrombin Inhibitors", Bioorg Med Chem., 7:1295-1307 (1999).
White, et al., "Antibody-targeted immunotherapy for treatment of malignancy", Annu. Rev. Med., 52:125-45 (2001).
Yamamoto, "Molecular Design and Synthesis of B-10 Carriers for Neutron Capture Therapy", Pure Appl. Chem., 63:423-6 (1991).
Zhang, et al., "Sialyi Lewis X-dependent lung colonization of B16 melanoma cells through a selectin-like endothelial receptor distinct from E- or P-selectin", Cancer Res., 62:4194-8 (2002).

\* cited by examiner

SEQUENCE LISTING

```
<160> NUMBER OF SEQ ID NOS: 31

<210> SEQ ID NO 1
<211> LENGTH: 7
<212> TYPE: PRT
<213> ORGANISM: Artificial sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 1

Ile Glu Leu Leu Gln Ala Arg
1               5

<210> SEQ ID NO 2
<211> LENGTH: 7
<212> TYPE: PRT
<213> ORGANISM: Artificial sequence
<220> FEATURE:
<223> OTHER INFORMATION: chemically synthesized; annexin-1 binding
```

```
           compound
<220> FEATURE:
<221> NAME/KEY: PEPTIDE
<222> LOCATION: (1)..(7)

<400> SEQUENCE: 2

Ile Phe Leu Leu Trp Gln Arg
1               5

<210> SEQ ID NO 3
<211> LENGTH: 7
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 3

Ile Ile Leu Leu Gln Ala Arg
1               5

<210> SEQ ID NO 4
<211> LENGTH: 7
<212> TYPE: PRT
<213> ORGANISM: Artificial Geqence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 4

Ile Asp Leu Met Gln Ala Arg
1               5

<210> SEQ ID NO 5
<211> LENGTH: 7
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 5

Ile Ser Leu Leu Gln Ala Arg
1               5

<210> SEQ ID NO 6
<211> LENGTH: 7
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 6

Phe Ser Leu Leu Asp Ala Arg
1               5
```

<210> SEQ ID NO 7
<211> LENGTH: 7
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 7

Ile Ser Leu Leu Gly Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 8

Pro Leu Trp Arg Pro Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 9

Leu Leu Leu Met Gln Leu Arg
1               5

<210> SEQ ID NO 10
<211> LENGTH: 7
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(7)

<400> SEQUENCE: 10

Leu Tyr Leu Gln Arg Leu Arg
1               5

<210> SEQ ID NO 11
<211> LENGTH: 346
<212> TYPE: PRT
<213> ORGANISM: Rattus norvegicus
<220> FEATURE:
<221> NAME/KEY: PEPTIDE
<222> LOCATION: (1)..(346)
<223> OTHER INFORMATION: Anxa1 fragment

<400> SEQUENCE: 11

```
Met Ala Met Val Ser Glu Phe Leu Lys Gln Ala Arg Phe Leu Glu Asn
1               5                   10                  15

Gln Glu Gln Glu Tyr Val Gln Ala Val Lys Ser Tyr Lys Gly Gly Pro
            20                  25                  30

Gly Ser Ala Val Ser Pro Tyr Pro Ser Phe Asn Val Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Thr Asn Ala Gln Arg Gln Gln Ile
65                  70                  75                  80

Lys Ala Ala Tyr Leu Gln Glu Asn Gly Lys Pro Leu Asp Glu Val Leu
                85                  90                  95

Arg Lys Ala Leu Thr Gly His Leu Glu Glu Val Val Leu Ala Met Leu
            100                 105                 110

Lys Thr Pro Ala Gln Phe Asp Ala Asp Glu Ile Arg Gly Ala Met Lys
        115                 120                 125

Gly Leu Gly Thr Asp Glu Asp Thr Leu Ile Glu Ile Leu Thr Thr Arg
    130                 135                 140

Ser Asn Glu Gln Ile Arg Glu Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Lys Ala Leu Leu Ala Leu Ala Lys Gly Asp Arg Cys Gln Asp Leu
            180                 185                 190

Ser Val Asn Gln Asp Leu Ala Asp Thr Asp Ala Arg Ala Leu Tyr Glu
        195                 200                 205

Ala Gly Glu Arg Arg Lys Gly Thr Asp Leu Asn Leu Phe Thr Thr Ile
    210                 215                 220

Ile Thr Ser Arg Ser Phe Pro His Leu Arg Arg Val Phe Gln Asn Tyr
225                 230                 235                 240

Gly Lys Tyr Ser Gln His Asp Met Asn Lys Ala Leu Asp Leu Glu Leu
                245                 250                 255

Lys Gly Asp Ile Glu Lys Cys Leu Thr Thr Ile Val Lys Cys Ala Thr
            260                 265                 270

Ser Thr Pro Ala Phe Phe Ala Glu Lys Leu Tyr Glu Ala Met Lys Gly
        275                 280                 285

Ala Gly Thr Arg His Lys Ala Leu Ile Arg Ile Met Val Ser Arg Ser
    290                 295                 300

Glu Ile Asp Met Asn Glu Ile Lys Val Phe Tyr Gln Lys Tyr Gly
305                 310                 315                 320

Ile Ser Leu Cys Gln Ala Ile Leu Asp Glu Thr Lys Gly Asp Tyr Glu
        325                 330                 335

Lys Ile Leu Val Ala Leu Cys Gly Gly Asn
            340                 345

<210> SEQ ID NO 12
<211> LENGTH: 11
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(11)

<400> SEQUENCE: 12
```

```
Ile Phe Leu Leu Trp Gln Arg Lys Lys Cys
1               5                   10

<210> SEQ ID NO 13
<211> LENGTH: 7
<212> TYPE: PRT
<213> ORGANISM: Artificial Sequence
<220> FEATURE:
<223> OTHER INFORMATION: chemically synthesized; selectin ligand mimic
<220> FEATURE:
<221> NAME/KEY: PEPTIDE
<222> LOCATION: (1)..(7)

<400> SEQUENCE: 13

Ile Glu Leu Leu Gln Ala Arg
1               5

<210> SEQ ID NO 14
<211> LENGTH: 8
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(8)

<400> SEQUENCE: 14

Ile Phe Leu Leu Trp Gln Arg Cys
1               5

<210> SEQ ID NO 15
<211> LENGTH: 7
<212> TYPE: PRT
<213> ORGANISM: Artificial Sequence
<220> FEATURE:
<223> OTHER INFORMATION: chemically synthesized; control peptide
<220> FEATURE:
<221> NAME/KEY: PEPTIDE
<222> LOCATION: (1)..(7)

<400> SEQUENCE: 15

Arg Gln Trp Leu Leu Phe Ile
1               5

<210> SEQ ID NO 16
<211> LENGTH: 10
<212> TYPE: PRT
<213> ORGANISM: Artificial Sequence
<220> FEATURE:
<223> OTHER INFORMATION: chemically synthesized; control peptide
<220> FEATURE:
<221> NAME/KEY: PEPTIDE
<222> LOCATION: (1)..(10)

<400> SEQUENCE: 16

Arg Gln Trp Leu Leu Phe Ile Cys Arg Arg
1               5                   10

<210> SEQ ID NO 17
<211> LENGTH: 9
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
```

```
<222> LOCATION: (1)..(9)

<400> SEQUENCE: 17

Ile Phe Leu Leu Trp Gln Arg Cys Arg
1               5

<210> SEQ ID NO 18
<211> LENGTH: 11
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(11)

<400> SEQUENCE: 18

Ile Phe Leu Leu Trp Gln Arg Cys Arg Arg Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(10)

<400> SEQUENCE: 19

Ile Phe Leu Leu Trp Gln Arg Cys Arg Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(11)
<223> OTHER INFORMATION: X can be any amino acid

<400> SEQUENCE: 20

Ile Phe Leu Leu Trp Gln Arg Xaa Xaa Xaa Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(12)
<223> OTHER INFORMATION: X can be any amino acid

<400> SEQUENCE: 21

Ile Phe Leu Leu Trp Gln Arg Cys Xaa Xaa Xaa Xaa
1               5                   10

<210> SEQ ID NO 22
```

```
<211> LENGTH: 12
<212> TYPE: PRT
<213> ORGANISM: Artificial Sequence
<220> FEATURE:
<223> OTHER INFORMATION: chemically synthesized; annexin-1 binding
      peptide
<220> FEATURE:
<221> NAME/KEY: PEPTIDE
<222> LOCATION: (1)..(12)

<400> SEQUENCE: 22

Ile Phe Leu Leu Trp Gln Arg Cys Arg Arg Arg Arg
1               5                   10

<210> SEQ ID NO 23
<211> LENGTH: 5
<212> TYPE: PRT
<213> ORGANISM: Artificial Sequence
<220> FEATURE:
<223> OTHER INFORMATION: chemically synthesized; cleavage site for
      enterokinase
<220> FEATURE:
<221> NAME/KEY: PEPTIDE
<222> LOCATION: (1)..(5)

<400> SEQUENCE: 23

Asp Asp Asp Asp Lys
1               5

<210> SEQ ID NO 24
<211> LENGTH: 14
<212> TYPE: PRT
<213> ORGANISM: Artificial Sequence
<220> FEATURE:
<223> OTHER INFORMATION: chemically synthesized; therapeutic agent
<220> FEATURE:
<221> NAME/KEY: PEPTIDE
<222> LOCATION: (1)..(14)

<400> SEQUENCE: 24

Lys Leu Ala Lys Leu Ala Lys Lys Leu Ala Lys Leu Ala Lys
1               5                   10

<210> SEQ ID NO 25
<211> LENGTH: 8
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(8)
<223> OTHER INFORMATION: X can be any amino acid

<400> SEQUENCE: 25

Ile Phe Leu Leu Trp Gln Arg Xaa
1               5

<210> SEQ ID NO 26
<211> LENGTH: 9
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(9)
<223> OTHER INFORMATION: X can be any amino acid
```

```
<400> SEQUENCE: 26

Ile Phe Leu Leu Trp Gln Arg Xaa Xaa
1               5

<210> SEQ ID NO 27
<211> LENGTH: 10
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(10)
<223> OTHER INFORMATION: X can be any amino acid

<400> SEQUENCE: 27

Ile Phe Leu Leu Trp Gln Arg Xaa Xaa Xaa
1               5                   10

<210> SEQ ID NO 28
<211> LENGTH: 12
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(12)
<223> OTHER INFORMATION: X can be any amino acid

<400> SEQUENCE: 28

Ile Phe Leu Leu Trp Gln Arg Xaa Xaa Xaa Xaa Xaa
1               5                   10

<210> SEQ ID NO 29
<211> LENGTH: 9
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(9)
<223> OTHER INFORMATION: X can be any amino acid

<400> SEQUENCE: 29

Ile Phe Leu Leu Trp Gln Arg Cys Xaa
1               5

<210> SEQ ID NO 30
<211> LENGTH: 10
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(10)
<223> OTHER INFORMATION: X can be any amino acid

<400> SEQUENCE: 30

Ile Phe Leu Leu Trp Gln Arg Cys Xaa Xaa
1               5                   10

<210> SEQ ID NO 31
```

```
<211> LENGTH: 11
<212> TYPE: PRT
<213> ORGANISM: Artificial Sequence
<220> FEATURE:
<223> OTHER INFORMATION: chemically synthesized; annexin-1 binding
      compound
<220> FEATURE:
<221> NAME/KEY: PEPTIDE
<222> LOCATION: (1)..(11)
<223> OTHER INFORMATION: X can be any amino acid

<400> SEQUENCE: 31

Ile Phe Leu Leu Trp Gln Arg Cys Xaa Xaa Xaa
1               5                   10
```

METHODS AND COMPOSITIONS RELATED TO ANNEXIN 1-BINDING COMPOUNDS

CROSS-REFERENCE TO RELATED APPLICATIONS

This application claims benefit of U.S. Provisional Application No. 61/289,833, filed Dec. 23, 2009. Application No. 61/289,833, filed Dec. 23, 2009, is hereby incorporated herein by reference in its entirety.

STATEMENT REGARDING FEDERALLY SPONSORED RESEARCH

This invention was made with government support under NIH grant P01CA071932 (MF and MNF), DoD Breast Cancer Research IDEA grant DAMD 17-02-1-0311 (MNF), and a Susan Komen Breast Cancer Research grant BCTR0504175 (MNF). The government has certain rights in this invention.

REFERENCE TO SEQUENCE LISTING

The Sequence Listing submitted Dec. 23, 2010 as a text file named "24520-47-9001-2010-12-23_AMD_AFD_Sequence_Listing Text_File.txt," created on Dec. 23, 2010, and having a size of 9357 bytes is hereby incorporated by reference pursuant to 37 C.F.R. §1.52(e)(5).

FIELD OF THE INVENTION

The present invention relates generally to the fields of molecular medicine and cancer biology, and, more specifically, to annexin 1-binding compounds that selectively home to tumor vasculature.

BACKGROUND OF THE INVENTION

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life.

BRIEF SUMMARY OF THE INVENTION

Disclosed are isolated peptides comprising an amino acid sequence that can bind to a carbohydrate receptor on a cell. Also disclosed are compositions comprising a moiety and a peptide comprising an amino acid sequence that can bind to a carbohydrate receptor on a cell. Also disclosed are isolated nucleic acids comprising a nucleic acid sequence encoding a peptide comprising an amino acid sequence that can bind to a carbohydrate receptor on a cell.

Also disclosed are methods comprising administering to a subject a composition comprising a moiety and a peptide comprising an amino acid sequence that can bind to a carbohydrate receptor on a cell. Also disclosed are methods of targeting a tumor cell in a subject comprising administering to the subject a peptide comprising an amino acid sequence that can bind to a carbohydrate receptor on a cell. Also disclosed are methods of targeting a tumor cell in a subject comprising administering to the subject a composition comprising a moiety and a peptide comprising an amino acid sequence that can bind to a carbohydrate receptor on a cell. Also disclosed are methods comprising administering to the subject a composition comprising a peptide comprising an amino acid sequence that can bind to a carbohydrate receptor on a cell and detecting the composition in the subject.

The carbohydrate receptor can be annexin 1. The amino acid sequence can selectively bind the carbohydrate receptor. The subject can comprise a cell. The cell can be a tumor cell. The peptide can be an annexin 1-binding compound. The amino acid sequence can be an annexin 1-binding compound.

The amino acid sequence can comprise SEQ ID NO:2 having one or more conservative amino acid substitutions. The amino acid sequence can have at least 55% sequence identity to SEQ ID NO:2, wherein differences between the amino acid sequence and SEQ ID NO:2 consist of conservative amino acid substitutions. The amino acid sequence can have at least 70% sequence identity to SEQ ID NO:2. The amino acid sequence can have at least 80% sequence identity to SEQ ID NO:2. The amino acid sequence can comprise SEQ ID NO:2. The amino acid sequence can consist of SEQ ID NO:2. The amino acid sequence can comprise at least 5 consecutive amino acids of SEQ ID NO:2. The amino acid sequence can comprise at least 6 consecutive amino acids of SEQ ID NO:2.

The peptide can comprise SEQ ID NO:2. The peptide can comprise at least 6 amino acids. The peptide can comprise at least 7 amino acids. The peptide can comprise at least 8 amino acids. The peptide can comprise at least 9 amino acids. The peptide can further comprise a moiety peptide.

The moiety can be a small molecule, pharmaceutical drug, toxin, fatty acid, detectable marker, conjugating tag, nanoshell, or enzyme. The moiety can be covalently linked to the peptide. The moiety can be linked to the amino terminal end of the peptide. The moiety can be linked to the carboxy terminal end of the peptide. The moiety can be linked to an amino acid within the peptide. The moiety can be SN-38. The moiety can comprise a detectable agent. The moiety can comprise a therapeutic agent.

The composition can further comprise a linker connecting the moiety and the peptide. The composition can further comprise a pharmaceutically acceptable carrier. The composition can further comprise a detectable agent. The composition can further comprise a therapeutic agent. The composition can further comprise an anti-cancer agent.

Detecting the composition in the method can thereby detect a tumor in the subject. Detecting the composition in the method can thereby diagnose cancer in the subject. Detecting the composition in the method can comprise detecting the level, amount, concentration, or a combination of binding of the composition to cancer tissue in the subject, wherein the level, amount, concentration, or a combination of binding of the composition to cancer tissue in the subject indicates the prognosis of the cancer in the subject. The method can further comprise repeating the administration and detection at a later time, wherein a change in the level, amount, concentration, or a combination of binding of the composition to cancer tissue in the subject indicates the progress of the endometriosis in the subject. The method can further comprise repeating the administration and detection following treatment, wherein a change in the level, amount, concentration, or a combination of binding of the composition to cancer tissue in the subject indicates the progress the treatment of the cancer in the subject.

The peptides selectively bind to tumor vasculature. The amino acid sequences selectively bind to tumor vasculature. The peptides can comprise a plurality of amino acid sequences, wherein the amino acid sequences selectively bind to tumor vasculature. The peptides can bind to tumor vasculature. The amino acid sequences can bind to tumor vasculature. The peptides can comprise a plurality of amino acid sequences, wherein the amino acid sequences can bind to tumor vasculature.

The peptides selectively bind to a carbohydrate receptor on a cell. The amino acid sequences selectively bind to a carbohydrate receptor on a cell. The peptides can comprise a plurality of amino acid sequences, wherein the amino acid sequences selectively bind to a carbohydrate receptor on a cell. The peptides can bind to a carbohydrate receptor on a cell. The amino acid sequences can bind to a carbohydrate receptor on a cell. The peptides can comprise a plurality of amino acid sequences, wherein the amino acid sequences can bind to a carbohydrate receptor on a cell.

The peptides selectively bind to a carbohydrate receptor on a cell. The amino acid sequences selectively bind to annexin 1 on a cell. The peptides can comprise a plurality of amino acid sequences, wherein the amino acid sequences selectively bind to annexin 1 on a cell. The peptides can bind to a carbohydrate receptor on a cell. The amino acid sequences can bind to annexin 1 on a cell. The peptides can comprise a plurality of amino acid sequences, wherein the amino acid sequences can bind to annexin 1 on a cell.

The peptides selectively bind to a carbohydrate receptor on a cell. The amino acid sequences selectively bind to annexin 1 on tumor vasculature. The peptides can comprise a plurality of amino acid sequences, wherein the amino acid sequences selectively bind to annexin 1 on tumor vasculature. The peptides can bind to a carbohydrate receptor on tumor vasculature. The amino acid sequences can bind to annexin 1 on tumor vasculature. The peptides can comprise a plurality of amino acid sequences, wherein the amino acid sequences can bind to annexin 1 on tumor vasculature.

The peptides selectively bind to a carbohydrate receptor on a cell. The amino acid sequences selectively bind to annexin 1 on tumor vasculature. The peptides can comprise a plurality of amino acid sequences, wherein the amino acid sequences selectively bind to annexin 1 on tumor vasculature. The peptides can bind to a carbohydrate receptor on tumor vasculature. The amino acid sequences can bind to annexin 1 on tumor vasculature. The peptides can comprise a plurality of amino acid sequences, wherein the amino acid sequences can bind to annexin 1 on tumor vasculature.

The composition can comprise a plurality of peptides, wherein the peptides selectively bind to tumor vasculature. The peptide can comprise a plurality of amino acid sequences, wherein the amino acid sequences selectively bind to tumor vasculature. The composition can comprise a plurality of amino acid sequences, wherein the amino acid sequences selectively bind to tumor vasculature. The composition can comprise a plurality of peptides, wherein at least one of the peptides comprises an amino acid sequence that selectively binds to tumor vasculature. The composition can comprise a plurality of peptides, wherein a plurality of the peptides each comprises an amino acid sequence that selectively binds to tumor vasculature. The composition can comprise a plurality of peptides, wherein the peptides each comprise an amino acid sequence that selectively binds to tumor vasculature.

The composition can comprise a plurality of peptides, wherein the peptides selectively bind to a carbohydrate receptor on a cell. The peptide can comprise a plurality of amino acid sequences, wherein the amino acid sequences selectively bind to a carbohydrate receptor on a cell. The composition can comprise a plurality of amino acid sequences, wherein the amino acid sequences selectively bind to a carbohydrate receptor on a cell. The composition can comprise a plurality of peptides, wherein at least one of the peptides comprises an amino acid sequence that bind to a carbohydrate receptor on a cell. The composition can comprise a plurality of peptides, wherein a plurality of the peptides each comprise an amino acid sequence that selectively bind to a carbohydrate receptor on a cell. The composition can comprise a plurality of peptides, wherein the peptides each comprise an amino acid sequence that selectively bind to a carbohydrate receptor on a cell.

The composition can comprise a plurality of peptides, wherein the peptides can bind to a carbohydrate receptor on a cell. The peptide can comprise a plurality of amino acid sequences, wherein the amino acid sequences can bind to a carbohydrate receptor on a cell. The composition can comprise a plurality of amino acid sequences, wherein the amino acid sequences can bind to a carbohydrate receptor on a cell. The composition can comprise a plurality of peptides, wherein at least one of the peptides comprises an amino acid sequence that s can bind to a carbohydrate receptor on a cell. The composition can comprise a plurality of peptides, wherein a plurality of the peptides each comprise an amino acid sequence that can bind to a carbohydrate receptor on a cell. The composition can comprise a plurality of peptides, wherein the peptides each comprise an amino acid sequence that can bind to a carbohydrate receptor on a cell.

The composition can comprise a plurality of peptides, wherein the peptides selectively bind to annexin 1 on a cell. The peptide can comprise a plurality of amino acid sequences, wherein the amino acid sequences selectively bind to annexin 1 on a cell. The composition can comprise a plurality of amino acid sequences, wherein the amino acid sequences selectively bind to annexin 1 on a cell. The composition can comprise a plurality of peptides, wherein at least one of the peptides comprises an amino acid sequence that bind to annexin 1 on a cell. The composition can comprise a plurality of peptides, wherein a plurality of the peptides each comprise an amino acid sequence that selectively bind to annexin 1 on a cell. The composition can comprise a plurality of peptides, wherein the peptides each comprise an amino acid sequence that selectively bind to annexin 1 on a cell.

The composition can comprise a plurality of peptides, wherein the peptides can bind to annexin 1 on a cell. The peptide can comprise a plurality of amino acid sequences, wherein the amino acid sequences can bind to annexin 1 on a cell. The composition can comprise a plurality of amino acid sequences, wherein the amino acid sequences can bind to annexin 1 on a cell. The composition can comprise a plurality of peptides, wherein at least one of the peptides comprises an amino acid sequence that can bind to annexin 1 on a cell. The composition can comprise a plurality of peptides, wherein a plurality of the peptides each comprise an amino acid sequence that can bind to annexin 1 on a cell. The composition can comprise a plurality of peptides, wherein the peptides each comprise an amino acid sequence that can bind to annexin 1 on a cell.

The composition can comprise a plurality of peptides, wherein the peptides selectively bind to annexin 1 on tumor vasculature. The peptide can comprise a plurality of amino acid sequences, wherein the amino acid sequences selectively bind to annexin 1 on tumor vasculature. The composition can comprise a plurality of amino acid sequences, wherein the amino acid sequences selectively bind to annexin 1 on tumor vasculature. The composition can comprise a plurality of peptides, wherein at least one of the peptides comprises an amino acid sequence that bind to annexin 1 on tumor vasculature. The composition can comprise a plurality of peptides, wherein a plurality of the peptides each comprise an amino acid sequence that selectively bind to annexin 1 on tumor vasculature. The composition can comprise a plurality of peptides, wherein the peptides each comprise an amino acid sequence that selectively bind to annexin 1 on tumor vasculature.

The composition can comprise a plurality of peptides, wherein the peptides can bind to annexin 1 on tumor vasculature. The peptide can comprise a plurality of amino acid sequences, wherein the amino acid sequences can bind to annexin 1 on tumor vasculature. The composition can comprise a plurality of amino acid sequences, wherein the amino acid sequences can bind to annexin 1 on tumor vasculature. The composition can comprise a plurality of peptides, wherein at least one of the peptides comprises an amino acid sequence that can bind to annexin 1 on tumor vasculature. The composition can comprise a plurality of peptides, wherein a plurality of the peptides each comprise an amino acid sequence that can bind to annexin 1 on tumor vasculature. The composition can comprise a plurality of peptides, wherein the peptides each comprise an amino acid sequence that can bind to annexin 1 on tumor vasculature.

The amino acid sequences, peptides, and compositions can bind inside tumor blood vessels. The composition can reduce tumor growth. The composition can comprise at least 100 annexin 1-binding amino acid sequences. The composition can comprise at least 1000 annexin 1-binding amino acid sequences. The composition can comprise at least 10,000 annexin 1-binding amino acid sequences.

The composition can comprise one or more moieties. The moieties can be independently selected from the group consisting of, for example, an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, and a small molecule. At least one of the moieties can be a therapeutic agent. The therapeutic agent can comprise a compound or composition for treating cancer. The therapeutic agent can comprise a compound or composition to induce programmed cell death or apoptosis. The therapeutic agent can be Abraxane. The therapeutic agent can be paclitaxel. The therapeutic agent can be docetaxel. At least one of the moieties can be a detectable agent. The detectable agent can be FAM.

The amino acid sequences, peptides, and compositions can selectively home to tumor vasculature. The composition can have a therapeutic effect. The therapeutic effect can be a slowing in the increase of or a reduction of tumor burden. The therapeutic effect can be a slowing of the increase of or a reduction of tumor size. The therapeutic effect can be a reduction or blocking of blood circulation in a tumor.

The subject can have one or more sites to be targeted, wherein the composition homes to one or more of the sites to be targeted. The subject can have a tumor, wherein the composition has a therapeutic effect on the tumor.

Sufficiency of the number and composition of annexin 1-binding amino acid sequences can be determined by assessing accumulation of the composition in tumors in, for example, a subject or a non-human animal.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1A:
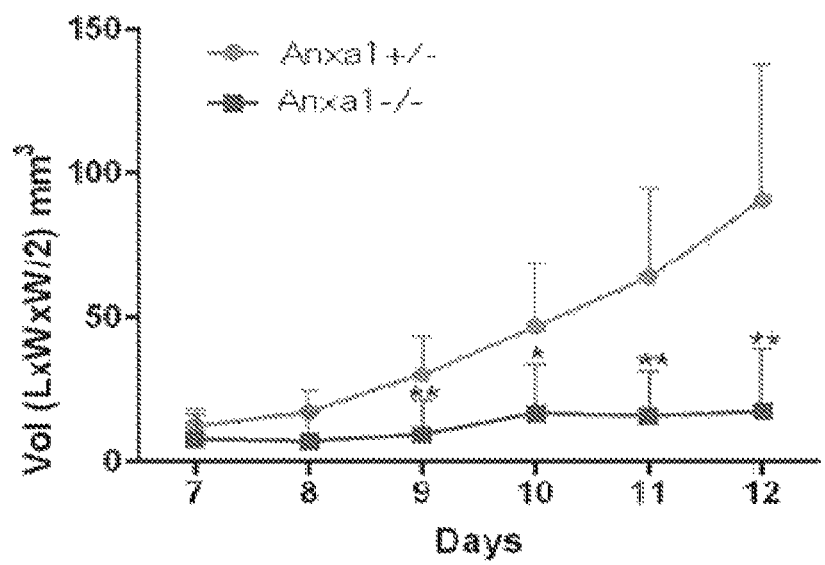
FIGS. 1A-1H show the essential role of annexin 1 (Anxa1) in tumor growth and identification of a peptide sequence with tumor vasculature targeting activity in vivo. A and B. Growth of B16 tumors subcutaneously injected into Anxa1(+/−) and Anxa1(−/−) mutant mice. C. Histology of B16 tumors produced in Anxa1(+/−) and Anxa1(−/−) mice. Each scale bar represents 2.00 mm. D. Immunohistochemistry of B16 tumors for CD31 showing endothelial cells and vasculature. Each scale bar represents 200 μm. E. In vivo phage targeting in B16 tumor-bearing mice. Numbers of transformed colonies recovered from the tumor or lung were determined. Peptide sequences displayed by clones 1-10 are: IELLQAR (1; SEQ ID NO: 1), IFLLWQR (2; SEQ ID NO:2), IILLQAR (3; SEQ ID NO:3), IDLMQAR (4; SEQ ID NO:4), ISLLQAR (5; SEQ ID NO:5), FSLLDAR (6; SEQ ID NO:6), ISLLGAR (7; SEQ ID NO:7), PLWRPSR (8; SEQ ID NO:8), LLLMQLR (9; SEQ ID NO:9), and LYLQRLR (10; SEQ ID NO:10). F. In vivo tumor and organ targeting activity of IFLLWQR (SEQ ID NO:2) displaying phage. Phage was injected into B16 tumor bearing mice pre-injected with anti-Anxa1 antibody or with control rabbit IgG. G. In vitro plate assay for binding of IF7-A488 (upper line) and control RQ7-A488C (lower line) to recombinant IF7-His$_6$ protein produced by bacteria. H. Effect of IF7 (upper line) and control RQ7 (lower line) on binding of FITC-labeled polyacrylamide-LeA oligosaccharide to Anxa1-His$_6$ protein.

The disclosed methods and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Chemotherapeutics administered to cancer patients intravenously become diluted, therefore requiring high doses and causing side effects, which could be circumvented by targeted drug delivery (Ruoslahti E. et al. Annu Rev Immunol 2000; 18:813-27; Neri, D. et al. Nat Rev Cancer 2005; 5:436-46; Bellone, M. et al. Trends Immunol 2008; 29:235-41). Because malignancy is closely associated with cancer cell surface carbohydrates, it was realized that carbohydrate-based therapeutics are desirable. Such therapeutics have previously not been explored. It was discovered that one carbohydrate mimicry peptide, designated I-peptide, bound to annexin 1 (Anxa1) (Hatakeyama, S. et al., Proc Natl Acad Sci 2009; 106: 3095-100). As Anxa1 specifically marks tumor vasculature (Oh, P. et al. Nature 2004; 429:629-35), it has been discovered that the I-peptide can serve as a tumor-targeting vehicle. Investigating I-peptide related sequences (Fukuda, M. et al., Cancer Res 2000; 60:450-6; Zhang, J. et al. Cancer Res 2002; 62:4194-8; Fukuda, M. Methods Enzymol 2006; 416:51-60), lead to the identification of a peptide designated IF7 that specifically homes to tumors with high efficacy. Upon intravenous injection, IF7 conjugated with the potent anti-cancer drug SN-38 rescued terminal stage mice harboring B16 tumors. IF7-SN38 also prolonged survival of mice with peritoneal B16 tumors without side effects. These results indicate that annexin 1-binding compounds can be used for targeted chemotherapy.

Technical advances in genomics and proteomics together with automated chemical synthesis of DNA and proteins have greatly contributed to progress in biomedicine. By contrast, the use and understanding of the role of carbohydrates have lagged behind due to lack of advanced technologies. For example, recombinant or amplifiable carbohydrates or chemically synthesized complex carbohydrates cannot be produced automatically. Consequently, carbohydrate-based drug discovery has been largely unexplored even though cancer malignancy is closely associated with carbohydrate structures found on the tumor cell surface (Hakomori, S. Proc Natl Acad Sci, 2002; 99: 10231-3; Nakamori, S. et al. Cancer Res 1993; 53: 3632-7). Peptide-displaying phage technology can be used to identify carbohydrate mimicry peptides (Fukuda, M. et al., Cancer Res 2000; 60: 450-6; Fukuda, M. Methods Enzymol 2006; 416: 51-60; Taki, T. et al. Biochim Biophys Acta 2008; 1780: 497-503; Scott, J. et al. Proc Natl Acad Sci 1992; 89: 5398-402). For example, 1-peptide (IELLQAR; SEQ ID NO: 13), was identified as a selectin ligand mimic, and when injected intravenously into mice, synthetic I-peptide inhibited carbohydrate-dependent cancer cell colonization to the lung (Fukuda, M. et al., Cancer Res 2000; 60: 450-6; Zhang, J. et al. Cancer Res 2002; 62: 4194-8).

Experiments designed to identify endothelial I-peptide receptors, revealed that I-peptide binds to a fragment of annexin 1 (Anxa1) (Hatakeyama, S. et al., Proc Natl Acad Sci 2009; 106: 3095-100). The peptide sequence identified in an Anxa1 fragment isolated from the rat lung by I-peptide affinity chromatography is SEQ ID NO: 11. The protein band at 15 kDa was digested with trypsin and the peptide fragments were analyzed by mass-spectroscopy. Unique peptide sequences that led to the identification of Anxa1 are shown by underlining.

```
                                              (SEQ ID NO: 11)
MAMVSEFLKQARFLENQEQEYVQAVKSYKGGPGSAVSPYPSFNVSSDVA

ALHKAIMVKGVDEATIIDILTKRTNAQRQQIKAAYLQENGKPLDEVLRK

ALTGHLEEVVLAMLKTPAQFDADELRGAMKGLGTDEDTLIEILTTRSNE

QIREINRVYREELKRDLAKDITSDTSGDFRKALLALAKGDRCQDLSVNQ

DLADTDARALYEAGERRKGTDVNVFTTILTSRSFPHLRRVFQNYGKYSQ

HDMNKALDLELKGDIEKCLTTIVKCATSTPAFFAEKLYEAMKGAGTRHK

ALIRIMVSRSEIDMNEIKVFYQKKYGISLCQAILDETKGDYEKILVALC

GGN.
```

Anxa1 has been identified as a specific tumor endothelial cell surface marker (Oh, P. et al. Nature 2004; 429: 629-35). When B16 melanoma cells were injected subcutaneously in Anxa1 null mutant mice, tumor growth was significantly reduced compared to tumors produced in Anxa1 heterozygous mice (see FIGS. 1A and 1B). Tumors produced in Anxa1 nulls were largely necrotic (see FIG. 1C). Remarkably, no vasculature was found in tumors produced in Anxa1 null mice (see FIG. 1D). These findings indicate that Anxa1 expression on the endothelial cell surface (Oh, P. et al. Nature 2004; 429: 629-35) is essential for active tumor growth in the mouse.

Disclosed are isolated peptides comprising an amino acid sequence that can bind to a carbohydrate receptor on a cell. Also disclosed are compositions comprising a moiety and a peptide comprising an amino acid sequence that can bind to a carbohydrate receptor on a cell. Also disclosed are isolated nucleic acids comprising a nucleic acid sequence encoding a peptide comprising an amino acid sequence that can bind to a carbohydrate receptor on a cell.

Also disclosed are methods comprising administering to a subject a composition comprising a moiety and a peptide comprising an amino acid sequence that can bind to a carbohydrate receptor on a cell. Also disclosed are methods of targeting a tumor cell in a subject comprising administering to the subject a peptide comprising an amino acid sequence that can bind to a carbohydrate receptor on a cell. Also disclosed are methods of targeting a tumor cell in a subject comprising administering to the subject a composition comprising a moiety and a peptide comprising an amino acid sequence that can bind to a carbohydrate receptor on a cell. Also disclosed are methods comprising administering to the subject a composition comprising a peptide comprising an amino acid sequence that can bind to a carbohydrate receptor on a cell and detecting the composition in the subject.

The carbohydrate receptor can be annexin 1. The amino acid sequence can selectively bind the carbohydrate receptor. The subject can comprise a cell. The cell can be a tumor cell.

The amino acid sequence can comprise SEQ ID NO:2 having one or more conservative amino acid substitutions. The amino acid sequence can have at least 55% sequence identity to SEQ ID NO:2, wherein differences between the amino acid sequence and SEQ ID NO:2 consist of conservative amino acid substitutions. The amino acid sequence can have at least 70% sequence identity to SEQ ID NO:2. The amino acid sequence can have at least 80% sequence identity to SEQ ID NO:2. The amino acid sequence can comprise SEQ ID NO:2. The amino acid sequence can consist of SEQ ID NO:2. The amino acid sequence can comprise at least 5 consecutive amino acids of SEQ ID NO:2. The amino acid sequence can comprise at least 6 consecutive amino acids of SEQ ID NO:2.

The peptide can comprise SEQ ID NO:2. The peptide can comprise at least 6 amino acids. The peptide can comprise at least 7 amino acids. The peptide can comprise at least 8 amino acids. The peptide can comprise at least 9 amino acids. The peptide can further comprise a moiety peptide.

The moiety can be a small molecule, pharmaceutical drug, toxin, fatty acid, detectable marker, conjugating tag, nanoshell, or enzyme. The moiety can be covalently linked to the peptide. The moiety can be linked to the amino terminal end of the peptide. The moiety can be linked to the carboxy terminal end of the peptide. The moiety can be linked to an amino acid within the peptide. The moiety can be SN-38. The moiety can comprise a detectable agent. The moiety can comprise a therapeutic agent.

The composition can further comprise a linker connecting the moiety and the peptide. The composition can further comprise a pharmaceutically acceptable carrier. The composition can further comprise a detectable agent. The composition can further comprise a therapeutic agent. The composition can further comprise an anti-cancer agent.

Detecting the composition in the method can thereby detect a tumor in the subject. Detecting the composition in the method can thereby diagnose cancer in the subject. Detecting the composition in the method can comprise detecting the level, amount, concentration, or a combination of binding of the composition to cancer tissue in the subject, wherein the level, amount, concentration, or a combination of binding of the composition to cancer tissue in the subject indicates the prognosis of the cancer in the subject. The method can further comprise repeating the administration and detection at a later time, wherein a change in the level, amount, concentration, or a combination of binding of the composition to cancer tissue in the subject indicates the progress of the endometriosis in the subject. The method can further comprise repeating the administration and detection following treatment, wherein a change in the level, amount, concentration, or a combination of binding of the composition to cancer tissue in the subject indicates the progress the treatment of the cancer in the subject.

Disclosed are methods of determining and/or assessing annexin 1 level in a cell of a subject. The method can comprise bringing into contact a cell of the subject and an annexin 1-binding composition comprising, for example, a detectable agent linked to a composition comprising SEQ ID NO: 2; and detecting the level of annexin 1-binding composition interacting with annexin 1, thereby determining and/or assessing annexin 1 level in the cell.

Disclosed herein are methods of identifying a subject having a disease associated with annexin 1, the method comprising bringing into contact a cell of the subject and an annexin 1-binding composition, wherein the annexin 1-binding composition comprises, for example, a moiety linked to a composition comprising SEQ ID NO:2; and detecting interaction between annexin 1 and the annexin 1-binding composition, thereby detecting the presence or level of annexin 1 on the cell, wherein the presence or level of annexin 1 receptor on the cell identifies the subject as having a disease associated with annexin 1.

Disclosed herein are subjects having a disease associated with annexin 1. By this is meant that the subject has an increased level of annexin 1 or that annexin 1 can be effectively targeted to treat or ameliorate the symptoms of a disease or disorder. By an "increased level of annexin 1" is meant that the number of annexin 1 molecules on selected cells or tissues in the subject is increased over normal, basal, or standard levels accepted by those of skill in the art. It can also mean that the number of annexin 1 molecules present in a given cell are increased over a basal, normal, or standard amount. One standard level that can be used for this purpose is the level of annexin 1 on normal lung endothelial cells. The standard level of annexin 1 can be determined using, for example, normal lung endothelial cells of the same subject, a different subject, or a group or population of individuals. One of skill in the art would be able to determine annexin 1 levels in a subject in cells and tissues, using the methods disclosed herein and those known to those of skill in the art. Diseases associated with the annexin 1 include some cancers, for example.

DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to" the value and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a caregiver's expertise, but that includes the knowledge that the subject is ill, or will be ill, as the result of a condition that is treatable by the compounds of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

Annexins are a family closely related calcium- and membrane-binding proteins expressed in most eukaryotic cell types. Their diverse functions include vesicle trafficking, cell division, apoptosis, calcium signaling, and growth regulation Annexins are linked to some of the most serious human diseases such as cardiovascular disease and cancer. Annexin 1, a 37 kDa protein, originally termed lipocortin, inhibits the inflammatory response and participates in several cellular functions, including phagocytosis, extravasation, mediator generation and neutrophil recruitment. In addition, annexin 1 can affect cells relevant to the inflammatory process, such as endothelial, epithelial, mast and synovial cells.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The disclosed amino acid sequences can bind to a carbohydrate receptor on a cell. The disclosed peptides can comprise an amino acid sequence that can bind to a carbohydrate receptor on a cell. The disclosed compositions can comprise a moiety and a peptide comprising an amino acid sequence that can bind to a carbohydrate receptor on a cell. The disclosed are isolated nucleic acids can comprise a nucleic acid sequence encoding a peptide comprising an amino acid sequence that can bind to a carbohydrate receptor on a cell.

The amino acid sequence can comprise SEQ ID NO:2 having one or more conservative amino acid substitutions. The amino acid sequence can have at least 55% sequence identity to SEQ ID NO:2, wherein differences between the amino acid sequence and SEQ ID NO:2 consist of conservative amino acid substitutions. The amino acid sequence can have at least 70% sequence identity to SEQ ID NO:2. The amino acid sequence can have at least 80% sequence identity to SEQ ID NO:2. The amino acid sequence can comprise SEQ ID NO:2. The amino acid sequence can consist of SEQ ID NO:2. The amino acid sequence can comprise at least 5 consecutive amino acids of SEQ ID NO:2. The amino acid sequence can comprise at least 6 consecutive amino acids of SEQ ID NO:2.

The peptide can comprise SEQ ID NO:2. The peptide can comprise at least 6 amino acids. The peptide can comprise at least 7 amino acids. The peptide can comprise at least 8 amino acids. The peptide can comprise at least 9 amino acids. The peptide can further comprise a moiety peptide.

The composition can bind inside tumor blood vessels. The composition can reduce tumor growth. The composition can comprise at least 100 annexin 1-binding amino acid sequences. The composition can comprise at least 1000 annexin 1-binding amino acid sequences. The composition can comprise at least 10,000 annexin 1-binding amino acid sequences.

The composition can further comprise one or more moieties. The moieties can be independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, and a small molecule. At least one of the moieties can be a therapeutic agent. The therapeutic agent can comprise a compound or composition for treating cancer. The therapeutic agent can comprise a compound or composition to induce programmed cell death or apoptosis. The therapeutic agent can be Abraxane. The therapeutic agent can be paclitaxel. The therapeutic agent can be docetaxel. At least one of the moieties can be a detectable agent. The detectable agent can be FAM.

The composition can selectively home to tumor vasculature. The composition can have a therapeutic effect. The therapeutic effect can be a slowing in the increase of or in a reduction of tumor burden. The therapeutic effect can be a slowing of the increase of or a reduction of tumor size. The therapeutic effect can be a reduction or blocking of blood circulation in a tumor.

A. Annexin 1-Binding Compounds

The annexin 1-binding compound can be any compound with the ability to interact with annexin 1. The annexin 1-binding compound can be an annexin 1-binding amino acid sequence. The disclosed amino acid sequences can be annexin 1-binding amino acid sequences Annexin 1-binding compounds can, for example, bind to annexin 1, selectively bind to annexin 1, home to annexin 1-containing cells and tissue, target annexin 1-containing cells and tissue, bind to tumor vasculature, selectively bind to tumor vasculature, accumulate at annexin 1-containing cells and tissue, and accumulate in tumor vasculature. The disclosed annexin 1-binding compounds and amino acid sequences can be homing molecules or homing peptides.

The annexin 1-binding compound can comprise SEQ ID NO:2 having one or more conservative amino acid substitutions. The annexin 1-binding compound can have at least 55% sequence identity to SEQ ID NO:2, wherein differences between the annexin 1-binding compound and SEQ ID NO:2 consist of conservative amino acid substitutions. The annexin 1-binding compound can have at least 70% sequence identity to SEQ ID NO:2. The annexin 1-binding compound can have at least 80% sequence identity to SEQ ID NO:2. The annexin 1-binding compound can comprise SEQ ID NO:2. The annexin 1-binding compound can consist of SEQ ID NO:2. The annexin 1-binding compound can comprise at least 5 consecutive amino acids of SEQ ID NO:2. The annexin 1-binding compound can comprise at least 6 consecutive amino acids of SEQ ID NO:2. The annexin 1-binding compound can comprises at least 6 amino acids. The annexin 1-binding compound can comprise at least 7 amino acids. The peptide can comprise at least 8 amino acids. The annexin 1-binding compound can comprise at least 9 amino acids. The annexin 1-binding compound can comprise at least 10 amino acids. The annexin 1-binding compound can comprise at least 11 amino acids. The annexin 1-binding compound can comprise at least 12 amino acids. The annexin 1-binding compound can comprise at least 13 amino acids. The annexin 1-binding compound can comprise at least 14 amino acids. The annexin 1-binding compound can comprise at least 15 amino acids.

The annexin 1-binding compound can comprise an amino acid sequence comprising SEQ ID NO:2 having one or more conservative amino acid substitutions. The annexin 1-binding compound can comprise an amino acid sequence having at least 55% sequence identity to SEQ ID NO:2, wherein differences between the amino acid sequence and SEQ ID NO:2 consist of conservative amino acid substitutions. The annexin 1-binding compound can comprise an amino acid sequence having at least 70% sequence identity to SEQ ID NO:2. The annexin 1-binding compound can comprise an amino acid sequence having at least 80% sequence identity to SEQ ID NO:2. The annexin 1-binding compound can comprise an amino acid sequence comprising SEQ ID NO:2. The annexin 1-binding compound can comprise an amino acid sequence consisting of SEQ ID NO:2. The annexin 1-binding compound can comprise an amino acid sequence comprising at least 5 consecutive amino acids of SEQ ID NO:2. The annexin 1-binding compound can comprise an amino acid sequence comprising at least 6 consecutive amino acids of SEQ ID NO:2. The annexin 1-binding compound can comprise a peptide comprising SEQ ID NO:2. The annexin 1-binding compound can comprise a peptide comprising at least 6 amino acids. The annexin 1-binding compound can comprise a peptide comprising at least 7 amino acids. The annexin 1-binding compound can comprise a peptide comprising at least 8 amino acids. The annexin 1-binding compound can comprise a peptide comprising at least 9 amino acids. The annexin 1-binding compound can comprise a peptide comprising at least 10 amino acids. The annexin 1-binding compound can comprise a peptide comprising at least 11 amino acids. The annexin 1-binding compound can comprise a peptide comprising at least 12 amino acids. The annexin 1-binding compound can comprise a peptide comprising at least 13 amino acids. The annexin 1-binding compound can comprise a peptide comprising at least 14 amino acids. The annexin 1-binding compound can comprise a peptide comprising at least 15 amino acids.

The annexin 1-binding compound can consist of an amino acid sequence comprising SEQ ID NO:2 having one or more conservative amino acid substitutions. The annexin 1-binding compound can consist of an amino acid sequence having at least 55% sequence identity to SEQ ID NO:2, wherein differences between the amino acid sequence and SEQ ID NO:2 consist of conservative amino acid substitutions. The annexin 1-binding compound can consist of an amino acid sequence having at least 70% sequence identity to SEQ ID NO:2. The annexin 1-binding compound can consist of an amino acid sequence having at least 80% sequence identity to SEQ ID NO:2. The annexin 1-binding compound can consist of an amino acid sequence comprising SEQ ID NO:2. The annexin 1-binding compound can consist of an amino acid sequence consisting of SEQ ID NO:2. The annexin 1-binding compound can consist of an amino acid sequence comprising at least 5 consecutive amino acids of SEQ ID NO:2. The annexin 1-binding compound can consist of an amino acid sequence comprising at least 6 consecutive amino acids of SEQ ID NO:2. The annexin 1-binding compound can consist of a peptide comprising SEQ ID NO:2. The annexin 1-binding compound can consist of a peptide comprising at least 6 amino acids. The annexin 1-binding compound can consist of a peptide comprising at least 7 amino acids. The annexin 1-binding compound can consist of a peptide comprising at least 8 amino acids. The annexin 1-binding compound can consist of a peptide comprising at least 9 amino acids. The annexin 1-binding compound can consist of a peptide comprising at least 10 amino acids. The annexin 1-binding compound can consist of a peptide comprising at least 11 amino acids. The annexin 1-binding compound can consist of a peptide comprising at least 12 amino acids. The annexin 1-binding compound can consist of a peptide comprising at least 13 amino acids. The annexin 1-binding compound can consist of a peptide comprising at least 14 amino acids. The annexin 1-binding compound can consist of a peptide comprising at least 15 amino acids.

The annexin 1-binding compound can comprise IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a polar or charged amino acid. For example, each X can independently be selected from all, any set of 10, any set of 9, any set of 8, any set of 7, any set of 6, any set of 5, any set of 4, any set of 3, any set of 2, or any 1 of the amino acids C, R, K, S, T, H, D, E, N, Q, and M. For example, each X can independently be selected from the set of three amino acids C, R, and K. As another example, each X can independently be selected from the set of two amino acids C and R. In some forms, a single one of the X can be C. In some forms, two of the X can be C. In some forms, two of the X can be R. In some forms, three of the X can be R. In some forms, four of the X can be R. As an example, the annexin 1-binding compound can comprise IFLLWQRCR (SEQ ID NO: 17), IFLLWQRCRR (SEQ ID NO: 19), IFLLWQRCRRR (SEQ ID NO: 18), or IFLLWQRCRRRR (SEQ ID NO:22).

The annexin 1-binding compound can comprise IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a C, R, K, S, T, H, D, E, N, Q, or M. In some forms, a single one of the X can be C. In some forms, two of the X can be C. In some forms, two of the X can be R. In some forms, three of the X can be R. In some forms, four of the X can be R.

The annexin 1-binding compound can comprise IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a C, R, or K. In some forms, a single one of the X can be C. In some forms, two of the X can be C. In some forms, two of the X can be R. In some forms, three of the X can be R. In some forms, four of the X can be R.

The annexin 1-binding compound can comprise IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a C or R. In some forms, a single one of the X can be C. In some forms, two of the X can be C. In some forms, two of the X can be R. In some forms, three of the X can be R. In some forms, four of the X can be R.

The annexin 1-binding compound can consist of IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a polar or charged amino acid. For example, each X can independently be selected from all, any set of 10, any set of 9, any set of 8, any set of 7, any set of 6, any set of 5, any set of 4, any set of 3, any set of 2, or any 1 of the amino acids C, R, K, S, T, H, D, E, N, Q, and M. For example, each X can independently be selected from the set of three amino acids C, R, and K. As another example, each X can independently be selected from the set of two amino acids C and R. In some forms, a single one of the X can be C. In some forms, two of the X can be C. In some forms, two of the X can be R. In some forms, three of the X can be R. In some forms, four of the X can be R. As an example, the annexin 1-binding compound can consist of IFLLWQRCR (SEQ ID NO: 17), IFLLWQRCRR (SEQ ID NO:19), IFLLWQRCRRR (SEQ ID NO: 18), or IFLLWQRCRRRR (SEQ ID NO:22).

The annexin 1-binding compound can consist of IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a C, R, K, S, T, H, D, E, N, Q, or M. In some forms, a single one of the X can be C. In some forms, two of the X can be C. In some forms, two of the X can be R. In some forms, three of the X can be R. In some forms, four of the X can be R.

The annexin 1-binding compound can consist of IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a C, R, or K. In some forms, a single one of the X can be C. In some forms, two of the X can be C. In some forms, two of the X can be R. In some forms, three of the X can be R. In some forms, four of the X can be R.

The annexin 1-binding compound can consist of IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20), wherein each X is independently a C or R. In some forms, a single one of the X can be C. In some forms, two of the X can be C. In some forms, two of the X can be R. In some forms, three of the X can be R. In some forms, four of the X can be R.

In some forms, the annexin 1-binding compound can have one or more conservative amino acid substitutions in amino acids 1 to 7 of SEQ ID NO:20. In some forms, the portion of the annexin 1-binding compound corresponding to the sequence IFLLWQR (amino acids 1 to 7 of SEQ ID NO:20) can have at least 55% sequence identity to the sequence IFLLWQR (amino acids 1 to 7 of SEQ ID NO:20), wherein differences between the annexin 1-binding compound and IFLLWQR (amino acids 1 to 7 of SEQ ID NO:20) consist of conservative amino acid substitutions. In some forms, the portion of the annexin 1-binding compound corresponding to the sequence IFLLWQR (amino acids 1 to 7 of SEQ ID NO:20) can have at least 70% sequence identity to the sequence IFLLWQR (amino acids 1 to 7 of SEQ ID NO:20). In some forms, the portion of the annexin 1-binding compound corresponding to the sequence IFLLWQR (amino acids 1 to 7 of SEQ ID NO:20) can have at least 80% sequence identity to the sequence IFLLWQR (amino acids 1 to 7 of SEQ ID NO:20). In some forms, the annexin 1-binding compound has at least 5 consecutive amino acids of the sequence IFLLWQR (amino acids 1 to 7 of SEQ ID NO:20). In some forms, the annexin 1-binding compound has at least 6 consecutive amino acids of the sequence IFLLWQR (amino acids 1 to 7 of SEQ ID NO:20).

The annexin 1-binding compound can comprise IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a polar or charged amino acid. For example, each X can independently be selected from all, any set of 10, any set of 9, any set of 8, any set of 7, any set of 6, any set of 5, any set of 4, any set of 3, any set of 2, or any 1 of the amino acids C, R, K, S, T, H, D, E, N, Q, and M. For example, each X can independently be selected from the set of three amino acids C, R, and K. As another example, each X can independently be selected from the set of two amino acids C and R.

In some forms, a single one of the X can be C. In some forms, two of the X can be C. In some forms, two of the X can be R. In some forms, three of the X can be R. In some forms, four of the X can be R. As an example, the annexin 1-binding compound can comprise IFLLWQRCR (SEQ ID NO: 17), IFLLWQRCRR (SEQ ID NO: 19), IFLLWQRCRRR (SEQ ID NO: 18), or IFLLWQRCRRRR (SEQ ID NO:22).

The annexin 1-binding compound can comprise IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a C, R, K, S, T, H, D, E, N, Q, or M. In some forms, a single one of the X can be C. In some forms, two of the X can be C. In some forms, two of the X can be R. In some forms, three of the X can be R. In some forms, four of the X can be R.

The annexin 1-binding compound can comprise IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a C, R, or K. In some forms, a single one of the X can be C. In some forms, two of the X can be C. In some forms, two of the X can be R. In some forms, three of the X can be R. In some forms, four of the X can be R.

The annexin 1-binding compound can comprise IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a C or R. In some forms, a single one of the X can be C. In some forms, two of the X can be C. In some forms, two of the X can be R. In some forms, three of the X can be R. In some forms, four of the X can be R.

The annexin 1-binding compound can consist of IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a polar or charged amino acid. For example, each X can independently be selected from all, any set of 10, any set of 9, any set of 8, any set of 7, any set of 6, any set of 5, any set of 4, any set of 3, any set of 2, or any 1 of the amino acids C, R, K, S, T, H, D, E, N, Q, and M. For example, each X can independently be selected from the set of three amino acids C, R, and K. As another example, each X can independently be selected from the set of two amino acids C and R.

In some forms, a single one of the X can be C. In some forms, two of the X can be C. In some forms, two of the X can be R. In some forms, three of the X can be R. In some forms, four of the X can be R. As an example, the annexin 1-binding compound can consist of IFLLWQRCR (SEQ ID NO: 17), IFLLWQRCRR (SEQ ID NO: 19), IFLLWQRCRRR (SEQ ID NO: 18), or IFLLWQRCRRRR (SEQ ID NO:22).

The annexin 1-binding compound can consist of IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a C, R, K, S, T, H, D, E, N, Q, or M. In some forms, a single one of the X can be C. In some forms, two of the X can be C. In some forms, two of the X can be R. In some forms, three of the X can be R. In some forms, four of the X can be R.

The annexin 1-binding compound can consist of IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a C, R, or K. In some forms, a single one of the X can be C. In some forms, two of the X can be C. In some forms, two of the X can be R. In some forms, three of the X can be R. In some forms, four of the X can be R.

The annexin 1-binding compound can consist of IFLLWQRCX (amino acids 1 to 9 of SEQ ID NO:21), IFLLWQRCXX (amino acids 1 to 10 of SEQ ID NO:21), IFLLWQRCXXX (amino acids 1 to 11 of SEQ ID NO:21), IFLLWQRCXXXX (SEQ ID NO:21), wherein each X is independently a C or R. In some forms, a single one of the X can be C. In some forms, two of the X can be C. In some forms, two of the X can be R. In some forms, three of the X can be R. In some forms, four of the X can be R.

In some forms, the portion of the annexin 1-binding compound corresponding to the sequence IFLLWQRC (amino acids 1 to 8 of SEQ ID NO:21) can have one or more conservative amino acid substitutions in amino acids 1 to 8 of SEQ ID NO:21. In some forms, the portion of the annexin 1-binding compound corresponding to the sequence IFLLWQRC (amino acids 1 to 8 of SEQ ID NO:21) can have at least 55% sequence identity to the sequence IFLLWQRC (amino acids 1 to 8 of SEQ ID NO:21), wherein differences between the annexin 1-binding compound and IFLLWQRC (amino acids 1 to 8 of SEQ ID NO:21) consist of conservative amino acid substitutions. In some forms, the portion of the annexin 1-binding compound corresponding to the sequence IFLLWQRC (amino acids 1 to 8 of SEQ ID NO:21) can have at least 70% sequence identity to the sequence IFLLWQRC (amino acids 1 to 8 of SEQ ID NO:21). In some forms, the portion of the annexin 1-binding compound corresponding to the sequence IFLLWQRC (amino acids 1 to 8 of SEQ ID NO:21) can have at least 80% sequence identity to the sequence IFLLWQRC (amino acids 1 to 8 of SEQ ID NO:21). In some forms, the annexin 1-binding compound has at least 5 consecutive amino acids of the sequence IFLLWQRC (amino acids 1 to 8 of SEQ ID NO:21). In some forms, the annexin 1-binding compound has at least 6 consecutive amino acids of the sequence IFLLWQRCR (SEQ ID NO: 17), IFLLWQRCRR (SEQ ID NO: 19), IFLLWQRCRRR (SEQ ID NO: 18), or IFLLWQRCRRRR (SEQ ID NO:22).

The annexin 1-binding compound can comprise amino acids 1 to 8, 1 to 9, 1 to 10, 1 to 11, or 1 to 12 of SEQ ID NO:20 having none, one, or more conservative amino acid substitutions in amino acids 1 to 7. The annexin 1-binding compound can comprise amino acids 1 to 8, 1 to 9, 1 to 10, 1 to 11, or 1 to 12 of SEQ ID NO:20 and the portion of the annexin 1-binding compound corresponding to the sequence IFLLWQR (amino acids 1 to 7 of SEQ ID NO:20) can have at least 55% sequence identity to amino acids 1 to 7 of SEQ ID NO:20, wherein differences between the annexin 1-binding compound and amino acids 1 to 7 of SEQ ID NO:20 consist of conservative amino acid substitutions. The annexin 1-binding compound can comprise amino acids 1 to 8, 1 to 9, 1 to 10, 1 to 11, or 1 to 12 of SEQ ID NO:20 and the portion of the annexin 1-binding compound corresponding to the sequence IFLLWQR (amino acids 1 to 7 of SEQ ID NO:20) can have at least 70% sequence identity to amino acids 1 to 7 of SEQ ID NO:20. The annexin 1-binding compound can comprise amino acids 1 to 8, 1 to 9, 1 to 10, 1 to 11, or 1 to 12 of SEQ ID NO:20 and the portion of the annexin 1-binding compound corresponding to the sequence IFLLWQR (amino acids 1 to 7 of SEQ ID NO:20) can have at least 80% sequence identity to amino acids 1 to 7 of SEQ ID NO:20. The annexin 1-binding compound can comprise amino acids 1 to 8, 1 to 9, 1 to 10, 1 to 11, or 1 to 12 of SEQ ID NO:20. The annexin 1-binding compound can consist of amino acids 1 to 8, 1 to 9, 1 to 10, 1 to 11, or 1 to 12 of SEQ ID NO:20. The annexin 1-binding compound can comprise amino acid 8 or amino acids 8 to 9, 8 to 10, 8 to 11, or 8 to 12 of SEQ ID NO:20 and at least 5 consecutive amino acids of amino acids 1 to 7 of SEQ ID NO:20. The annexin 1-binding compound can comprise amino acids 1 to 8, 1 to 9, 1 to 10, 1 to 11, or 1 to 12 of SEQ ID NO:20 and at least 6 consecutive amino acids of amino acids 1 to 7 of SEQ ID NO:20.

The annexin 1-binding compound can comprise amino acids 1 to 9, 1 to 10, 1 to 11, or 1 to 12 of SEQ ID NO:21 having none, one, or more conservative amino acid substitutions in amino acids 1 to 8. The annexin 1-binding compound can comprise amino acids 1 to 9, 1 to 10, 1 to 11, or 1 to 12 of SEQ ID NO:21 and the portion of the annexin 1-binding compound corresponding to the sequence IFLLWQRC (amino acids 1 to 8 of SEQ ID NO:21) can have at least 55% sequence identity to amino acids 1 to 8 of SEQ ID NO:21, wherein differences between the annexin 1-binding compound and amino acids 1 to 8 of SEQ ID NO:21 consist of conservative amino acid substitutions. The annexin 1-binding compound can comprise amino acids 1 to 9, 1 to 10, 1 to 11, or 1 to 12 of SEQ ID NO:21 and the portion of the annexin 1-binding compound corresponding to the sequence IFLLWQRC (amino acids 1 to 8 of SEQ ID NO:21) can have at least 70% sequence identity to amino acids 1 to 7 of SEQ ID NO:21. The annexin 1-binding compound can comprise amino acids 1 to 9, 1 to 10, 1 to 11, or 1 to 12 of SEQ ID NO:21 and the portion of the annexin 1-binding compound corresponding to the sequence IFLLWQRC (amino acids 1 to 8 of SEQ ID NO:21) can have at least 80% sequence identity to amino acids 1 to 8 of SEQ ID NO:21. The annexin 1-binding compound can comprise amino acids 1 to 9, 1 to 10, 1 to 11, or 1 to 12 of SEQ ID NO:21. The annexin 1-binding compound can consist of amino acids 1 to 9, 1 to 10, 1 to 11, or 1 to 12 of SEQ ID NO:21. The annexin 1-binding compound can comprise amino acid 9 or amino acids 9 to 10, 9 to 11, or 9 to 12 of SEQ ID NO:21 and at least 5 consecutive amino acids of amino acids 1 to 8 of SEQ ID NO:21. The annexin 1-binding compound can comprise amino acid 9 or amino acids 9 to 10, 9 to 11, or 9 to 12 of SEQ ID NO:21 and at least 6 consecutive amino acids of amino acids 1 to 8 of SEQ ID NO:21.

The disclosed peptides and compositions can comprise any number of annexin 1-binding amino acid sequences. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more annexin 1-binding amino acid sequences. The peptide or composition can also comprise any number in between those numbers listed above.

The term "homing molecule" as used herein, means any molecule that selectively homes in vivo to specified target sites or tissues in preference to other tissue or tissues. Similarly, the term "homing peptide" or "homing peptidomimetic" means a peptide that selectively homes in vivo to specified target sites or tissues in preference to other tissue or normal tissue. It is understood that a homing molecule that selectively homes in vivo to, for example, tumors can home to all tumors or can exhibit preferential homing to one or a subset of tumor types.

By "selectively homes" it is meant that in vivo, the homing molecule binds preferentially to the target as compared to non-target. For example, the homing molecule can bind preferentially to tumor vasculature, as compared to non-tumoral tissue or non-vascular tissue. Such a homing molecule can selectively home, for example, to tumors. Selective homing to, for example, tumors generally is characterized by at least a two-fold greater localization within tumors (or other target), as compared to several tissue types of non-tumor tissue. A homing molecule can be characterized by 5-fold, 10-fold, 20-fold or more preferential localization to tumors (or other target) as compared to several or many tissue types of non-tumoral tissue, or as compared to-most or all non-tumoral tissue. Thus, it is understood that, in some cases, a homing molecule homes, in part, to one or more normal organs in addition to homing to the target tissue. Selective homing can also be referred to as targeting.

Many homing molecules and homing peptides home to the vasculature of the target tissue. However, for the sake of convenience homing is referred to in some places herein as homing to the tissue or cells associated with the vasculature to which the homing molecule or homing peptide may actually home. Thus, for example, a homing peptide that homes to tumor vasculature can be referred to herein as homing to tumor tissue or to tumor cells. By including or associating a homing molecule or homing peptide with, for example, a protein, peptide, amino acid sequence, or composition the protein, peptide, amino acid sequence, or composition can be targeted or can home to the target of the homing molecule or homing peptide. In this way, the protein, peptide, amino acid sequence, or composition can be said to home to the target of the homing molecule or homing peptide. For convenience and unless otherwise indicated, reference to homing of a protein, peptide, amino acid sequence, composition, etc. is intended to indicate that the protein, peptide, amino acid sequence, composition, etc. includes or is associated with an appropriate homing molecule or homing peptide.

The composition, peptide, or amino acid sequence can selectively home to a tumor. The composition, peptide, or amino acid sequence can selectively home to tumor vasculature. The composition, peptide, or amino acid sequence can selectively home to one or more particular types of tumor. The composition, peptide, or amino acid sequence can selectively home to the vasculature of one or more particular types of tumor. The composition, peptide, or amino acid sequence can selectively home to one or more particular stages of a tumor or cancer. The composition, peptide, or amino acid sequence can selectively home to the vasculature of one or more particular stages of a tumor or cancer. The composition, peptide, or amino acid sequence can selectively home to one or more particular stages of one or more particular types of tumor. The composition, peptide, or amino acid sequence can selectively home to the vasculature of one or more different stages of one or more particular types of tumor.

The disclosed annexin 1-binding compounds can include modified forms of annexin 1-binding compounds. The annexin 1-binding compounds can have any useful modification. For example, some modifications can stabilize the annexin 1-binding compound. For example, the disclosed annexin 1-binding amino acid sequences include methylated annexin 1-binding amino acid sequences.

As used herein, a "methylated derivative" of a protein, peptide, amino acid segment, amino acid sequence, etc. refers to a form of the protein, peptide, amino acid segment, amino acid sequence, etc. that is methylated. Unless the context indicates otherwise, reference to a methylated derivative of a protein, peptide, amino acid segment, amino acid sequence, etc. does not include any modification to the base protein, peptide, amino acid segment, amino acid sequence, etc. other than methylation. Methylated derivatives can also have other modifications, but such modifications generally will be noted. For example, conservative variants of an amino acid sequence would include conservative amino acid substitutions of the based amino acid sequence.

Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations. As another example, reference to a methylated derivative of an amino acid segment that includes amino acid substitutions would include methylated forms of the amino acid sequence and methylated forms of the amino acid sequence that include amino acid substitutions.

Peptides can have a variety of modifications. Modifications can be used to change or improve the properties of the peptides. For example, the disclosed peptides can be N-methylated, O-methylated, S-methylated, C-methylated, or a combination at one or more amino acids.

The amino and/or carboxy termini of the disclosed peptides can be modified. Amino terminus modifications include methylation (e.g., —NHCH$_3$ or —N(CH$_3$)$_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the disclosed peptides, or incorporate a desamino or descarboxy residue at the termini of the peptide, so that there is no terminal amino or carboxyl group, to decrease susceptibility to proteases or to restrict the conformation of the peptide. C-terminal functional groups of the disclosed peptides include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower (C$_{1-6}$) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods [e.g., as described in Hruby, et al. (1990) Biochem J. 268:249-262].

The disclosed peptides also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis [See, Morgan and Gainor (1989) Ann. Rep. Med. Chem. 24:243-252]. These techniques include, but are not limited to, replacing the peptide backbone with a backbone composed of phosphonates, amidates, carbamates, sulfonamides, secondary amines, and N-methylamino acids.

All of the disclosed annexin 1-binding compounds, peptides, amino acid sequences, moieties, therapeutic agents, etc. can be used as described herein. Every generic or particular annexin 1-binding compounds, peptides, amino acid sequences, moieties, therapeutic agents, etc. described herein can be specifically included or excluded, either individually or in groups, in or from any set of annexin 1-binding compounds, peptides, amino acid sequences, moieties, therapeutic agents, etc. and/or in or from any use. For example, the I-peptide and/or sequence variants of the I-peptide can be specifically excluded from any set of, for example, annexin 1-binding compounds, peptides, amino acid sequences, etc. and/or from any use. As another example, geldanamycin can be specifically excluded from any set of, for example, moieties, therapeutic agents, etc. and/or from any use. As another example, IF7 (SEQ ID NO:2) and/or sequence variants of IF7 can be specifically excluded from any set of, for example, annexin 1-binding compounds, peptides, amino acid sequences, etc. and/or from any use. Every generic or particular annexin 1-binding compounds, peptides, amino acid sequences, moieties, therapeutic agents, etc. described herein can be specifically included or excluded, either individually or in groups, in or from any set of annexin 1-binding compounds, peptides, amino acid sequences, moieties, therapeutic agents, etc. as described herein and/or in or from any use as described herein.

B. Peptides and Amino Acid Sequences

In some forms, the disclosed peptides and amino acid sequences can be or include a peptide, peptidomimetic, and/or amino acid segment. Unless the context indicates otherwise, reference herein to "peptide" is intended to refer also to amino acid sequences, which can form a part of, or constitute an entire, peptide. The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides and amino acid sequences can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

The disclosed amino acid sequences can have, for example, a relatively short length of less than six, seven, eight, nine, ten, 12, 15, 20, 25, 30, 35 or 40 residues. The disclosed amino acid sequences also can be useful in the context of a significantly longer sequence. Thus, the amino acid sequences can have, for example, a length of up to 50, 100, 150, 200, 250, 300, 400, 500, 1000 or 2000 residues. In particular embodiments, an amino acid sequence can have a length of at least 10, 20, 30, 40, 50, 60, 70, 80, 90, 100 or 200 residues. In further embodiments, an amino acid sequence can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As this specification discusses various proteins, protein sequences, peptides, peptides sequences, and amino acid sequences, it is understood that the nucleic acids that can encode those sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —$CH$=$CH$— (cis and trans), —$COCH_2$—, —$CH(OH)CH_2$—, and —$CH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, —$CH_2CH_2$—); Spatola et al. Life Sci 38:1243-1249 (1986) (—$CH_2S$—); Hann J. Chem. Soc Perkin Trans. I 307-314 (1982) (—$CH$=$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)CH_2$—); Holladay et al. Tetrahedron. Lett 24:4401-4404 (1983) (—$CH(OH)CH_2$—); and Hruby Life Sci 31:189-199 (1982) (—$CH_2$—$S$—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Also disclosed are bifunctional peptides, which contain, for example, an annexin1-binding peptide fused to a second peptide having a separate function. Such bifunctional peptides have at least two functions conferred by different portions of the full-length molecule and can, for example, display anti-angiogenic activity or pro-apoptotic activity in addition to tumor homing.

Also disclosed are isolated multivalent peptides that include at least two subsequences each independently containing a peptide or amino acid sequence (for example, the amino acid sequence SEQ ID NO: 2, or a conservative variant or peptidomimetic thereof). The multivalent peptide can have, for example, at least three, at least five or at least ten of such subsequences each independently containing a peptide. In particular embodiments, the multivalent peptide can have two, three, four, five, six, seven, eight, nine, ten, fifteen or twenty identical or non-identical subsequences. This is in addition to the multiple annexin 1-binding amino acid sequences that can comprise the disclosed compositions. In a further embodiment, the multivalent peptide can contain identical subsequences, such as repeats of SEQ ID NO: 2. In a further embodiment, the multivalent peptide contains contiguous identical or non-identical subsequences, which are not separated by any intervening amino acids.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α.-dialkylglycine or α-aminocycloalkane carboxylic acid; an $N^α$—$C^α$ cyclized amino acid; an N$^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—C$^E$ or C$^\alpha$—C$^\Delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverse modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively interacting with cancerous cells.

C. Moieties

The compositions disclosed herein can comprise one or more moieties. For example, moieties can be molecules, conjugates, associations, compositions, and mixtures. Examples of moieties include, but are not limited to, anti-angiogenic agents, pro-angiogenic agents, cancer chemotherapeutic agents, cytotoxic agents, anti-inflammatory agents, anti-arthritic agents, polypeptides, nucleic acid molecules, small molecules, nanoparticles, and microparticles. At least one of the moieties can be a therapeutic agent. Examples of therapeutic agents are paclitaxel and docetaxel. At least one of the moieties can be a detectable agent. Moieties that are peptides or amino acid sequences can be referred to as moiety peptides or moiety amino acid sequences, respectively.

As used herein, the term "moiety" is used broadly to mean a physical, chemical, or biological material that generally imparts a biologically useful function to a linked or conjugated molecule. As disclosed herein, the properties of the moiety can also be found in a peptide or amino acid sequence, or both the peptide or amino acid sequence and the moiety can share one of the traits disclosed herein. For example, the peptide or amino acid sequence can comprise a detectable agent, while the moiety can comprise a therapeutic agent. This also applies for the annexin 1-binding compound, which can also comprise one or more of the properties of moieties as disclosed herein. The description of therapeutic and detectable agents which follows is intended to apply to any of moieties, peptides, amino acid sequences, or annexin 1-binding compounds. Thus, for example, moieties can be conjugated to, coupled to, or can be part of the disclosed peptides, amino acid sequences, annexin 1-binding compounds, compositions, or conjugates of peptides, amino acid sequences and annexin 1-binding compounds.

A moiety can be any natural or nonnatural material including, without limitation, a biological material, such as a cell, phage or other virus; an organic chemical such as a small molecule; a nanoparticle, a radionuclide; a nucleic acid molecule or oligonucleotide; a polypeptide; or a peptide. For example, moieties can affect the target, such as moieties with therapeutic effect, or can facilitate detection, visualization or imaging of the target, such as fluorescent molecule or radionuclides. Useful moieties include, but are not limited to, therapeutic agents such as cancer chemotherapeutic agents, cytotoxic agents, pro-apoptotic agents, and anti-angiogenic agents; detectable labels and imaging agents; and tags or other insoluble supports. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a composition.

Components of the disclosed compositions can be combined, linked and/or coupled in any suitable manner. For example, moieties and other molecules can be associated covalently or noncovalently, directly or indirectly, with or without a linker moiety.

1. Therapeutic Agents

The moiety can be a therapeutic agent. As used herein, the term "therapeutic agent" means a molecule which has one or more biological activities in a normal or pathologic tissue. A variety of therapeutic agents can be used as a moiety. The therapeutic agent can comprise a compound or composition for treating cancer. The therapeutic agent can comprise a compound or composition to induce programmed cell death or apoptosis. For example, the therapeutic agent can be (KLAKLAK)$_2$ or $_D$(KLAKLAK)$_2$ (SEQ ID NO:24).

In some embodiments, the therapeutic agent can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite such as methotrexate; a platinum agent such as cisplatin, carboplatin, or oxaliplatin; a steroid; an antibiotic such as adriamycin; a ifosfamide; or a selective estrogen receptor modulator; an antibody such as trastuzumab; paclitaxel such as Abraxane.

Taxanes are chemotherapeutic agents useful with the compositions disclosed herein. Useful taxanes include, without limitation, docetaxel (Taxotere; sanofi-aventis; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

A cancer chemotherapeutic agent useful with the compositions disclosed herein also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, Nature Biotechnology 15:510 (1997); Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan, ifosfamide, or chlorambucil also can be a useful cancer chemotherapeutic agent. Similarly, a vinca alkaloid such as vindesine, vinblastine or vinorelbine; or an antimetabolite such as 5-fluorouracil, 5-fluorouridine, methotrexate, or a derivative thereof can be a useful cancer chemotherapeutic agent.

A platinum agent also can be a useful cancer chemotherapeutic agent. Such a platinum agent can be, for example, cisplatin, carboplatin, or oxaliplatin as described, for example, in Crown, Seminars in Oncol. 28:28-37 (2001). Other useful cancer chemotherapeutic agents include, without limitation, mitomycin-C, adriamycin (doxorubicin), and ansamycins.

A cancer chemotherapeutic agent useful for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a composition for treatment of breast cancer (Fisher et al., J. Natl. Cancer Instit. 90:1371-1388 (1998)).

The therapeutic agent can be an antibody such as a humanized monoclonal antibody. As an example, the anti-epidermal growth factor receptor 2 (HER2) antibody, trastuzumab (Herceptin; Genentech, South San Francisco, Calif.) can be a therapeutic agent useful for treating HER2/neu overexpressing breast cancers (White et al., Annu Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In some forms, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide." Examples of pro-apoptotic therapeutic agents are (KLAKLAK)$_2$ or $_D$(KLAKLAK)$_2$ (SEQ ID NO:24) (del Rio, 2001; Ellerby, 1999). $_D$(KLAKLAK)$_2$ (SEQ ID NO:24) refers to the sequence KLAKLAKKLAKLAK (SEQ ID NO:24) made with D amino acids. These peptides can be used in any of the disclosed compositions and combined with any of the disclosed peptides or annexin 1-binding compounds. Examples of such compositions include IFLLWQR-KLAKLAKKLAKLAK (SEQ ID NOs:2 and 24), IFLLWQRC-KLAKLAKKLAKLAK (SEQ ID NOs:14 and 24), IFLLWQRCR-KLAKLAKKLAKLAK (SEQ ID NOs:17 and 24), IFLLWQRCRR-KLAKLAKKLAKLAK (SEQ ID NOs:19 and 24), IFLLWQRCRRR-KLAKLAKKLAKLAK (SEQ ID NOs: 18 and 24), or IFLLWQRCRRRR-KLAKLAKKLAKLAK (SEQ ID NOs:22 and 24).

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Vascular endothelial growth factor (VEGF) has been shown to be important for angiogenesis in many types of cancer, including breast cancer angiogenesis in vivo (Borgstrom et al., Anticancer Res. 19:4213-4214 (1999)). The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., Cell Biol. 19:431-444 (1995); Folkman and Shing, J. Biol. Chem. 267:10931-10934 (1992)) or an angiogenic factor such as angiopoietin-1, a factor that signals through the endothelial cell-specific Tie2 receptor tyrosine kinase (Davis et al., Cell 87:1161-1169 (1996); and Suri et al., Cell 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of antithrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., Cell 79:315-328 (1994)); O'Reilly et al., Cell 88:277-285 (1997); Homandberg et al., Am. J. Path. 120:327-332 (1985); Homandberg et-al., Biochim. Biophys. Acta 874:61-71 (1986); and O'Reilly et al., Science 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

Some other examples of useful therapeutic agents include nitrogen mustards, nitrosoureas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel (TAXOTERE®, Rhone-Poulenc Rorer, Antony, France), Doxil, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel (TAXOL®, Bristol-Myers Squibb Oncology, Princeton, N.J.), Pamidronate, Pentostatin, Phenesterine, Plicamycin, Prednimustine, Procarbazine, Rituximab, Steroids, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, triethylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; antimetabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotepa; taxoids, e.g., Paclitaxel and Doxetaxel; Gemcitabine; 6-thioguanine; Mercaptopurine; Methotrexate; platinum analogs such as Cisplatin, Carboplatin, and Oxaliplatin; etoposide (VP-16); Ifosfamide; Mitomycin C; Mitoxantrone; Vinblastine; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above. Useful therapeutic agents include, for example, doxorubicin, Herceptin, and liposomal doxorubicin.

The therapeutic agents can also comprise a boron containing compound. Boron containing compounds have received increasing attention as therapeutic agents over the past few years as technology in organic synthesis has expanded to include this atom (Boron Therapeutics on the horizon, Groziak, M. P.; American Journal of Therapeutics (2001) 8, 321-328). The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides (Organic boron compounds as herbicides. Barnsley, G. E.; Eaton, J. K.; Airs, R. S.; (1957), DE 1016978 19571003), boron neutron capture therapy (Molecular Design and Synthesis of B-10 Carriers for Neutron Capture Therapy. Yamamoto, Y.; Pure Appl. Chem., (1991) 63, 423-426), serine protease inhibition (Borinic acid inhibitors as probes of the factors involved in binding at the active sites of subtilisin Carlsberg and α-chymotrypsin. Simpelkamp, J.; Jones, J. B.; Bioorganic & Medicinal Chemistry Letters, (1992), 2 (11), 1391-4; Design, Synthesis and Biological Evaluation of Selective Boron-containing Thrombin Inhibitors. Weinand, A.; Ehrhardt, C.; Metternich, R.; Tapparelli, C.; Bioorganic and Medicinal Chemistry, (1999), 7, 1295-1307), acetylcholinesterase inhibition (New, specific and reversible bifunctional alkylborinic acid inhibitor of acetylcholinesterase. Koehler, K. A.; Hess, G. P.; Biochemistry (1974), 13, 5345-50) and as antibacterial agents (Boron-Containing Antibacterial Agents Effects on Growth and Morphology of Bacteria Under Various Culture Conditions. Bailey, P. J.; Cousins, G.; Snow, G. A.; and White, A. J.; Antimicrobial Agents and Chemotherapy, (1980), 17, 549-553). The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity (Preparation of diarylborinic acid esters as DNA methyl transferase inhibitors. Benkovic, S. J.; Shapiro, L.; Baker, S. J.; Wahnon, D. C.; Wall, M.; Shier, V. K.; Scott, C. P.; Baboval, J.; PCT Int. Appl. (2002), WO 2002044184).

It is understood by one skilled in the art of medicinal oncology that these and other agents are useful therapeutic agents, which can be used separately or together in the disclosed compositions and methods. Thus, it is understood that the compositions disclosed herein can contain one or more of such therapeutic agents and that additional components can be included as part of the composition, if desired. As a non-limiting example, it can be desirable in some cases to utilize an oligopeptide spacer between the disclosed peptides, amino acid sequences, and annexin 1-binding compounds and the therapeutic agent (Fitzpatrick and Garnett, Anticancer Drug Des. 10:1-9 (1995)).

2. Detectable Agents

The moiety in the disclosed compositions can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any moiety or molecule that facilitates detection, either directly or indirectly, preferably by a non-invasive and/or in vivo visualization technique. For example, a detectable agent can be detectable by any known imaging techniques, including, for example, a radiological technique, a magnetic resonance technique, or an ultrasound technique. Detectable agents can include, for example, a contrast agent. The contrast agent can be, for example, Feridex. The contrasting agent can be, for example, ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, iron oxide and Gd can be used as a non-radioactive detectable agent in certain embodiments. Detectable agents can also include radioactive isotopes, enzymes, fluorophores, and quantum dots (Qdot®). For example, the detection moiety can be an enzyme, biotin, metal, or epitope tag. Other known or newly discovered detectable markers are contemplated for use with the provided compositions. In some embodiments, for instance, the detectable agent comprises a barium compound, e.g., barium sulfate.

The detectable agent can be one or more imaging agents. Examples of imaging agents include radiologic contrast agent, such as diatrizoic acid sodium salt dihydrate, iodine, and barium sulfate, a fluorescing imaging agent, such as Lissamine Rhodamine PE, a fluorescent or non-fluorescent stain or dye, for example, that can impart a visible color or that reflects a characteristic spectrum of electromagnetic radiation at visible or other wavelengths, for example, infrared or ultraviolet, such as Rhodamine, a radioisotope, a positron-emitting isotope, such as $^{18}$F or $^{124}$I (although the short half-life of a positron-emitting isotope may impose some limitations), a metal, a ferromagnetic compound, a paramagnetic compound, such as gadolinium, a superparamagnetic compound, such as iron oxide, and a diamagnetic compound, such as barium sulfate. Imaging agents can be selected to optimize the usefulness of an image produced by a chosen imaging technology. For example, the imaging agent can be selected to enhance the contrast between a feature of interest, such as a gastrointestinal polyp, and normal gastrointestinal tissue. Imaging can be accomplished using any suitable imaging techniques such as X-Ray, computed tomography (CT), MRI, Positron Emission Tomography (PET) or SPECT. In some forms, the disclosed components, compounds, and compositions can be coupled to a nuclear medicine imaging agent such as Indium-III or Technetium-99, to PET imaging agents, or to MRI imaging agents such as nanoparticles.

Examples of imaging techniques include magnetic resonance imaging (MRI), computerized tomography (CT), single photon emission computerized tomography (SPECT), and positron emission tomography (PET). Imaging agents generally can be classified as either being diagnostic or therapeutic in their application. Because of radiation's damaging effect on tissues, it is useful to target the biodistribution of radiopharmaceuticals as accurately as possible. PET can use imaging agents labeled with, for example, the positron-emitters such as $^{18}$F, $^{11}$C, $^{13}$N and $^{15}$O, $^{75}$Br, $^{76}$Br and $^{124}$I. SPECT can use imaging agents labeled with, for example, the single-photon-emitters such as $^{201}$Tl, $^{99}$Tc, $^{123}$I, and $^{131}$I.

Glucose-based and amino acid-based compounds can be used as imaging agents. Amino acid-based compounds are more useful in analyzing tumor cells, due to their faster uptake and incorporation into protein synthesis. Of the amino acid-based compounds, $^{11}$C- and $^{18}$F-containing compounds have been used with success. $^{11}$C-containing radiolabeled amino acids suitable for imaging include, for example, L-[1-$^{11}$C]leucine (Keen et al. J. Cereb. Blood Flow Metab. 1989 (9):429-45), L[1-$^{11}$C]tyrosine (Wiesel et al. J. Nucl. Med. 1991 (32):2041-49), L[methyl-$^{11}$C]methionine (Comar et al. Eur. J. Nucl. Med. 1976 (1): 11-14) and L[1-$^{11}$C]methionine (Bolster et al. Appl. Radiat. Isot. 1986 (37):1069-70).

PET involves the detection of gamma rays in the form of annihilation photons from short-lived positron emitting radioactive isotopes including, but not limited to, $^{18}$F with a half-life of approximately 110 minutes, $^{11}$C with a half-life of approximately 20 minutes, $^{13}$N with a half-life of approximately 10 minutes and $^{15}$O with a half-life of approximately 2 minutes, using the coincidence method. For PET imaging studies, compounds such as [$^{11}$C]meta-hydroxyephedrine (HED) and 2-[$^{18}$F]fluoro-2-deoxy-D-glucose (FDG) can be used. SPECT can use longer-lived isotopes including, but not limited to, $^{99m}$Tc with a half-life of approximately 6 hours and $^{201}$Tl with a half-life of approximately 74 hours. Radio-iodinated meta-iodobenzylguanidine (MIBG) is a radiotracing agent that can be used in nuclear medicine imaging studies.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferromagnetic, paramagnetic, and/or superparamagnetic species), molecules which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include proton-emitting molecules, radiopaque molecules, and/or radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 am), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, 1-125 and 1-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011,686); positron emitters, such as Cu-64, C-11, and 0-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or Tl-201.

The use of Technitium-99m (Tc-99m) is preferable and has been described in other applications, for example, see U.S. Pat. No. 4,418,052 and U.S. Pat. No. 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling radioisotopes suitable for detection to the disclosed components and compositions. Coupling can be, for example, via a chelating agent such as diethylenetriaminepentaacetic acid (DTPA), 4,7,10-tetraazacyclododecane-N-,N',N'',N'''-tetraacetic acid (DOTA) and/or metallothionein, any of which can be covalently attached to the disclosed components, compounds, and compositions. In some embodiments, an aqueous mixture of technetium-99m, a reducing agent, and a water-soluble ligand can be prepared and then allowed to react with a disclosed component, compound, or composition. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(II), neodymium(III), samarium(III) and ytterbium(III), as well as gadolinium(III), terbium(III), dysoprosium(III), holmium (III), and erbium(II). Some preferred embodiments use atoms with strong magnetic moments, e.g., gadolinium(III).

In some embodiments, compositions comprising magnetic detectable agents can be prepared by coupling the disclosed components, compounds, and compositions with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the disclosed components, compounds, and compositions in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In preferred embodiments, the detectable agent can be coupled to the composition in such a way so as not to interfere with the ability of the disclosed compositions, peptides, amino acid sequences, and annexin 1-binding compounds to interact with annexin 1. In some embodiments, the detectable agent can be chemically bound to the composition, peptide, amino acid sequence, or annexin 1-binding compound. In some embodiments, the detectable agent can be chemically bound to a moiety that is itself chemically bound to the composition, peptide, amino acid sequence, or annexin 1-binding compound, indirectly linking the imaging and the disclosed components, compounds, and compositions.

The moiety can also include poly-L-lysine and related molecules. For example, moieties can include any of the moieties disclosed herein with the addition of poly-L-lysine conjugated or coupled to the moiety. For example, the moiety can be FITC-poly-L-lysine or Alexa488-poly-L-lysine. Examples of compositions with such moieties include IF7C(RR)-conjugated FITC-poly-L-lysine and IF7C(RR)-conjugated Alexa488-poly-L-lysine.

D. Linkages, Linkers, and Cleavable Bonds

The disclosed annexin 1-binding compounds (such as the disclosed peptides and amino acid sequences) and moieties (or other components of the disclosed compositions) can be linked in any useful way. For example, annexin 1-binding compounds and moieties can be covalently coupled (directly or indirectly), noncovalently coupled (directly or indirectly), or both. Covalent coupling is useful. Direct coupling can be via a covalent bond between the annexin 1-binding compound and the moiety. The covalent bond in such cases can be considered the linkage between the annexin 1-binding compound and the moiety. Indirect coupling can be via one or more intervening molecules or components. Useful indirect coupling can be via a linker. The linker, any bond in the linker that couples the annexin 1-binding compound and the moiety, the bond between the annexi 1-binding compound and the linker, and/or the bond between the moiety and the linker can be considered a linkage. Any suitable linker can be used. For example, the linker can be an oligomer, such as a peptide or peptide mimetic.

The linker can contain or linkage can be a cleavable bond. A cleavable bond can be useful for freeing the moiety at the site of targeting, for example. The cleavable bond can be cleaved in any suitable way. For example, the cleavable bond can be cleaved enzymatically or non-enzymatically. For enzymatic cleavage, the cleaving enzyme can be supplied or can be present at a site where the composition is delivered, homes, travels or accumulates. For example, the enzyme can be present in proximity to a cell to which the composition is delivered, homes, travels, or accumulates. For non-enzymatic cleavage, the composition can be brought into contact with a cleaving agent, can be placed in cleaving conditions, or both. A cleaving agent is any substance that can mediate or stimulate cleavage of the cleavable bond. A non-enzymatic cleaving agent is any cleaving agent except enzymes. Cleaving conditions can be any solution or environmental conditions that can mediate or stimulate cleavage of the cleavable bond. For example, some labile bonds can be cleaved in acid conditions, alkaline conditions, in the presence of a reactive group, etc. Non-enzymatic cleaving conditions are any cleaving conditions except the presence of enzymes. Non-agent cleaving conditions are any cleaving conditions except the presence of cleaving agents.

A "protease-cleavable bond" refers to a cleavable bond that can be cleaved by a protease. Useful proteases include proteases that may be present at the location where the disclosed compositions are delivered, target, home, etc. Examples of useful proteases include, for example, serine proteases (including, for example, plasmin and pasminogen activators), proprotein convertases (see, for example, Duckert et al., Prediction of proprotein convertase cleavage sites Protein engineering Design and Selection 17(1): 107-112 (2004)), furins, and carboxypeptidases. Serine proteases are particularly useful for compositions targeted to cancer cells and tumors. Examples of enzymes that cleave on the C terminal side of basic residues include Arg-C protease (which cleaves on the C terminal side of arginine residues; Keil, Specificity of Proteolysis (Springer-Verlag, Berlin-Heidelberg-New York (1992)), clostripain (which cleaves on the C terminal side of arginine residues; Keil, 1992), enterokinase (which cleaves after the sequence -Asp-Asp-Asp-Asp-Lys-; SEQ ID NO:23), Factor Xa (which cleaves after the sequence -Gly-Arg-; Fujikawa et al., Activation of bovine factor X (Stuart factor): conversion of factor Xa alpha to factor Xa beta, Proc. Natl. Acad. Sci. 72: 3359-3363 (1975)), Lys-C (which cleaves on the C terminal side of lysine residues; Keil, 1992), thrombin (which cleaves on the C terminal side of arginine residues; Keil, 1992), trypsin (which cleaves on the C terminal side of arginine and lysine residues; Keil, 1992), serine proteases, proprotein convertases (such as PC1, PC2, PC3, PC4, PC5, PC6, PC7, PC8, furin, Pace, PACE4, Site 1 protease, SIP, SKI, NARC-1, PCSK1, PCSK2, PCSK3, PCSK4, PCSK5, PCSK6, PCSK7, PCSK8, and PCSK9), plasmin, and plasminogen activators. Examples of enzymes that recognize sequence on the C terminal side of their cleavage site include Asp-N endopeptidase (which cleaves on the N terminal side of aspartic acid; Keil, 1992) and carboxypeptidases such as carboxypeptidase A (which cleaves C-terminal residues except proline, lysine and arginine).

Examples of proteases are also described in Hook, Proteolytic and cellular mechanisms in prohormone and proprotein processing, RG Landes Company, Austin, Tex., USA (1998); Hooper et al., Biochem. J. 321: 265-279 (1997); Werb, Cell 91: 439-442 (1997); Wolfsberg et al., J. Cell Biol. 131: 275-278 (1995); Murakami and Etlinger, Biochem. Biophys. Res. Comm. 146: 1249-1259 (1987); Berg et al., Biochem. J. 307: 313-326 (1995); Smyth and Trapani, Immunology Today 16: 202-206 (1995); Talanian et al., J. Biol. Chem. 272: 9677-9682 (1997); and Thornberry et al., J. Biol. Chem. 272: 17907-17911 (1997).

An "esterase-cleavable bond" refers to a cleavable bond that can be cleaved by a protease. Useful esterases include esterases that may be present at the location where the disclosed compositions are delivered, target, home, etc.

E. Pharmaceutical Compositions and Carriers

The disclosed compositions can be administered in vivo either alone or in a pharmaceutically acceptable carrier. By "pharmaceutically acceptable" is meant a material that is not biologically or otherwise undesirable, i.e., the material can be administered to a subject, along with the composition disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

1. Pharmaceutically Acceptable Carriers

The compositions disclosed herein can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

2. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohorns, nano-onions, nanorods, nanoropes and quantum dots.

Microspheres (or microbubbles) can also be used with the methods disclosed herein. Microspheres containing chromophores have been utilized in an extensive variety of applications. The monodispersity of the microspheres can be important.

Nanoparticles, such as, for example, metal nanoparticles, metal oxide nanoparticles, or semiconductor nanocrystals can be incorporated into microspheres. The nanoparticle can be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897, 945 and 6,759,199, each of which is incorporated by reference in its entirety.

3. Liposomes

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 µm. These MLVs were first described by Bangham, et al., J Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 µm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes is oligolamellar vesicles ("OLVs"), which have a large center compartment surrounded by several peripheral lipid layers. These vesicles, having a diameter of 2-15 µm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

F. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, peptides, etc., are also disclosed. Thus, the products produced using the molecular modeling approaches that involve the disclosed compositions are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

G. Compositions with Similar Functions

It is understood that the compositions disclosed herein have certain functions, such as binding to annexin 1 or homing to tumor vasculature. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

H. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits can include the compositions disclosed herein.

I. Mixtures

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

J. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

K. Computer Readable Media

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

L. Peptide Synthesis

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NO:2, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Methods

Disclosed herein are methods comprising administering to a subject the disclosed compositions, annexin 1-binding compounds, annexin 1-binding amino acid sequences, peptides, or amino acid sequences. The compositions, annexin 1-binding compounds, annexin 1-binding amino acid sequences, peptides, and amino acid sequences can selectively home to tumor vasculature. The composition can accumulate in tumor vasculature. Some forms of the method comprise administering to a subject the composition, annexin 1-binding compound, annexin 1-binding amino acid sequence, peptide, or amino acid sequence disclosed herein, wherein the composition, annexin 1-binding compound, annexin 1-binding amino acid sequence, peptide, or amino acid sequence selectively homes to tumor vasculature, wherein the composition, annexin 1-binding compound, annexin 1-binding amino acid sequence, peptide, or amino acid sequence accumulates in tumor vasculature. The composition, annexin 1-binding compound, annexin 1-binding amino acid sequence, peptide, or amino acid sequence can selectively home to tumor vasculature.

Disclosed are methods comprising administering to a subject a composition comprising a moiety and a peptide comprising an amino acid sequence that can bind to a carbohydrate receptor on a cell. Also disclosed are methods of targeting a tumor cell in a subject comprising administering to the subject a peptide comprising an amino acid sequence that can bind to a carbohydrate receptor on a cell. Also disclosed are methods of targeting a tumor cell in a subject comprising administering to the subject a composition comprising a moiety and a peptide comprising an amino acid sequence that can bind to a carbohydrate receptor on a cell. Also disclosed are methods comprising administering to the subject a composition comprising a peptide comprising an amino acid sequence that can bind to a carbohydrate receptor on a cell and detecting the composition in the subject.

In one example, the composition can have a therapeutic effect. This effect can be enhanced by the delivery of a therapeutic agent to the site of the tumor.

The therapeutic effect can be a slowing in the increase of or a reduction of tumor burden. This slowing in the increase of, or reduction in the tumor burden, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in the increase of, or reduction in the tumor burden of, compared with a non-treated tumor, or a tumor treated by a different method.

The therapeutic effect can also be a reduction or blocking of blood circulation in a tumor. This reduction or blocking of blood circulation in a tumor, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in effective blocking of blood circulation in a tumor, compared with a non-treated tumor, or a tumor treated by a different method.

The disclosed compositions can be used to treat any disease where annexin 1 is present in higher than normal amounts such as cancers. A non-limiting list of different types of cancers that can be treated includes lymphomas (Hodgkins and non-Hodgkins), carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, gastric cancer, head and neck carcinoma, large bowel cancer, hematopoietic cancers; testicular cancer; colon and rectal cancers, prostatic cancer, or pancreatic cancer.

The disclosed compositions can also be administered following decoy particle pretreatment to reduce uptake of the compositions by reticuloendothelial system (RES) tissues. Such decoy particle pretreatment can prolong the blood half-life of the particles and increases tumor targeting.

The method can further comprise, following administering, detecting the disclosed peptides and compositions. The disclosed peptides and compositions can be detected by fluorescence, CT scan, PET or MRI. The disclosed peptides and compositions can be detected by fluorescence. The disclosed peptides and compositions can conjugate with tumor vasculature or a tumor in a subject.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

Highly Efficient Drug Delivery Targeted to Malignant Tumors by Carbohydrate Mimicry Peptide IF7

1. Introduction

Technical advances in genomics and proteomics together with automated chemical synthesis of DNA and proteins have greatly contributed to progress in biomedicine. By contrast, understanding the role of carbohydrates has lagged behind due to lack of advanced technologies: currently, recombinant or amplifiable carbohydrates can not be produced nor can complex carbohydrates automatically be chemically synthesized. Consequently, carbohydrate-based drug discovery has been largely unexplored despite the fact that cancer malignancy is closely associated with carbohydrate structures found on the tumor cell surface (S. Hakomori. Glycosylation defining cancer malignancy: new wine in an old bottle. Proc Natl Acad Sci USA 99:10231-10233 (2002); S, Nakamori, et al. Increased expression of sialyl Lewisx antigen correlates with poor survival in patients with colorectal carcinoma: clinicopathological and immunohistochemical study. Cancer Res 53:3632-3637 (1993)). To move beyond this dilemma, peptide-displaying phage technology and identified carbohydrate mimicry peptides have been employed (M. N. Fukuda, et al. A peptide mimic of E-selectin ligand inhibits sialyl Lewis X-dependent lung colonization of tumor cells. Cancer Res 60:450-456 (2000); M. N. Fukuda. Screening of peptide-displaying phage libraries to identify short peptides mimicking carbohydrates. Methods Enzymol 416:51-60 (2006); T. Taki, et al. A new approach for drug discovery from glycobiology and phage-displayed peptide library technology. Biochim Biophys Acta 1780:497-503 (2008); J. K. Scott, D. Loganathan, R. B. Easley, X. Gong, I. J. Goldstein. A family of concanavalin A-binding peptides from a hexapeptide epitope library. Proc Natl Acad Sci USA 89:5398-5402 (1992)). For example, I-peptide, or IELLQAR, was identified as a selectin ligand mimic, and when injected intravenously into mice, synthetic I-peptide inhibited carbohydrate-dependent cancer cell colonization to the lung (M. N. Fukuda, et al. A peptide mimic of E-selectin ligand inhibits sialyl Lewis X-dependent lung colonization of tumor cells. Cancer Res 60:450-456 (2000); J. Zhang, et al. Sialyl Lewis X-dependent lung colonization of B16 melanoma cells through a selectin-like endothelial receptor distinct from E- or P-selectin. Cancer Res 62:4194-4198 (2002)).

When I-peptide was loaded into apoptosis-inducing liposomes (R. De Maria, et al. Requirement for GD3 ganglioside in CD95- and ceramide-induced apoptosis. Science 277: 1652-1655 (1997)) and injected intravenously into mice without tumors, 1-peptide targeted those liposomes to lung endothelial cells, which display potential carbohydrate-dependent sites allowing cancer cell colonization (S. Hatakeyama et al. Identification of mRNA splicing factors as the endothelial receptor for carbohydrate-dependent lung colonization of cancer cells. Proc Natl Acad Sci USA 106:3095-3100 (2009)). Mice treated with I-peptide-loaded liposomes did not show carbohydrate-dependent cancer colonization of the lung. Significantly, when I-peptide-loaded liposomes were injected into mice bearing subcutaneously produced B16 tumors, the size of primary tumor was reduced. Antitumor activity promoted by I-peptide can be mediated by annexin 1 (Anxa1), as I-peptide bound to an annexin 1 (Anxa1) fragment (S. Hatakeyama et al.

Identification of mRNA splicing factors as the endothelial receptor for carbohydrate-dependent lung colonization of cancer cells. Proc Natl Acad Sci USA 106:3095-3100 (2009)). Extensive subtractive proteomics identified Anxa1 as a specific tumor endothelial cell surface marker (Oh et al. Subtractive proteomic mapping of the endothelial surface in lung and solid tumours for tissue-specific therapy. Nature 429:629-635 (2004)). These preliminary observations together with carbohydrate binding activity by annexin family proteins (R. Hannon et al. Aberrant inflammation and resistance to glucocorticoids in annexin 1−/− mouse. Faseb J 17:253-255 (2003); H. A. Lehr et al. Dorsal skinfold chamber technique for intravital microscopy in nude mice. Am J Pathol 143:1055-1062 (1993)) prompted development of a tumor vasculature-specific targeting vehicle utilizing a carbohydrate-mimicry peptide. Herein, Anxa1-binding carbohydrate mimicry peptide, designated IF7, has been identified as a highly efficient tumor-targeting vehicle for anti-cancer drugs.

2. Results i. Relevance of Anxa1 as a Tumor Vasculature Marker

Figure 1B:
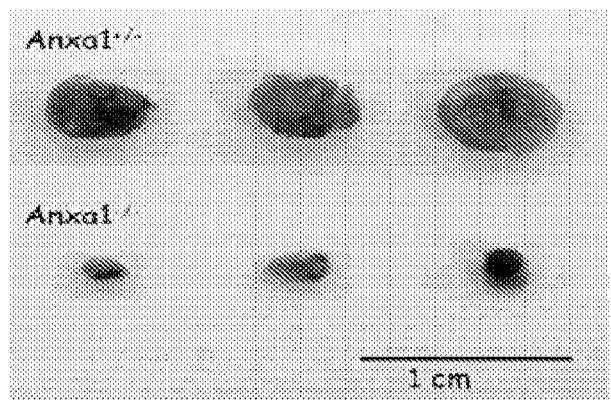
Figures 1C, 1D:
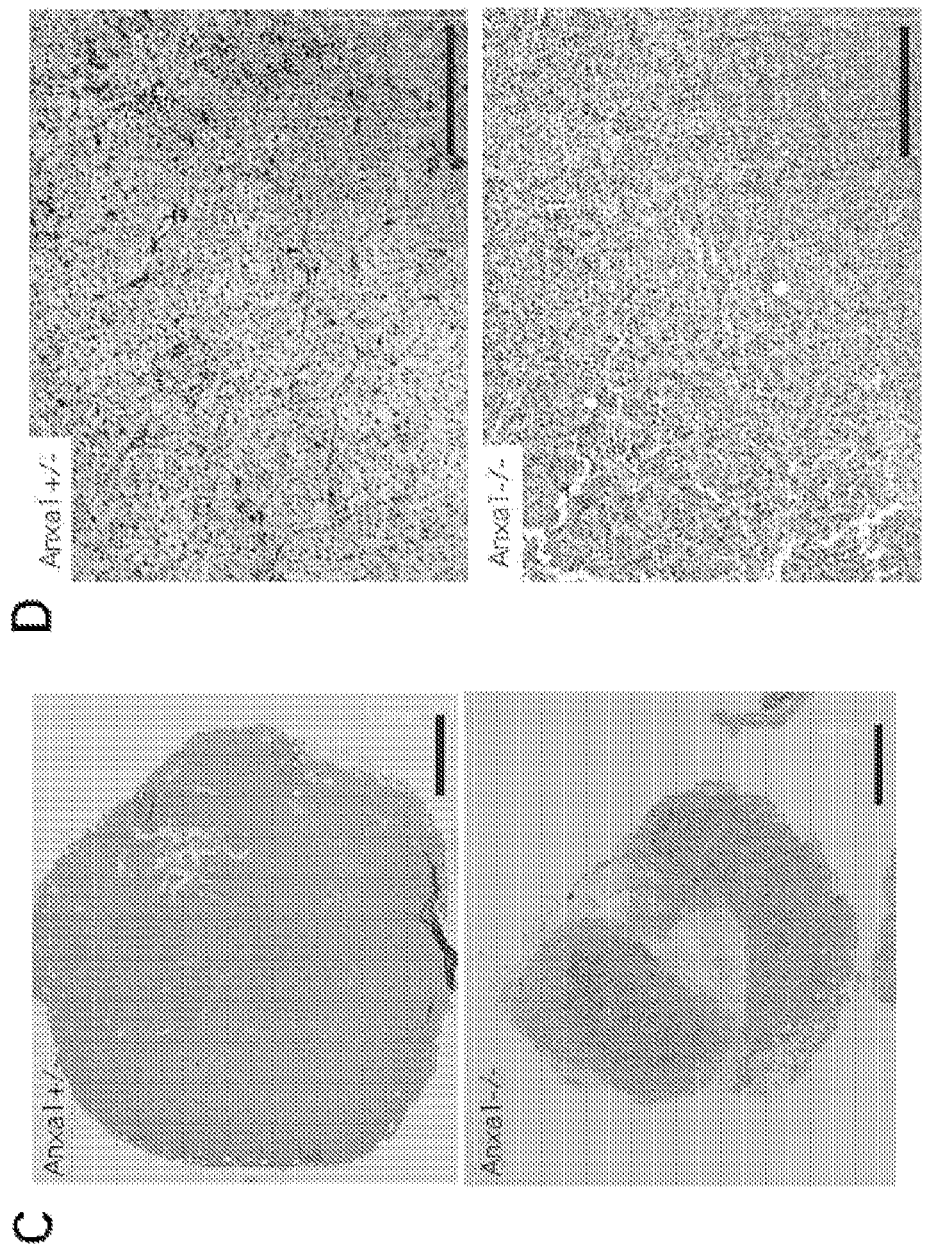

When B16 melanoma cells were injected subcutaneously in Anxa1 null mutant mice (R. Hannon et al. Aberrant inflammation and resistance to glucocorticoids in annexin 1-/- mouse. Faseb J 17:253-255, 2003) completely backcrossed to C57BL/6, tumor growth was significantly reduced compared to tumors produced in Anxa1 heterozygous mice (FIG. 1A, B). Tumors produced in Anxa1 nulls were largely necrotic (FIG. 1C). Remarkably, no vasculature was found in tumors produced in Anxa1 null mice (FIG. 1D). These findings suggest that Anxa1 expression on the endothelial cell surface (P. Oh et al. Subtractive proteomic mapping of the endothelial surface in lung and solid tumours for tissue-specific therapy. Nature 429:629-635, 2004) is essential for active tumor growth in the mouse.

ii. Identification of IF7: Tumor-Targeting and Anxa1-Binding Peptide

Figure 1E:
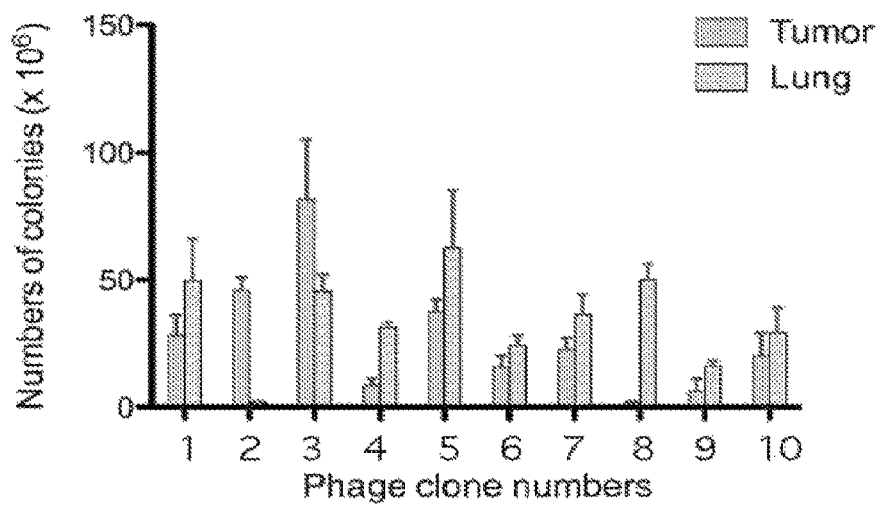
Figure 1F:
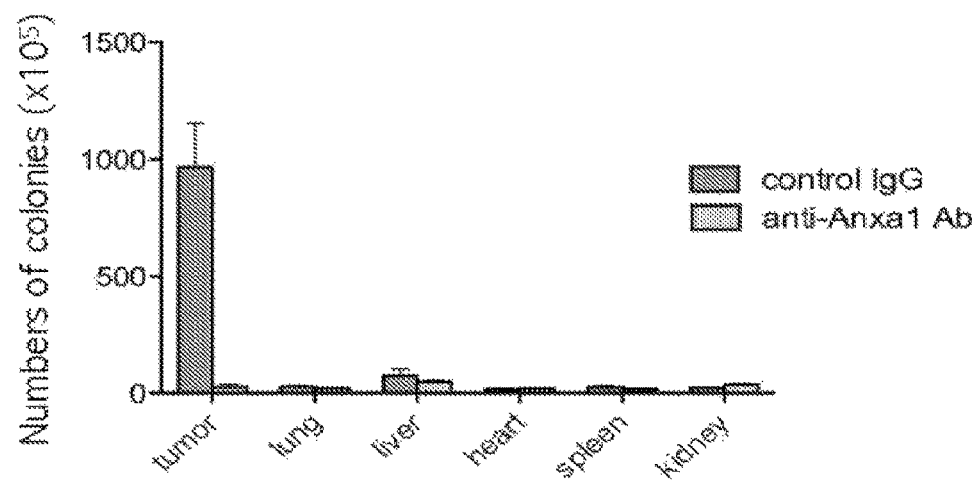

I-peptide (IELLQAR; SEQ ID NO: 13), was identified as a selectin ligand mimicry, and when injected intravenously into mice, synthetic I-peptide inhibited carbohydrate-dependent cancer cell colonization to the lung (Fukuda et al., Cancer Res 2000; 60: 450-6; Zhang et al. Cancer Res 2002; 62:4194-8). I-peptide binding activity to Anxa1 can be used as a tumor-targeting vehicle. However, as previously shown the I-peptide also targets to normal lung through pre-mRNA splicing factors (Hatakeyama, S. et al., Proc Natl Acad Sci 2009; 106:3095-100). Thus, a peptide sequence specifically targeting tumor but not normal lung vasculature is desirable. Organ targeting of phage clones intravenously injected into tumor-bearing mice indicated that IFLLWQR, designated IF7, targets tumor but not lung tissue (FIG. 1E, clone #2). Furthermore, tumor targeting by IF7 phage was completely inhibited by anti-Anxa1 antibody (FIG. 1F), showing that IF7 binds to tumor vasculature through Anxa1 expressed on the endothelial cell surface (Oh et al. Nature 2004; 429:629-35). Although low levels of Anxa1 was detected in lung by biotinylation (Hatakeyama et al., Proc Natl Acad Sci 2009; 106: 3095-100), IF7 targeting to the lung in tumor-bearing mice could not be detected (FIG. 1F), showing that Anxa1 levels expressed on the lung endothelial cell surface are significantly lower than those expressed on the tumor vasculature.

Figures 1G, 1H:
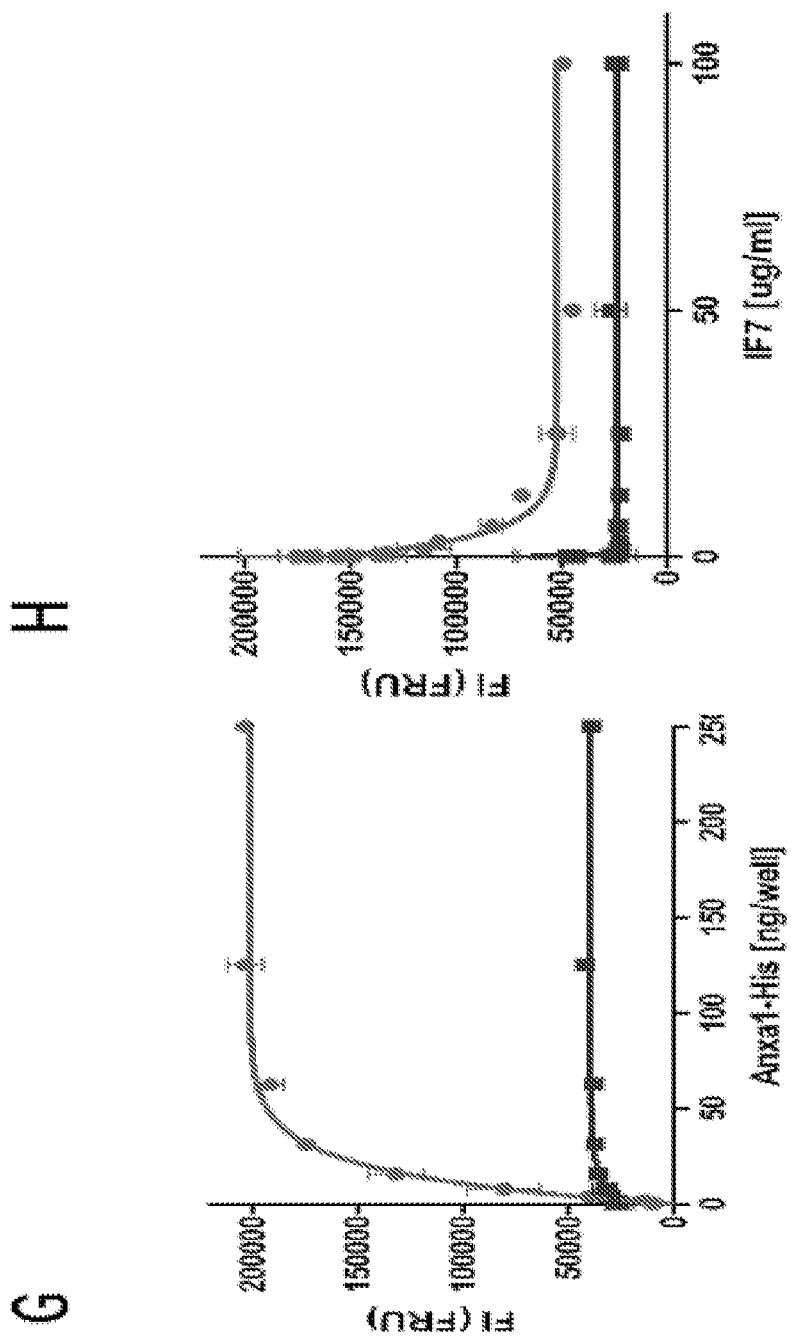
Figure 2:
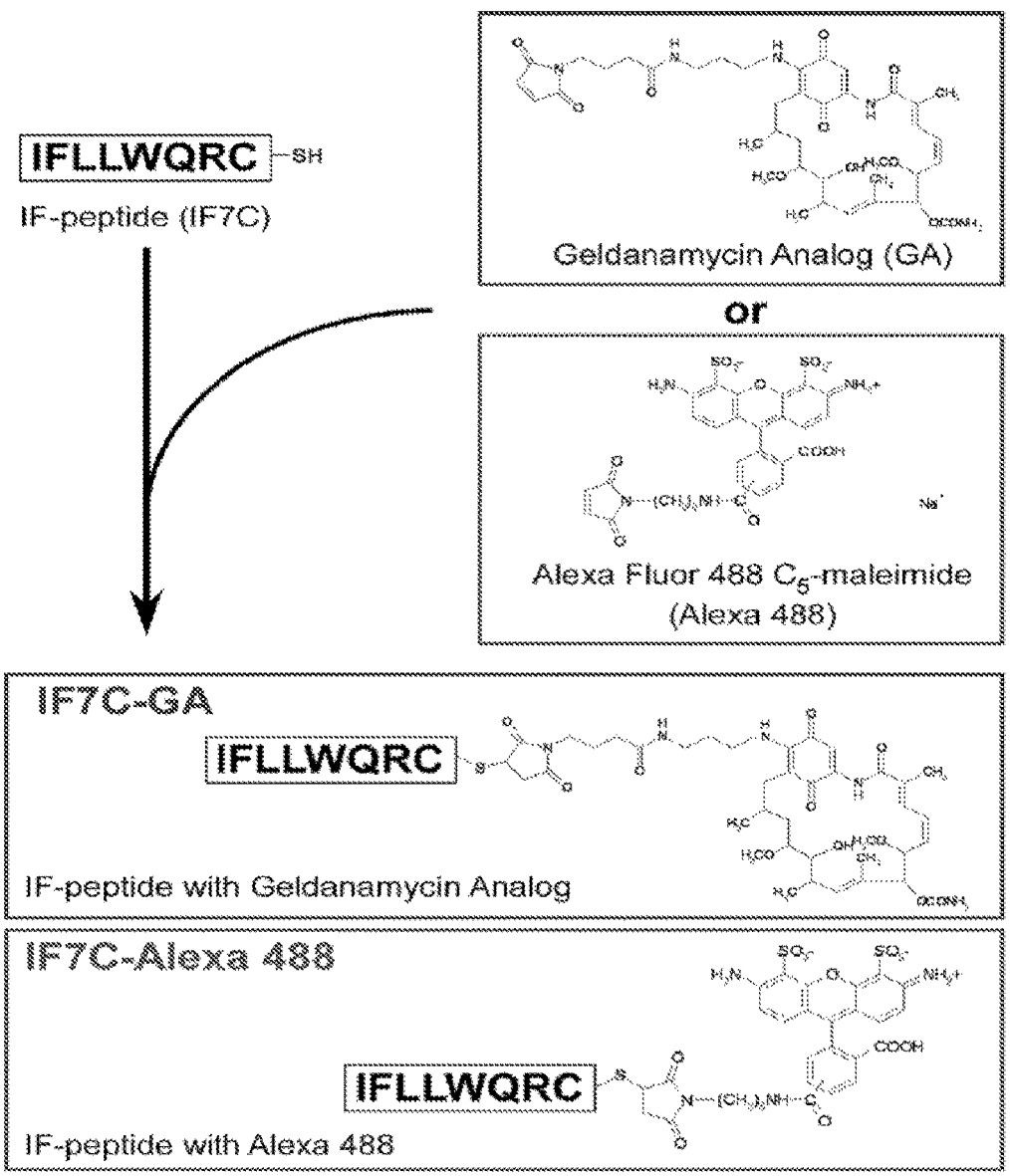
FIG. 2 shows conjugation of IF7C peptide (SEQ ID NO: 14) with GA and with Alexa 488. A geldanamycin analogue, 17-GMB-APA-GA (GA), was purchased from Invivogen (San Diego, Calif.). GA was also synthesized from geldanamycin (LC labs, Woburn, Mass.) as described by Mandler et al (J Natl Cancer Inst 92, 1573-81, 2000). Briefly, GA was dissolved in chloroform and mixed with 1,3-diaminopropane (Sigma-Aldrich) under argon gas at room temperature for 20 hours. Diaminopropane cross-linked GA was precipitated with hexane. The precipitate was dissolved in chloroform, and was reacted with N-[g-maleimidobutyryloxy] succinimide ester (Pierce, Rockford, Ill.) at room temperature for 2 hours. The product or 17-GMB-APA-GA was purified by thin layer chromatography using preparative TLC plate (1.5 mm silica gel, Analtech, Newark, Del.) in solvent system, dichloromethane:methanol (92:8, v/v). The structure of 17-GMB-APA-GA was verified by ESI mass spectrometry (Micromass ZQ) with MASSLYNX ver3.5 (Waters Corp., Milford, Mass.). To conjugate IF7C peptide (SEQ ID NO:14) with 17-GMB-APA-GA, they were dissolved in methanol at 1:1 molar ratio. Equal volume of purified water was added for the mixture, and was left at room temperature for 2 hrs. The product, IF7C-GA, was purified by C18 reverse-phase HPLC column (10×150 mm) by gradient elution from 40% to 50% acetonitrile in water containing 0.1% (v/v) trifluoroacetic acid at a flow rate of 2.5 ml/min. The purity and structure of IF7C-GA was assessed by ESI mass spectrometry. IF7C was also conjugated with Alexa fluor 488 $C_5$-maleimide (Invitrogen, Carlsbad, Calif.) and purified by HPLC in a similar manner as described above.
Figure 3:
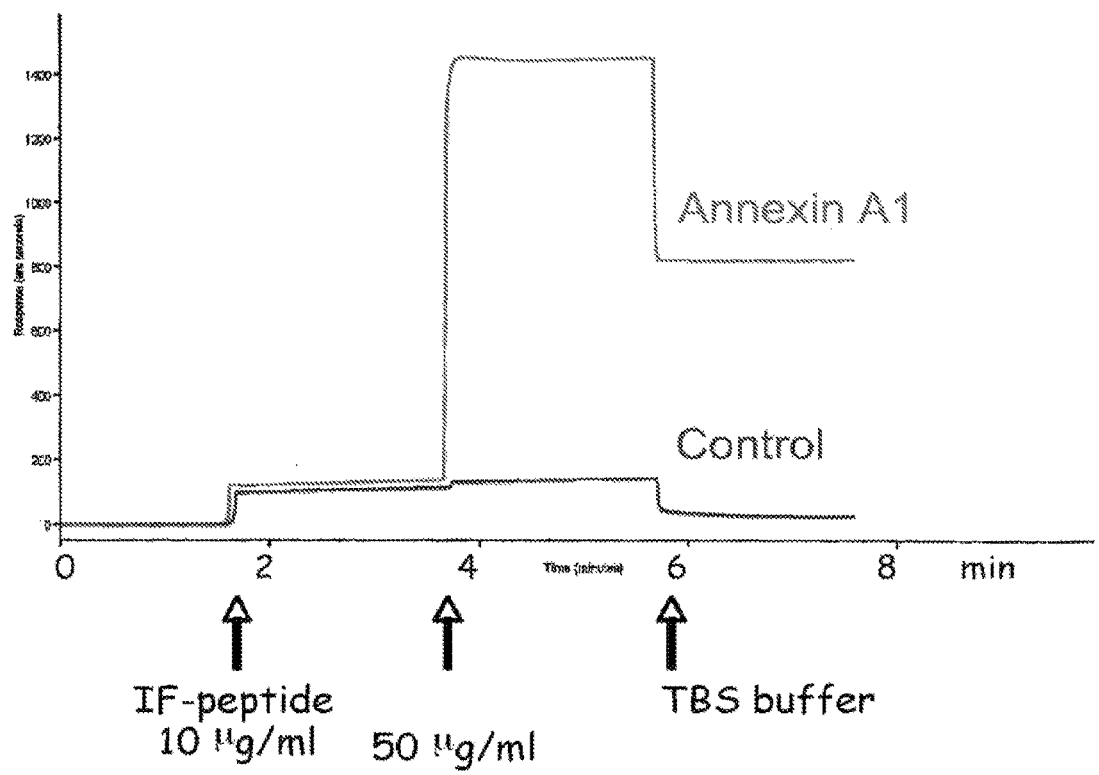
FIG. 3 shows surface plasmon resonance analysis of IF-peptide on Anxa1 coated chip and control uncoated chip. IASys (Affinity Sensors, Cambridge, UK) was used. Anxa1-His protein was immobilized on the sensor chip by cross-linking to the aminosilane surface using bis[sulfosuccinimidyl] substrate (Pierce). Binding of IF7C dissolved in TBSC was recorded for 2 min, and dissociation of IF7C was initiated by adding TBSC to the sensor chip and the arc second was recorded for 5 min.
Figure 4:
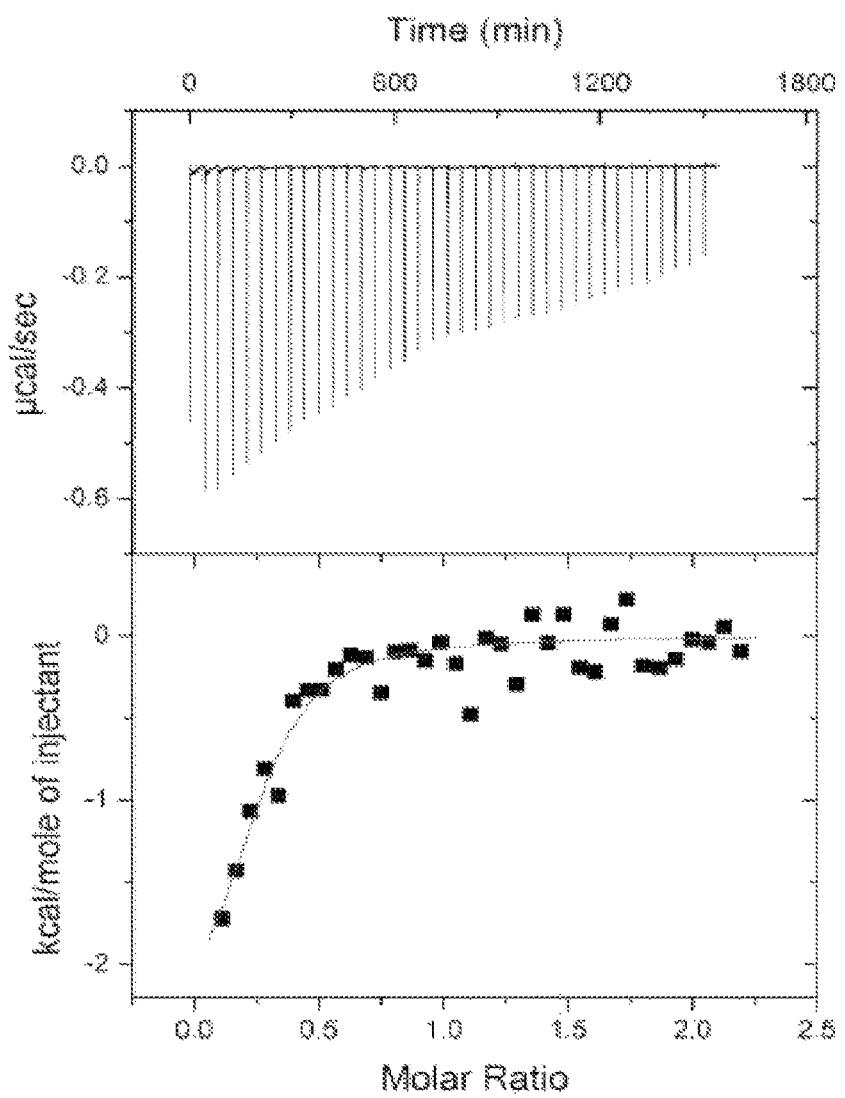
FIG. 4 shows isothermal colorimetry analysis of IF7K3C with Anxa1-His protein. ITC was performed on a VP-ITC calorimeter from Microcal (Northampton, Mass.). In this analysis IF7K3C peptide or IFLLWQRKKKC (SEQ ID NO:12), in which IF7 was modified by inserted with three lysine residues between IF7 and C to increase solubility in water. Eight µl aliquots of solution containing 1.0 or 1.5 mM were injected into the cell containing 100 or 150 µM Anxa1-His protein. In each experiment 37 injections were made. The experiments were performed at 23° C. in buffer containing 20 mM Tris pH 7.9, 250 mM NaCl, 1 mM CaCl2 and 10% dimethylsulfoxide. Experimental data were analyzed using Microcal Origin software provided by the ITC manufacturer (Microcal, Northampton, Mass.). An average ($K_d$=11±6 µM, n=4) was obtained using two different Anxa1-His preparations.

Chemically synthesized IF7 conjugated with fluorescent Alexa 488, the conjugate, designated IF7-A488 (FIG. 2), binds to recombinant Anxa1-His$_6$ protein in a plate assay, whereas RQ7-A488 (Alexa 488 conjugated with RQWLLFI (SEQ ID NO:15) or reverse IF7) did not bind to Anxa1 (FIG. 1G). IF7 binding to Anxa1 was confirmed by surface plasmon resonance and isothermal titration assays (FIGS. 3 and 4). Fucosylated carbohydrates bound to Anxa1 (FIG. 4), and that binding was inhibited by IF7 but not by RQ7 (FIG. 1H).

iii. In Vivo Tumor Targeting Activity by IF7

Figures 5A, 5B:
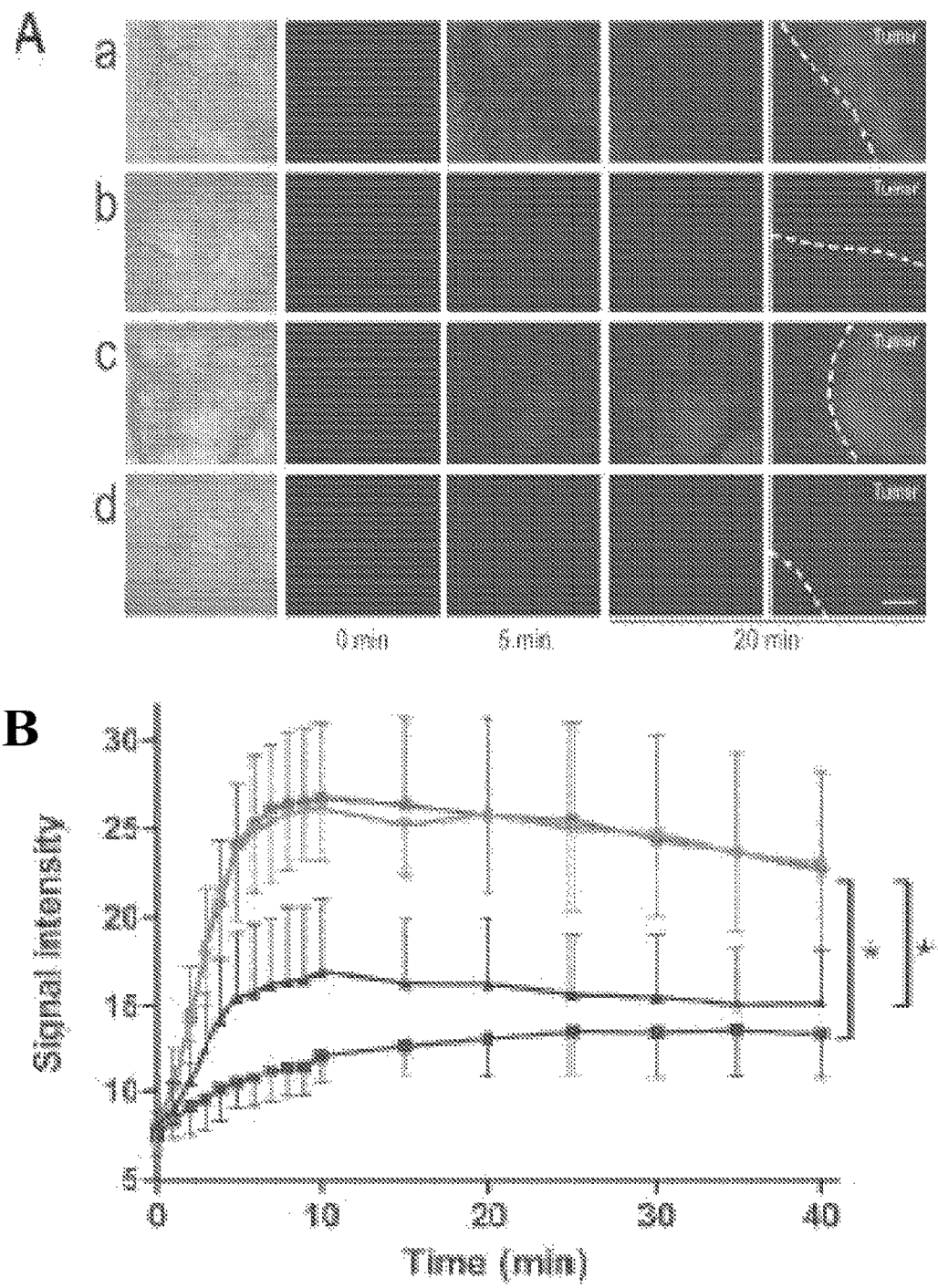
FIGS. 5A-5D shows in vivo targeting of IF7-A488 to tumors in a dorsal skinfold chamber. (A) Lewis lung carcinoma (LLC) tumors were allowed to vascularize for 3 days in dorsal skinfold chamber window in nude mice. Mice were injected with 100 µl of 50 µM IF7-A488 (row a) or RQ7-A488 (row b) in 5% glucose in water. IF7-A488 was also injected to tumor-bearing mice pre-injected with rabbit IgG (row c) or with rabbit anti-Anxa1 antibody (row d). Fluorescence signals were monitored under a fluorescence microscope up to 40 min post-injection. From left: bright field before injection, and fluorescence at 0, 5, 20 min after injection. Far right, the boundary of tumor and stroma at 20 min (Scale bar=500 µm). (B) Quantitative analysis of fluorescence during the course of the analysis shown in A. The line with the highest signal at 10 minutes represents IF&-A488. The line with the second highest signal at 10 minutes represents the control IgG. The line with the third highest signal at 10 minutes represents Anxa-1 antibody. The line with the lowest signal at 10 minutes represents RQ7-A488. Intensity of fluorescence was determined by Image J program. Error bars represent SD (n=3). Asterisks show statistical significance or p<0.0001, t test. (C) Fluorescence micrographs of tumor sections 20 min after injection with IF7-A488 and RQ7-A488. From left: IF7-A488, DAPI, merged, and bright field. IF7-A488 signals (upper row) were detected on endothelial cells of tumor vasculature (Scale bar=50 µm), while no RQ7-A488 signal was detected (lower row). Experiments were repeated 3 times, and representative results are shown. Arrows indicate fluorescence. (D) Fluorescence remained in circulation in mice with or without subcutaneous B16 tumors. IF7-A488 was injected intravenously through the tail vein, and fluorescence remaining in circulation was measured. Upper line represents "without tumor", middle line represents "with 3 days tumor", and bottom line represents "with 6 days tumor." Error bars represent SD (n=3).
Figures 5C, 5D:
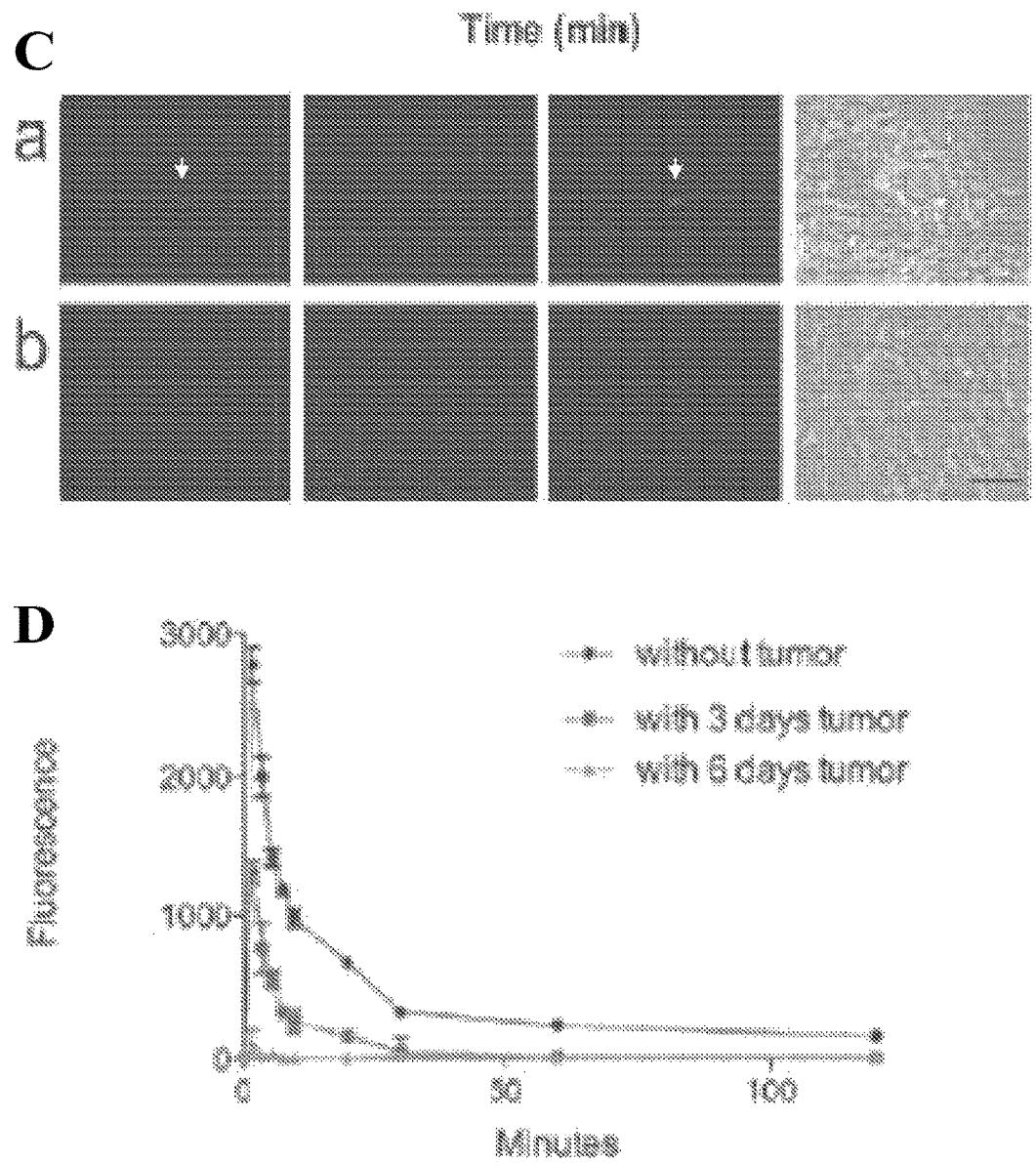

To test in vivo tumor vasculature targeting activity by IF7, tumors were produced in a dorsal skinfold chamber installed on nude mice (Lehr et al., Am J Pathol 1993; 143: 1055-62). IF7-A488 was injected through the tail vein and tumor fluorescence was monitored microscopically, fluorescence signals appeared in the tumor within one minute, reached a plateau in 9 min, and remained high for 40 min or until the experiment was terminated (FIG. 5A-a, FIG. 5B). By contrast, control peptide RQ7-A488 signals were either not detectable or remained at background levels (FIG. 5A-b, FIG. 5B). When anti-Anxa1 antibody was injected prior to IF7-A488 injection, fluorescence signals in tumors were significantly reduced (FIG. 5A-d, 5B). On the other hand, an irrelevant rabbit IgG antibody did not inhibit IF7-A488 tumor targeting (FIG. 5A-c, 5B). Tissue sections prepared from the tumor 20 min after injection showed vascular staining by IF7-A488 (FIG. 5C-a) but not RQ7-A488 (FIG. 5C-b). These results indicate that IF7 targets the tumors through Anxa1 expressed on the endothelial cell surface.

IF7-A488 levels remaining in circulation of tumor-bearing mice can indicate the tumor targeting efficacy by IF7 (FIG. 5D). When IF7-A488 was injected intravenously into control mice without tumors, IF7-A488 remained in circulation after an initial surge. However, when IF7-A488 was injected into B16-tumor-bearing mice, the initial surge of fluorescent signals was significantly reduced, followed by their complete disappearance from the circulation, indicating extremely high tumor-targeting efficacy of IF7.

iv. Tumor-Specific Delivery by an IF7-Conjugated Drug

Figure 6A:
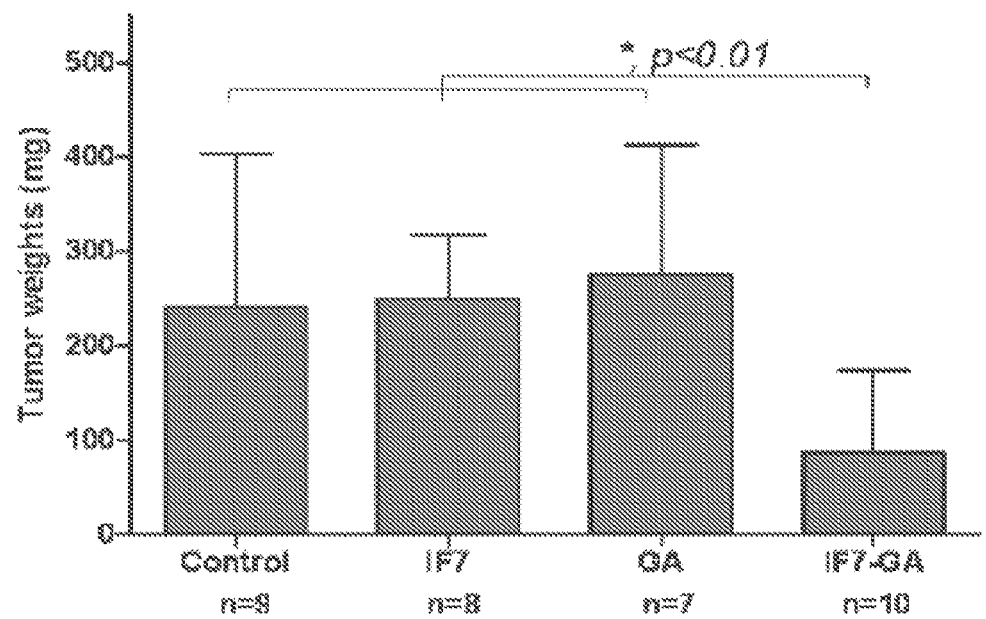
FIGS. 6A and 6B show the effect of IF7-GA on melanoma, lung carcinoma, prostate cancer, and breast cancer mouse models. A, Effect of IF7-GA on tumor size. (a) Mouse melanoma B16F1 tumors were grown subcutaneously in C57BL6 mice. On day 10, each mouse was injected intravenously with either 100 µl of 5% glucose or that containing 0.13 µmoles of each IF7, GA, or IF7-GA. Injections were administered every other day, for a total of three injections, until day 14. Mice were euthanised on day 15 to measure tumor weight. (b) Mouse Lewis lung carcinoma (LLC) tumors were grown subcutaneously in C57BL6 mice. On day 7, each mouse was injected intravenously with the compounds as in A-a, and injections administered every other day, for a total of three injections, until day 11. Mice were euthanised on day 13 and tumors weighed. (c) Human prostate cancer PC3 tumors were grown orthotopically in the prostate of SCID mice. On day 7, each mouse was injected intravenously with the compounds as in A-a, and injections administered every 4 days, for a total of four injections, until day 22. Mice were euthanised on day 28 and tumors weighed. (d) Human breast cancer MDA-MB-231 tumors were grown orthotopically in fat pads of SCID mice. On day 7, each mouse was injected intravenously with the compounds as in A-a, and injections performed every 4 days, for a total of four injections, until day 22. Mice were euthanised on day 28 and tumors weighed. Asterisks show statistical significance (Mann-Whitney's U test). B, Histochemistry of tumors from the mice intravenously injected with the compounds described in A. Apoptotic tumor cells along blood vessels in transplanted tumors are detected by TUNEL assay. B16 melanoma (a), LLC lung carcinoma (b), PC3 prostate tumor (c) and MDA-MB-231 breast tumor (d) from mice treated with each compound. Note that perivascular cancer cells rarely show apoptosis in control IF7, and GA groups, while perivascular tumor cells in the IF7-GA groups show greater numbers of apoptotic cells (some areas outlined in black) (Scale bar=50 µm).
Figure 6A:
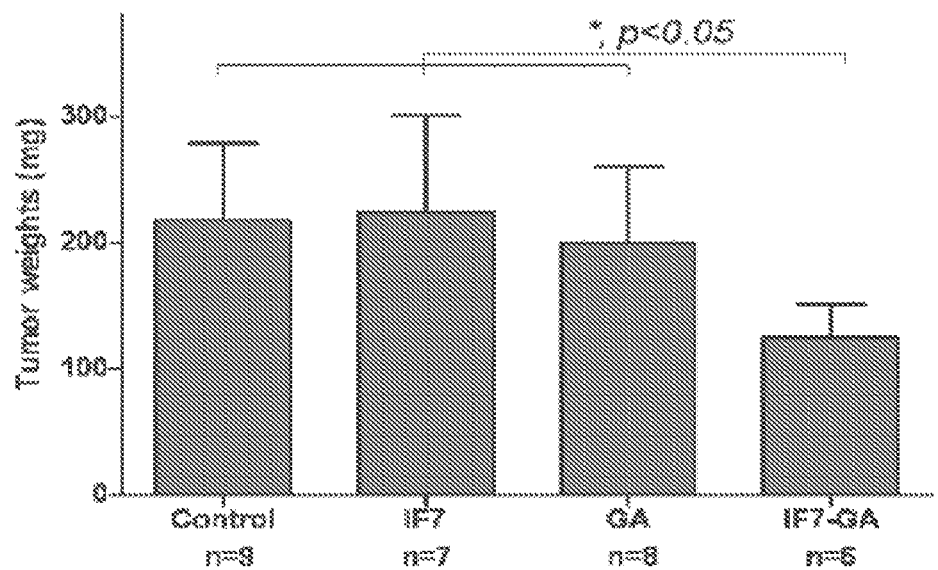
Figure 6A:
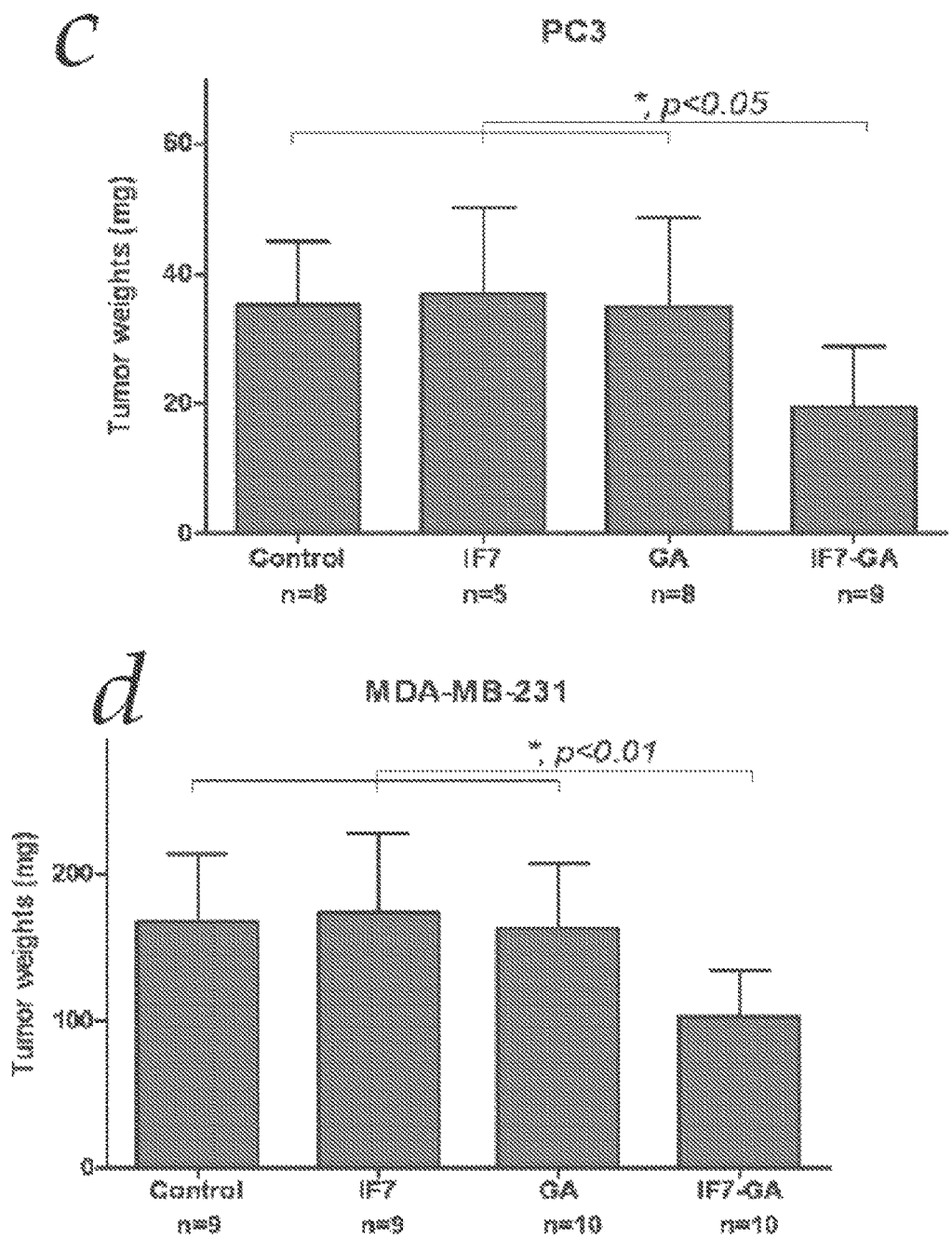

An anti-cancer drug conjugated to IF7 can deliver the drug to the tumor and suppress tumor growth in vivo. IF7 was conjugated with a geldanamycin analogue 17-AAG, an apoptosis-inducing drug (Vasilevskaya, I. et al., Cancer Res 2003; 63: 3241-6; Mandler, R. et al., J Natl Cancer Inst 2000; 92: 1573-81) (FIG. 2). When the IF7-GA conjugate was injected intravenously into B16 tumor-bearing mice, tumor growth was suppressed: tumors from IF7-GA-treated mice were significantly smaller than those from control mice (FIG. 6A-a). It should be noted that the dose of 17-AAG used as IF7-GA was 5 mg/kg, whereas 50-75 mg/kg 17-AAG has been used in previous studies of mouse tumor models (Eiseman et al., Cancer Chemother Pharmacol 2005; 55:21-32; Solit et al., Clin Cancer Res 2002; 8:986-93; Mitsiades, C. et al., Blood 2006; 107:1092-100). While B16 tumors from control mice showed active growth around blood vessels (FIG. 6B-a), B16 cells in tumors from IF7-GA-treated mice showed clear signs of apoptosis along vessels and morphologically apparent necrosis of blood vessels, indicative of a GA effect against tumor and tumor endothelial cells (Vasilevskaya et al., Cancer Res 2003; 63: 3241-6; Solit et al., Cancer Res 2003; 63:2139-44). Histological analysis of major organs from all mice used showed no apparent abnormalities. Blood tests from all mice showed no abnormalities in liver function, kidney function and blood cell count. However, tumor-bearing mice treated by IF7-GA did not survive longer than control mice.

Similar results were obtained using a lung carcinoma tumor model produced by subcutaneous injection of Lewis lung carcinoma (LLC) cells into BL6 mice (FIG. 6A-b, FIG. 6B-b), and in human prostate and breast cancer mouse models produced by respective orthotopic injection of human prostate cancer PC3 cells and breast cancer MDA-MB-231 cells into immunodeficient mice (FIGS. 6A-c, 6A-d, 6B-c and 6B-d).

Figure 7:
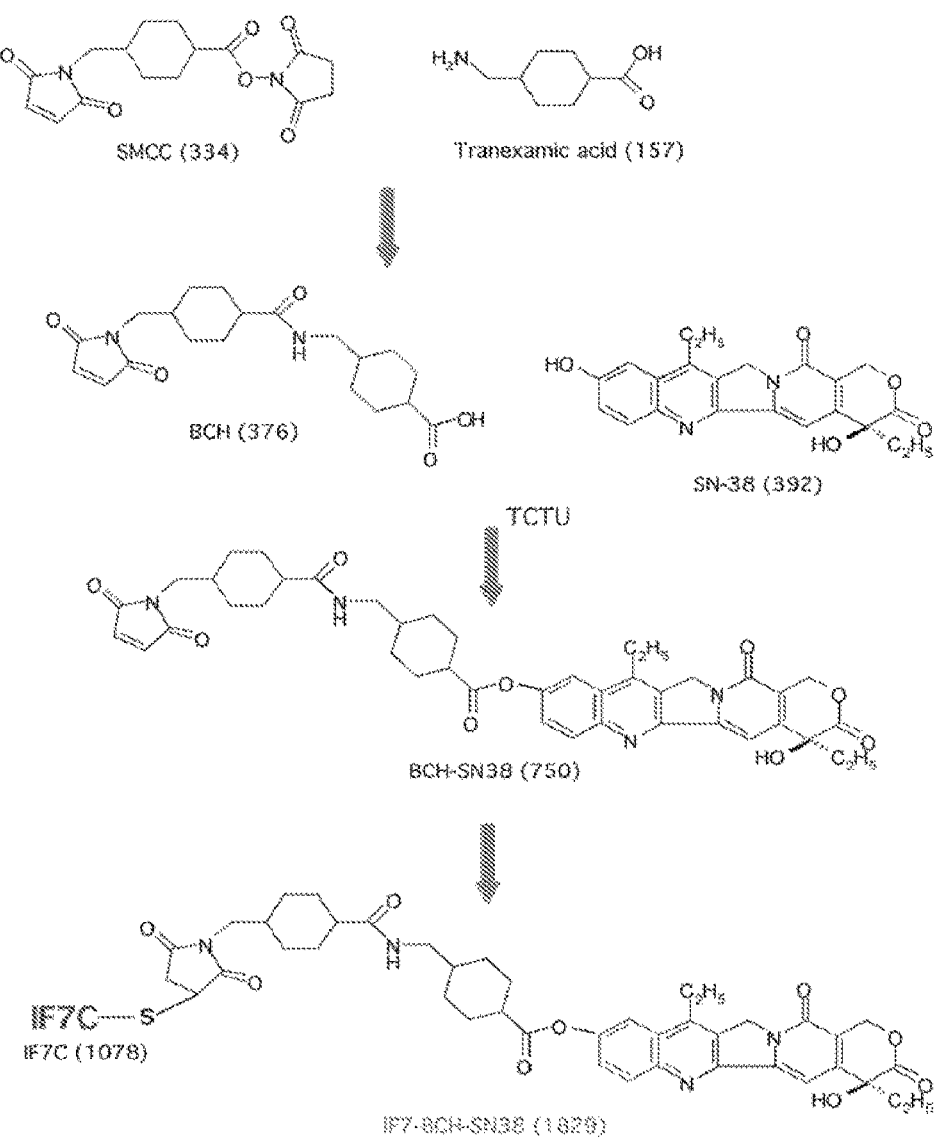
FIG. 7 shows Synthesis of IF7-SN38. SN-38 was synthesized by Yakult (Tokyo, Japan). The conjugation was performed according to the method described by Meyer-Losic et al., Clin Cancer Res 2008; 14: 2145-53, except followings. Trans-4-(Aminomethyl)cyclohexanecarboxylic acid (Tranexamic acid, 500 mg) was dissolved in water (12.5 ml), and was added with IM-phosphate buffer, pH 6.5 (1 ml). Both trans- and cis-(Aminomethyl)cyclohexanecarboxylic acid were available; however tranexamic acid was more effective. SMCC (1 g) was dissolved in a mixture of acetonitrile (22 ml) and water (5.5 ml). Tranexamic acid and SMCC were mixed, which was incubated at 45° C. for 2 hours. The product 4-{4-[(N-maleimydomethyl)cyclohexanecarboxamido]methyl}cyclohexane-1-carboxylic acid (BCH) was extracted to organic phase by dichloromethane (60 ml) and 0.1 M NaCl in water (20 ml). Conjugation of BCH and SN-38 was performed at room temperature for 4 hours, and conjugation of IF7C and BCH-SN38 was performed by incubating them in dimethylformamide at 45° C. for 3 hours, following addition of water and incubation at room temperature for 20 hours. The product IF7-BCH-SN38 (IF7-SN38) was recovered from the interphase of dichloromethane (30 ml) and 5M NaCl in water (2 ml). Dried IF7-SN38 was dissolved in 50% acetonitrile in water, and purified by reverse phase HPLC, by a gradient elution from 50% to 70% acetonitrile in water containing 0.1% trifluoroacetic acid. The numbers in parenthesis are molecular weight of each compound, which was verified by mass spectrometry.
Figures 8A, 8B:
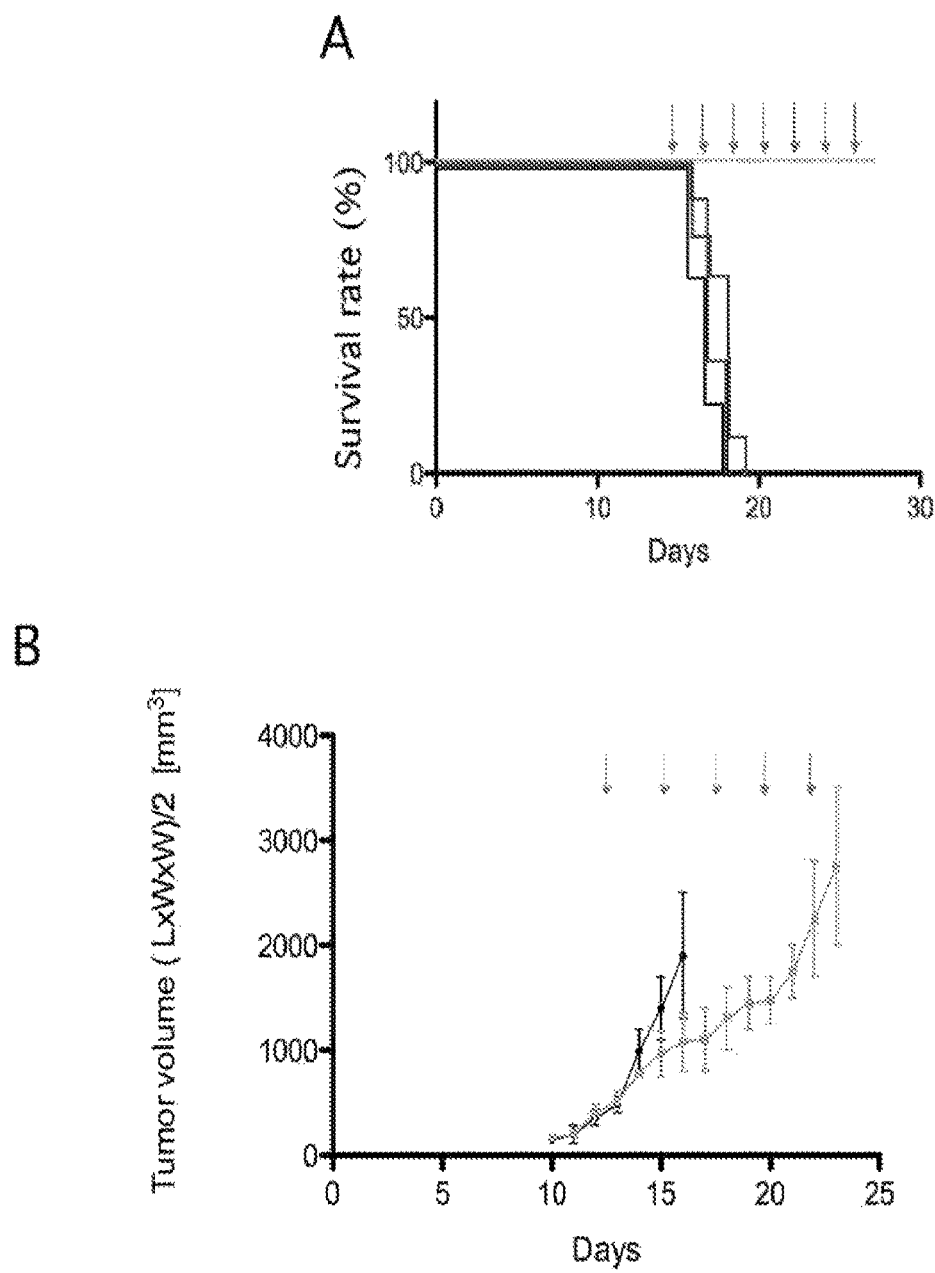
FIGS. 8A-8F show the effect of IF7-GA and IF7-SN38 on B16-tumor bearing mice. A. Survival of B16-tumor bearing mice treated with IF7-GA or IF7-SN38. B16 cells were injected subcutaneously into mice, and on day 14 each mouse was injected intravenously with either 100 μl of 5% glucose or that containing 0.13 moles of each IF7-GA, RQ7-SN38 or IF7-SN38. Injections were administered every other day, for a total of 7 injections, until day 26, as shown by arrows. Only IF7-SN38 exhibited high survival after 20 days; all of the others plummeted prior to 20 days. B. Effect of IF7-SN38 on tumor size. Mouse melanoma B16F1 tumors were grown subcutaneously in C57BL6 mice. On day 13, each mouse was injected intravenously with either 100 μl of 5% glucose (darker line) or that containing 0.13 moles of IF7-SN38 (lighter line). Injections were administered every other day, for a total of five injections, until day 21. Size of tumors was measured by using a caliper. Error bars represent SD (n=6). C. Size of tumors was measured by using a caliper. Error bars represent SD (n=6). Histology showed that a tumor from IF7-SN38 treated mouse is slightly smaller and contains more necrosis compared to a tumor isolated from control mouse (FIG. 8C). D. Survival of B16-tumor bearing mice treated with IF7-GA or IF7-SN38. B16 cells were injected peritoneally into mice, and on day 1 each mouse was injected intravenously with either 100 μl of 5% glucose or that containing 0.13 μmoles of each IF7-GA, RQ7-SN38 or IF7-SN38. Injections were administered every other day, for a total of 6 injections, until day 12, as shown by arrows. Mice were left until they showed a sign for weakness. IF7-SN38 exhibited high survival after 22 days; IF7-GA exhibited high survival until 20 days; glucose and RQ7-SN38 plummeted prior to 20 days. E. Day 10 peritoneal B16 tumors from mice intravenously injected with 5% glucose (a), IF7-GA (b), or IF7-SN38 (c). Scale bar represents 1 cm. F. Histology of peritoneal B16 tumors shown in E. Scale bars represent 100 μm.
Figure 8C:
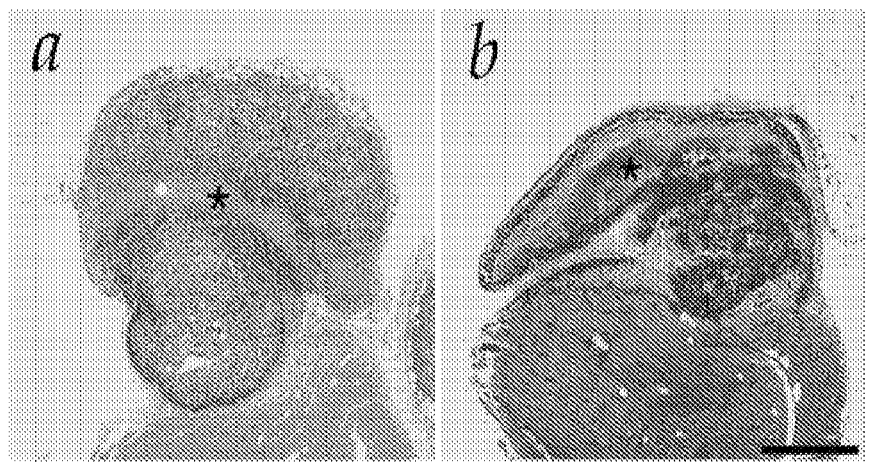

The IF7-GA dosage used herein can be considered to be optimal, as increasing doses did not improve survival of tumor-bearing mice or reduce tumor size. The failure to rescue IF7-GA-treated mice is due to modest activity of GA, which induces apoptosis by inhibiting Hsp-90 (Clarke et al., Oncogene 2000; 19:4125-33; Panaretou et al., Mol Cell 2002; 10:1307-18). Therefore IF7 was conjugated to SN-38, a highly potent anti cancer drug (Meyer-Losic et al., Clin Cancer Res 2008; 14:2145-53) (FIG. 7) using an esterase-cleavable cross-linker. Remarkably, when IF7-SN38 was injected intravenously into mice with large B16 solid tumors, those mice were rescued (FIG. 8A): tumor-bearing mice survived as long as IF7-SN38 injections continued (FIG. 8A). Thus, IF7-SN38 was effective in rescuing mice at near terminal stages, whereas IF7-GA was not. IF7-SN38 slowed tumor cell proliferation immediately following administration, although tumor size gradually increased (FIG. 8B). Despite large tumor sizes, mice showed no signs of weakness during extended days of survival mediated by IF7-SN38. Tumors from IF7-SN38-injected mice occasionally showed edema, while tumors from control mice did not. These observations indicate that fluid accumulation contributed to increased tumor size seen in IF7-SN38 injected mice. To determine the effect of IF7-SN38 on early stage of tumors, IF7-SN38 was injected on day 8, and tumors were isolated two days later. Tumors from IF7-SN38-injected mice are smaller and contain more necrosis compared to those from control mice (FIG. 8C). The IF7-SN38 dosage used in this study was at 7.5 mg/kg, whereas SN-38 conjugated with a peptide without tumor vasculature targeting activity was used at 95 mg/kg in a previous study (Meyer-Losic et al., Clin Cancer Res 2008; 14:2145-53).

Figure 8D:
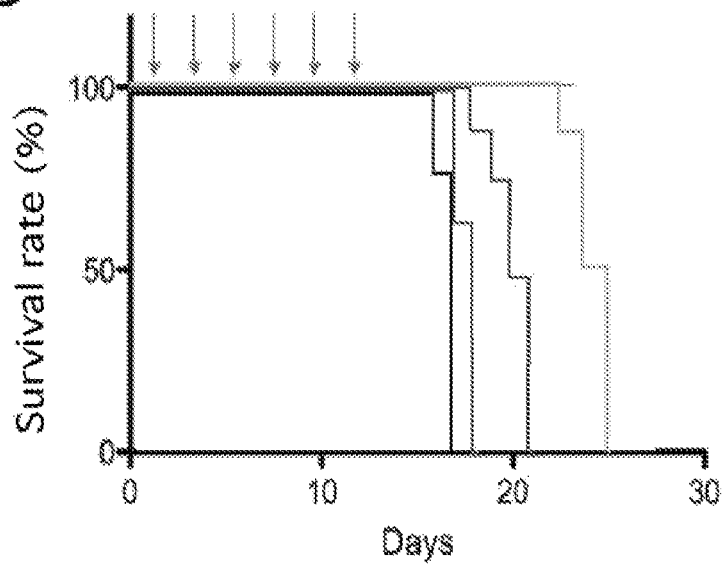
Figure 8E:
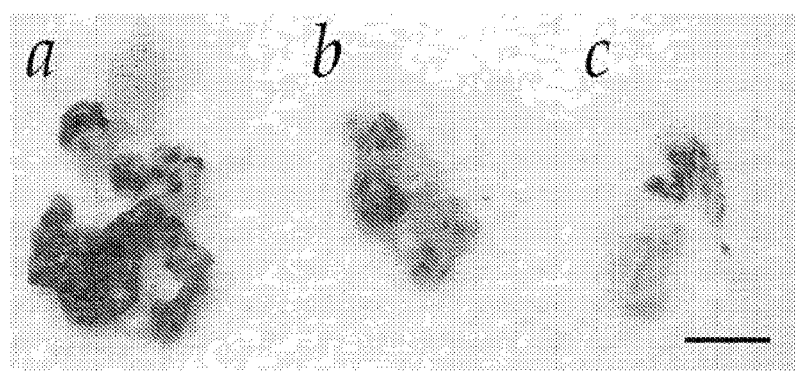
Figure 8F:
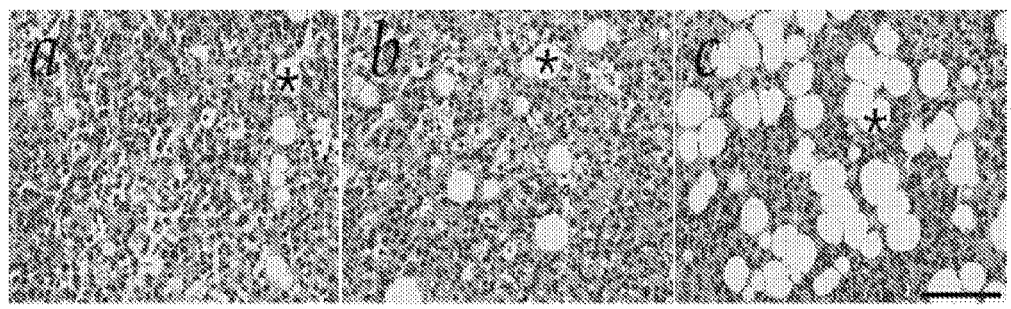

To further analyze the effect of IF7-SN38, mice with peritoneally injected B16 tumors were tested. In peritoneal B16 tumors, cancer cells grew rapidly and mouse survival was limited. In these experiments, IF7-SN38 lengthened the survival time of B16 tumor-bearing mice (FIG. 8D). IF7-GA was also effective in lengthening the survival of B16 tumor-bearing mice. Tumors isolated from IF7-GA treated and IF7-SN38 treated mice were smaller than those from control mice (FIG. 8E). In control tumor-bearing mice, many small foci resulting from micrometastasis were seen on the peritoneal wall, whereas micrometastasis was not detected in IF7-GA-treated and IF7-SN38-treated mice. Histology showed that tumors from IF7-GA and IF7-SN38 treated mice show more fat cells than tumor from control mouse (FIG. 8F), indicating that both IF7-GA and IF7-SN38 suppressed proliferation of cancer cells. Note that the effect shown in FIGS. 8E and 8F of IF7-SN38 is superior to the effect of IF7-GA. Blood tests showed no abnormalities in liver function, kidney function and blood cell count.

Figure 10:
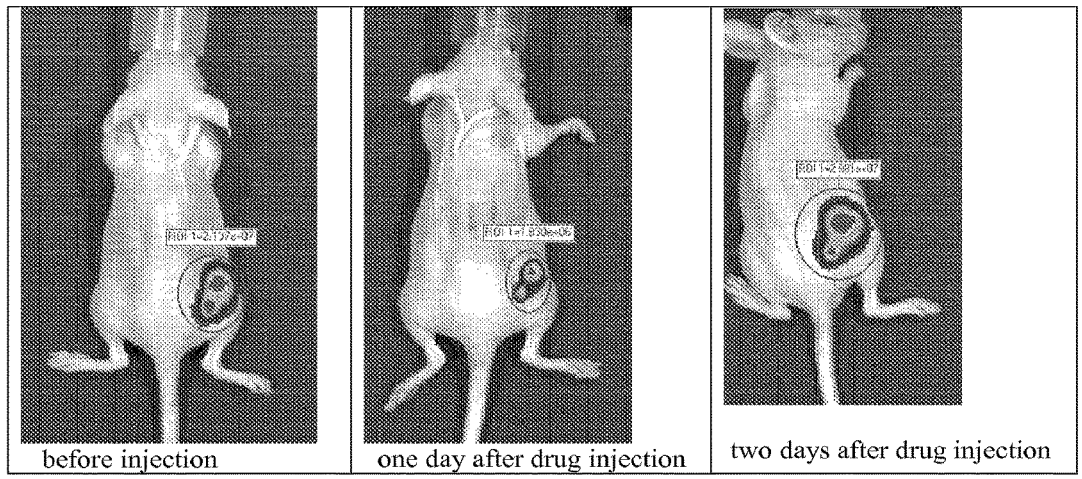
FIG. 10 shows images of HCT116-luc tumors visualized by Xenogen IVIS imager. Drug IF7-SN38 6.5 μmoles/kg was administered intravenously through tail vein.
Figures 11A, 11B:
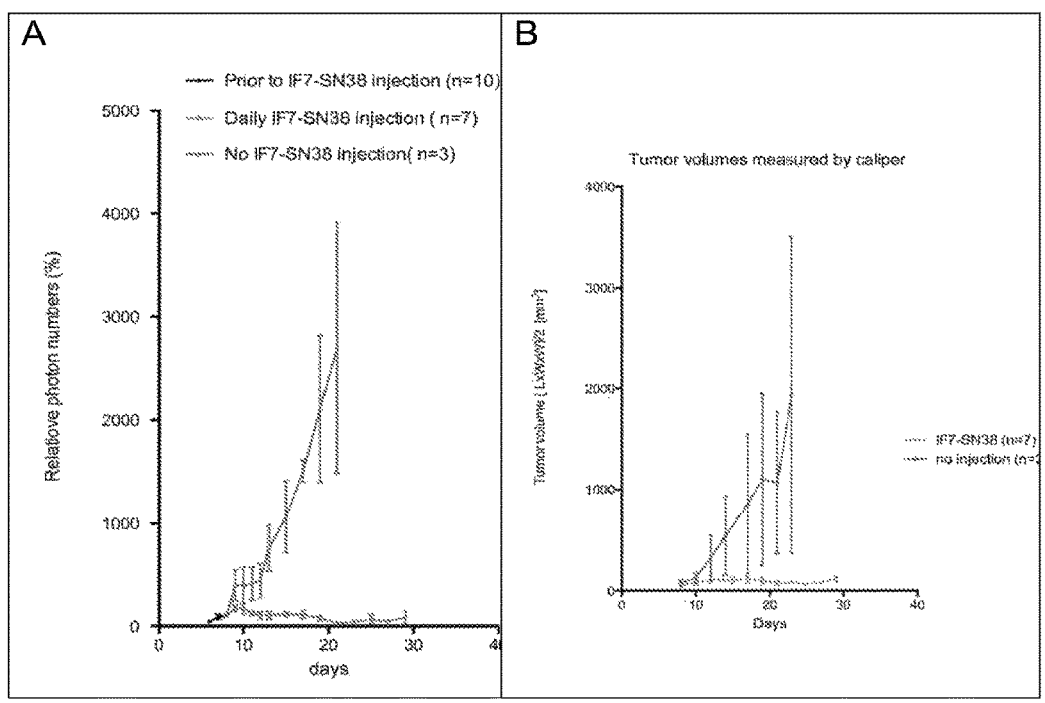
FIGS. 11A and 11B show the effect of IF7-SN38 on HCT116-luc tumors produced in nude mice. IF7-SN38 6.5 mmoles/kg was injected daily to HCT116-luc tumor bearing mice. A. Tumor size monitored by luciferase-based chemiluminescence. Photon numbers of 100% is the order of e+07. B. Tumor size monitored by caliper measurement.

In above described experiments, tumor size was measured using a caliper. However, this method is not the most accurate, in particular if necrosis causes edema or accumulation of lymphatic fluid in the tumor. In order to monitor the effect of IF7-SN38 in vivo in the mouse, a luciferase expressing stable cell line, HCT116-luc, was produced and photon numbers produced by live HCT116-luc cells were measured. When IF7-SN38 (0.68 moles) was injected to HCT116-luc tumor bearing mice, numbers of live HCT116-luc cells reduced in the next day, whereas without IF7-SN38 injection these cells increased 2 days later (FIG. 10). This indicated that IF7-SN38 should be administered daily to suppress tumor growth. When IF7-SN38 was injected intravenously every day to HCT116-luc tumor-bearing mice, growth the tumors was completely suppressed, which was demonstrated by both photon numbers and caliper measurements (FIG. 11).

v. Targeting and Penetration of IF7C(RR) Peptide to the Tumor Vasculature

Figures 12A, 12B, 12C:
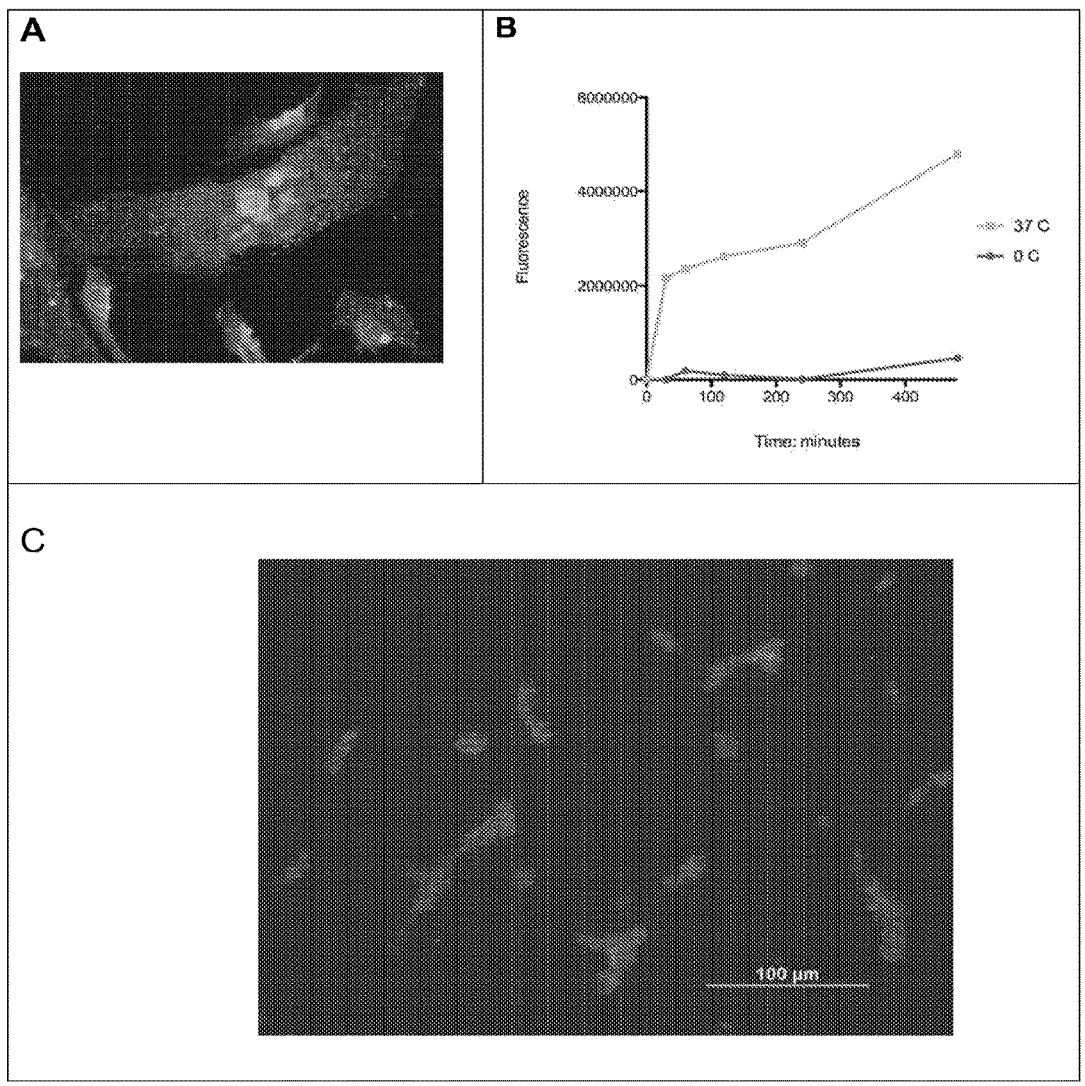
FIGS. 12A, 12B and 12C demonstrate the binding and penetration of IF7C(RR)-conjugated FITC-poly-lysine to Anxa1-expressing mouse endothelial cells. A. Binding of IF7C(RR)-conjugated FITC-polylysine on the surface of mouse endothelial F-2 cells cultured in vitro. B. Transport of FITC-conjugated FITC-poly-L-lysine through apical surface to basal space of F-2 cells monolayer. F-2 cells cultured on a filter of trans well insert was added with IF7C(RR)-conjugated FITC-poly-L-lysine to allow the reagent being bound to apical cell surface of F-2 cells. After washing the monolayer with medium, insert was placed in wells containing medium at 37° C. or at 4° C. Fluorescence moved to the lower chamber of insert was measured. C. Targeting and penetration of intravenously injected IF7C(RR)-conjugated FITC-poly-L-lysine in the B16 tumor in vivo in the mouse. Tissue section was immunostained for endothelial cell marker CD31. The fluorescence signals of FITC localize around and often at basal side of the endothelial layer, suggesting the penetration of IF7C(RR)-conjugated probe through endothelial cells.

Since IF7-SN38 is highly hydrophobic, there was a concern regarding a possibility that IF7-SN38 becomes insoluble after intravenous injection. Such may reduce the activity of IF7-SN38 in vivo. To increase the solubility of IF7-SN38 in aqueous environment, two arginine residues were added to IF7 after the cysteine residue. Thus IFLL-WQR-C-RR (SEQ ID NO: 17) or IF7C(RR) was synthesized. When IF7C(RR) was conjugated to FITC-poly-L-lysine, IF7C(RR)-conjugated FITC-poly-L-lysine bound to the surface of Anxa1-expressing mouse endothelial F-2 cells (FIG. 12A). The cytoplasmic and nuclear FITC signals are consistent with the localization of Anxa1 in the cytoplasm and nucleus (Gerke, 2005 #5299). FITC-poly-L-lysine without IF7C(RR) did not bind to F-2 cells (data not shown).

When IF7C(RR)-conjugated FITC-poly-L-lysine was added to F-2 cells grown on a filter of the insert for trans well chamber, washed and then incubated in a medium at 37° C. or at 4° C., fluorescence migrated to the lower chamber from cells incubated at 37° C. but not at 4° C. (FIG. 12B). This indicates that IF7C(RR) binding and transport is mediated by an active transport mechanism through cells. To determine if the binding and transport of IF7C(RR) occur in vivo in the tumor vasculature, IF7C(RR)-conjugated FITC-poly-L-lysine was injected intravenously into a B16 tumor-bearing mouse. The tumor tissue sections showed green fluorescence signals around the abluminal area of the vasculatures (FIG. 12C), indicating the binding of IF7C(RR) to the tumor vasculature and transport of this peptide from luminal to abluminal surface through endothelial cells. Small molecules such as SN-38 conjugated with IF7C(RR) can penetrate to the tumor deeper and faster than the large molecule such as poly-L-lysine.

vi. Effect of IF7C(RR) Conjugated SN-38 on HCT116-Luc Tumors

Figures 13A, 13B:
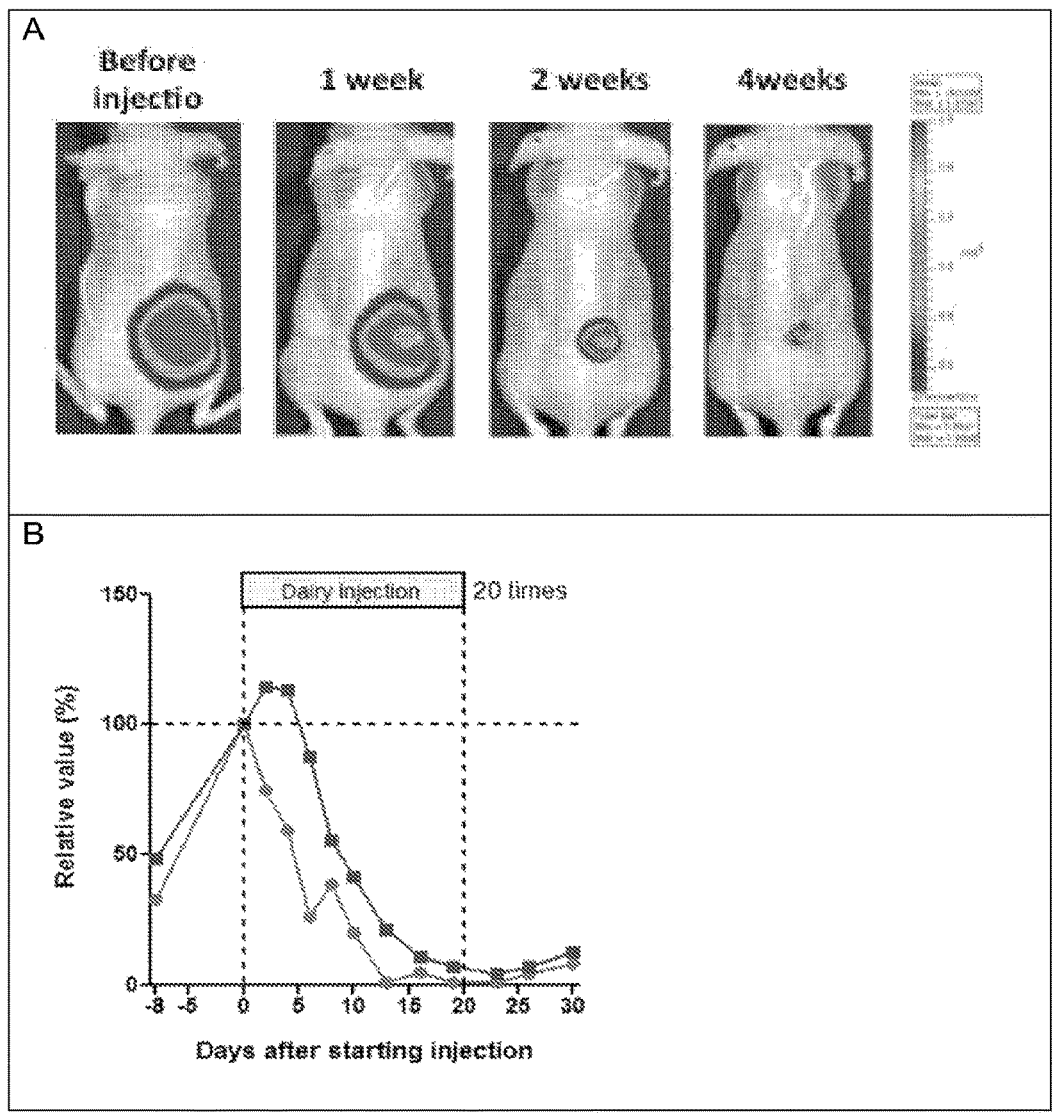
FIGS. 13A and 13B show (A) representative results of the effect of IF7C(RR)-SN38 on a large HCT116-luc tumor (photon numbers e+1 on day 0) produced in nude mice and (B) Dose of IF7C(RR)-SN38 for daily injection was 6.5 μmoles/kg, the same dose of IF7-SN38 shown in FIG. 11.

The activity of IF7C(RR)-SN38 was tested using HCT116-luc tumors described above. A nude mouse with large HCT116-luc tumor was injected with IF7C(RR)-SN38 by daily injection and tumor size was monitored by luciferase-based chemiluminescence (FIG. 13). It appears that IF7C(RR)-SN38 had stronger anti-tumor activity than IF7-SN38 shown in FIG. 11. IF7C(RR)-SN38 not only suppressed the growth but also reduce the size significantly, while IF7-SN38 did not substantially reduce the tumor size below the pre-drug injection level.

Figure 14:
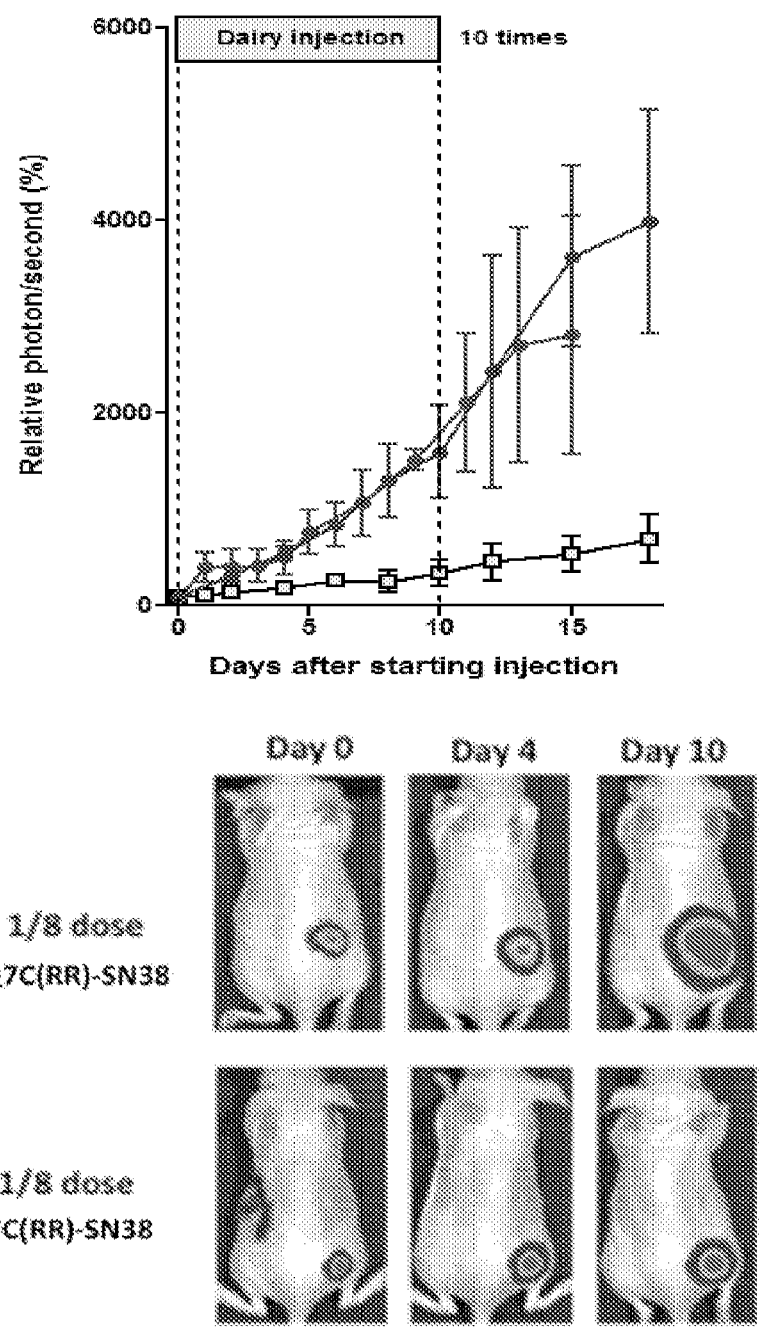
FIG. 14 shows the effect of low dosage IF7C(RR)-SN38 on HCT116-luc tumors produced in nude mice. IF7C(RR)-SN38 used was one eighth dose or 0.81 μmole/kg/injection compared to IF7-SN38 used at 6.5 moles/kg/injection (FIG. 11). Control RQ7C(RR)-SN38 was prepared by conjugating SN-38 with reverse IF7C(RR), RQWLLFI-C-RR peptide (SEQ ID NO: 16).
Figures 15A, 15B:
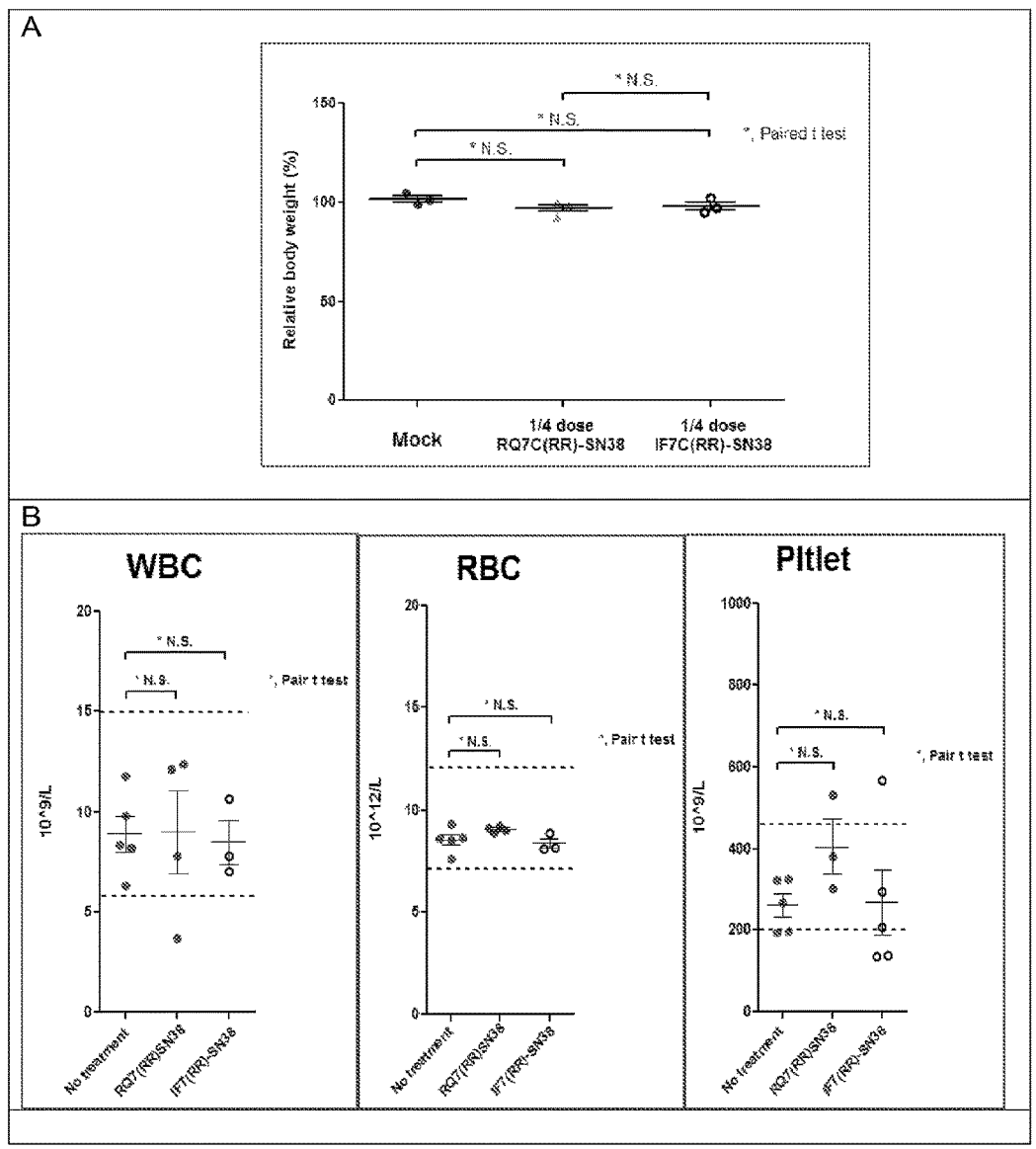
FIGS. 15A, 15B and 15C show body weights (A), blood cell counts (B), and blood chemistry (C) of the nude mice treated with IF7C(RR)-SN38 and RQ7C(RR)-SN38 daily injection for 10 days. None of the parameters showed significant differences to the control (no drug injection) group.
Figure 15C:
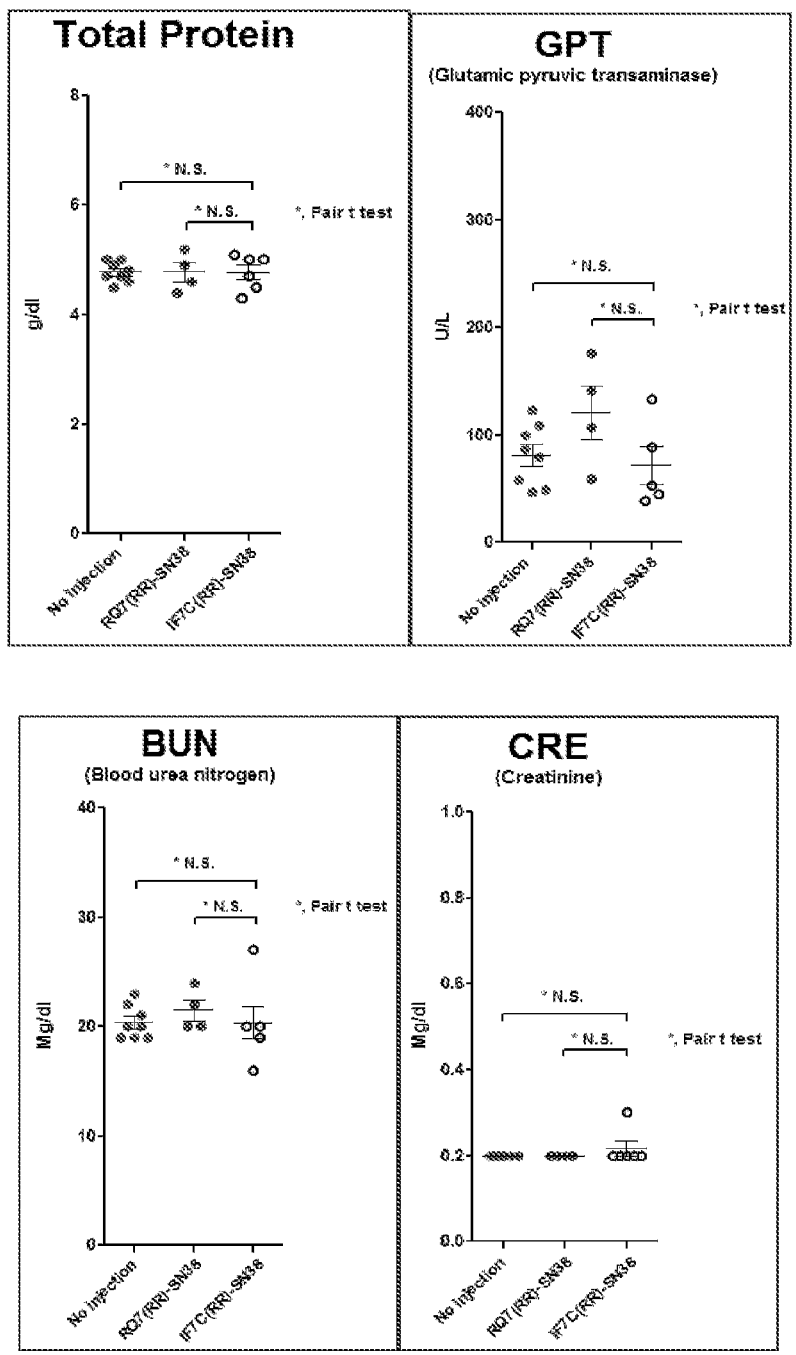

To determine further the anti-tumor activity of IF7C(RR)-SN38, the effect of this drug was tested at low doses. Reduced dosage experiments showed that IF7C(RR)-SN38 effectively suppressed HCT116-luc tumor growth as low as at 0.81 μmoles/kg (FIG. 14). We anticipated that IF7C(RR)-SN38 injected at these dosages have no side effects. This was confirmed by a series of blood tests (FIG. 15).

3. Discussion

Figure 6B:
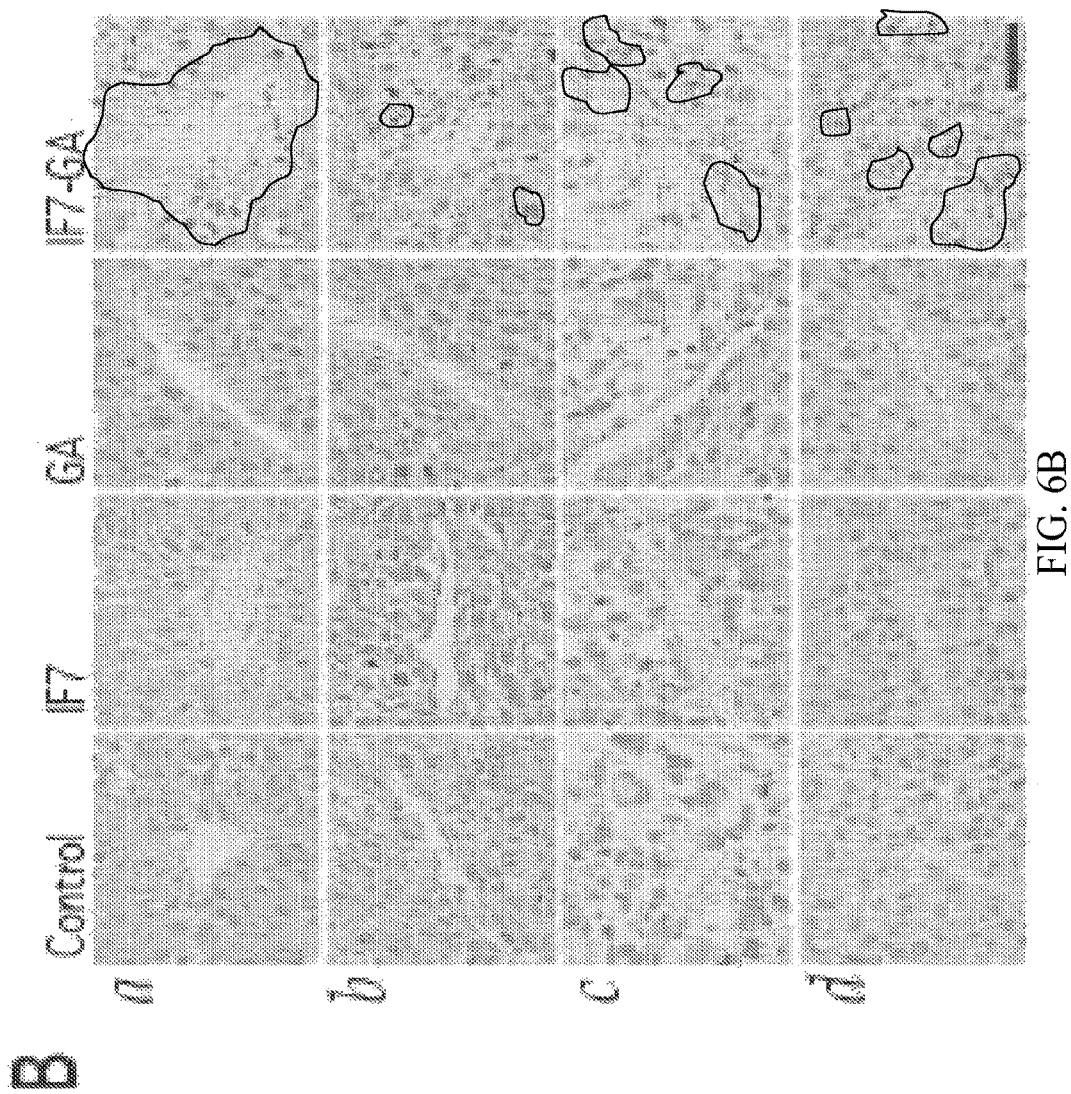

Anxa1 localizes to the tumor endothelial cell surface in endothelial caveolae and is internalized through endocytosis (Schnitzer et al., J Biol Chem 1995; 270:14399-404). A recent study indicates that a ligand bound to endothelial caveoli protein at the apical cell surface is efficiently transported to the basal surface and released to the stroma below (Schnitzer Adv Drug Deliv Rev 2001; 49:265-80). Therefore, IF7-conjugated drug captured by endothelial cells at the luminal surface can be released to the stroma where cancer cells could be exposed to drug at high concentration. During these processes, the peptide moiety of the anti-cancer drug conjugate would likely be digested by proteases allowing drug to penetrate tumor cells. This hypothesis is consistent with histological observations showing that cancer cells located around the vasculature underwent apoptosis in tumor-bearing mice injected with the IF7-conjugated apoptosis-inducing drug IF7-GA (FIG. 6B). Free SN-38 can be produced through the action of serum or tissue esterases. This allows SN-38 to enter cells and have its effect.

An IF7-conjugated anti-cancer drug improves chemotherapy efficacy through binding of IF7 to Anxa1 (FIG. 1F-H) and by expression of Anxa1 on tumor vasculature (FIG. 1F, 5A-C) (P. Oh et al. Subtractive proteomic mapping of the endothelial surface in lung and solid tumours for tissue-specific therapy. Nature 429:629-635 (2004)). These features lead to extremely high specificity and efficacy in delivering an IF7-conjugated compound to the tumor (FIG. 5). Given that it may take at least 15-30 minutes for an antibody to bind its antigen, the efficacy of IF7 binding to the tumor vasculature exceeds the levels of any tumor-targeting reagent known so far. Since it is a 7-mer peptide, production and quality control of IF7 is much easier than that used to produce humanized monoclonal antibodies for clinical trials (S. Izumoto et al. Phase II clinical trial of Wilms tumor 1 peptide vaccination for patients with recurrent glioblastoma multiforme. J Neurosurg 108:963-971 (2008)). Furthermore, peptides are readily degradable, and therefore concerns regarding human and environmental toxicity should be minimal. A short 7-mer peptide such as IF7 likely does not function as an antigen, and therefore concerns regarding immune reactions in patients injected by IF7 should be minimal.

In general, peptide-based drugs have been considered unstable as they are susceptible to proteases in vivo (L. Otvos, Jr. Peptide-based drug design: here and now. Methods Mol Biol 494:1-8 (2008), L. A. Landon et al. Is phage display technology on target for developing peptide-based cancer drugs? Curr Drug Discov Technol 1:113-132 (2004)). However, the extremely high tumor vasculature-targeting achieved by IF7 can overcome potential problems caused by proteolysis: IF7 functions as a vehicle for anti-cancer drug, and most IF7-conjugated drug can be delivered before IF7 undergoes proteolysis. Short peptides have been tested successfully for tumor vasculature targeting in vivo in the mouse (W. Arap et al. Cancer treatment by targeted drug delivery to tumor vasculature in a mouse model. Science 279:377-380 (1998); E. A. Murphy et al. Nanoparticle-mediated drug delivery to tumor vasculature suppresses metastasis. Proc Natl Acad Sci USA 105:9343-9348 (2008); N. Oku et al. Anti-neovascular therapy using novel peptides homing to angiogenic vessels. Oncogene 21:2662-2669 (2002); F. Donate et al. Pharmacology of the novel antiangiogenic peptide ATN-161 (Ac-PHSCN-NH2): observation of a U-shaped dose-response curve in several preclinical models of angiogenesis and tumor growth. Clin Cancer Res 14:2137-2144 (2008)). However, clinical trials have not yet yielded promising outcomes. IF7 can have advantages over previously known tumor vasculature-targeting peptides because it targets Anxa1, which was identified after rigorous comparisons of normal and tumor vasculature (P. Oh et al. Subtractive proteomic mapping of the endothelial surface in lung and solid tumours for tissue-specific therapy. Nature 429:629-635 (2004)).

Successful targeting of drug delivery to the tumor vasculature has not been achieved in humans (Ruoslahti E. et al. Annu Rev Immunol 2000; 18:813-27; Neri, D. et al. Nat Rev Cancer 2005; 5:436-46; Bellone, M. et al. Trends Immunol 2008; 29:235-41). The carbohydrate mimicry peptide IF7 can serve as a vehicle for such delivery because IF7 targets Anxa1, which is specifically expressed on tumor vasculature (Oh et al. Nature 2004; 429:629-35). Peptide-based therapeutics are advantageous, as large quantities of short, highly purified peptides can be synthesized at low cost for clinical trials (Izumoto et al., J Neurosurg 2008; 108:963-71). Furthermore, peptides are readily degradable, concerns regarding human and environmental toxicity should be minimal. Although no peptide-based anti-cancer drugs have been established (Arap et al., Science 1998; 279:377-80; Murphy, E. et al., Proc Natl Acad Sci 2008; 105: 9343-8; Oku, N. et al., Oncogene 2002; 21:2662-9; Donate, F., et al., Clin Cancer Res 2008; 14:2137-44), clear anti-cancer activity by IF7-GA and IF7-SN38 indicates that the rapid delivery of IF7-conjugated drug overcomes potential problems of IF7 proteolytic degradation.

Effective chemotherapy should rescue patients with malignant tumors not only in early but in advanced stages, and further suppress recurrence of malignancy by eradicating cancer stem cells. Highly efficient targeted drug delivery by IF7 would allow multiple chemotherapies by different anti-cancer drugs each with a distinct activity. Nonetheless, the efficacy of IF7-conjugated anti-cancer drugs remains to be evaluated clinically in cancer patients.

4. Materials and Methods.

i. Materials.

Peptides were synthesized by GenScript (Piscataway, N.J.). Rabbit anti-annexin 1 antibody (H-65) was from Santa Cruz Biotechnologies (Santa Cruz, Calif.). Phage clones each displaying I-peptide and IF7 have been described (Fukuda, M. et al., Cancer Res 2000; 60:450-6).

ii. Use of Vertebrate Animals.

Mouse protocols were approved by Institutional Review Committees at Burnham Institute for Medical Research.

iii. In Vivo Phage Targeting.

Mouse melanoma B16F1 cells ($2 \times 10^5$ cells/100 μl PBS) were injected subcutaneously into the dorsal flank of C57BL/6 female mice (8-10 weeks old). Ten days later, 1-peptide displaying phage clones or each clone displaying I-peptide related sequence ($1 \times 10^5$ pfu) in 100 μl PBS was injected intravenously. In a separate set of experiments, rabbit anti-Anxa1 antibody (H-65, Santa Cruz) or rabbit IgG (20 g IgG) was injected 15 minutes prior to phage injection. The mouse was perfused with TBS containing 1 mM CaCl2 (TBSC), and tumor and lung tissue was isolated. Tissue homogenates (100 mg protein) were incubated with competent K91 bacteria, and plated on LB agar containing tetracycline (10 μg/ml) and Kanamycin (100 μg/ml). Colonies appearing on an agar plate after culturing at 37° C. for 20 hours were counted.

iv. Binding of IF7-A488 to IF7-His$_6$ Protein.

Full-length cDNA encoding Anxa1 was obtained from Invitrogen (Carlsbad, Calif.) and subcloned into pET29a vector (Novagen) to produce an IF7-His$_6$ fusion protein. Recombinant proteins were purified by Ni$^+$ affinity chromatography. Wells of a black 384-well plate (Greiner bio-one) were coated with recombinant IF7-His$_6$ protein (10 μg/well). IF7-A488 (4 μg/ml) dissolved in 10 mM Tris-HCl buffer, pH7.4, containing 1 mM CaCl2 and 0.05% Tween 20, was added. After washing the plate, fluorescence was measured by a Molecular Devices Analyst HT plate reader. Analysis of inhibition of binding of Lewis A oligosaccharide to Anxa1-His$_6$ by IF7 and control RQ7 peptide was carried out using FITC-conjugated polyacrylamide-LeA (Glycotech) as described above.

v. In Vivo Imaging of IF7-A488 in Dorsal Skinfold Chamber Window

A Lewis lung carcinoma (LLC) tumor was produced in a donor nude mouse by subcutaneous injection, and small piece of tumor (less than 1 mm$^3$) was transplanted to a dorsal skinfold chamber in a recipient nude mouse (8-10 weeks female Balb/c nude) as described (Lehr et al., Am J Pathol 1993; 143:1055-62; Oh et al., Nat Biotechnol 2007; 25:327-37). Three days later, the mouse was anesthetized by peritoneal injection of 1.25% 2,2,2-Tribromoethanol (25 1/g). IF7-A488 or RQ7-A488 (100 μl; 50 mM in 5% glucose solution) was injected through the tail vein. Intravital Alexa 488 signals in the tumor were detected and recorded by a Zeiss Axioplan fluorescence microscope and a digital camera system (DP70 and DP controller, Olympus). For inhibition assays, rabbit anti-Anxa1 antibody (H-65, Santa Cruz) or rabbit IgG (20 μg IgG) was injected 15 minutes prior to IF7-A488 injection. Signal intensity in the tumor from 0 min to 40 min was measured by Image J (NIH, Maryland). After 10 min, irradiation of specimens by a UV lamp was limited only to times when photos were taken to avoid fluorescence bleaching. The tumor was isolated from the dorsal skin folder chamber, fixed with 4% paraformaldehyde at room temperature for 15 min, immersed in O.C.T compound, and cryosections were made. Frozen sections were overlaid with Vectashield containing DAPI (Vector laboratories) and examined under a Zeiss Axioplan fluorescence microscope.

vi. Tumor Models and IF7-GA or IF7-SN38 Treatment.

Mouse melanoma B16F1 cells ($2\times10^5$ cells/100 µl serum-free DMEM) were injected subcutaneously into the dorsal flank of C57BL/6 female mice (8-10 weeks old). Ten days later, mice were divided randomly into 4 groups, which received (1) 100 µl 5% glucose or the same amount of 5% glucose containing (2) IF7, (3) GA or (4) IF7-GA at 1.3 mM each on days 10, 12, and 14. On day 15, mice were sacrificed and tumor weights determined. Mouse Lewis lung carcinoma (LLC) cells ($4\times10^5$ cells/100 µl serum-free DMEM) were injected subcutaneously into the dorsal flank of C57BL/6 female mice (8-10 weeks old). Seven days later, mice were divided randomly into 4 groups and received (1) 100 µl 5% glucose or 5% glucose containing (2) IF7, (3) GA or (4) IF7-GA at 1.3 mM on days 7, 9, and 11. On day 13, mice were sacrificed and tumor weights determined. For the prostate cancer model, SCID/C.B-17 male mice (6-8 weeks old) were anesthetized by peritoneal injection of 1.25% 2,2,2-Tribromoethanol. Human prostate cancer PC3 cells ($1\times10^6$ cells/20 µl serum-free DMEM) were injected orthotopically into the mouse prostate. On day 7, mice were divided into 4 groups and treated as above on days 7, 12, 17 and 22. On day 28, mice were sacrificed and prostate tumor weights determined. For the breast cancer model, SCID/C.B-17 female mice (8-10 weeks old) were injected with human breast cancer MDA-MB-231 cells ($1\times10^6$ cells in 50 µl of Hanks' Balanced Salt Solution) together with 50 µl of matrigel (Becton Dickinson, San Jose, Calif.) into mammary fat. Intravenous injection of IF7-GA and control reagents followed schedules described for the prostate cancer model.

Figure 9:
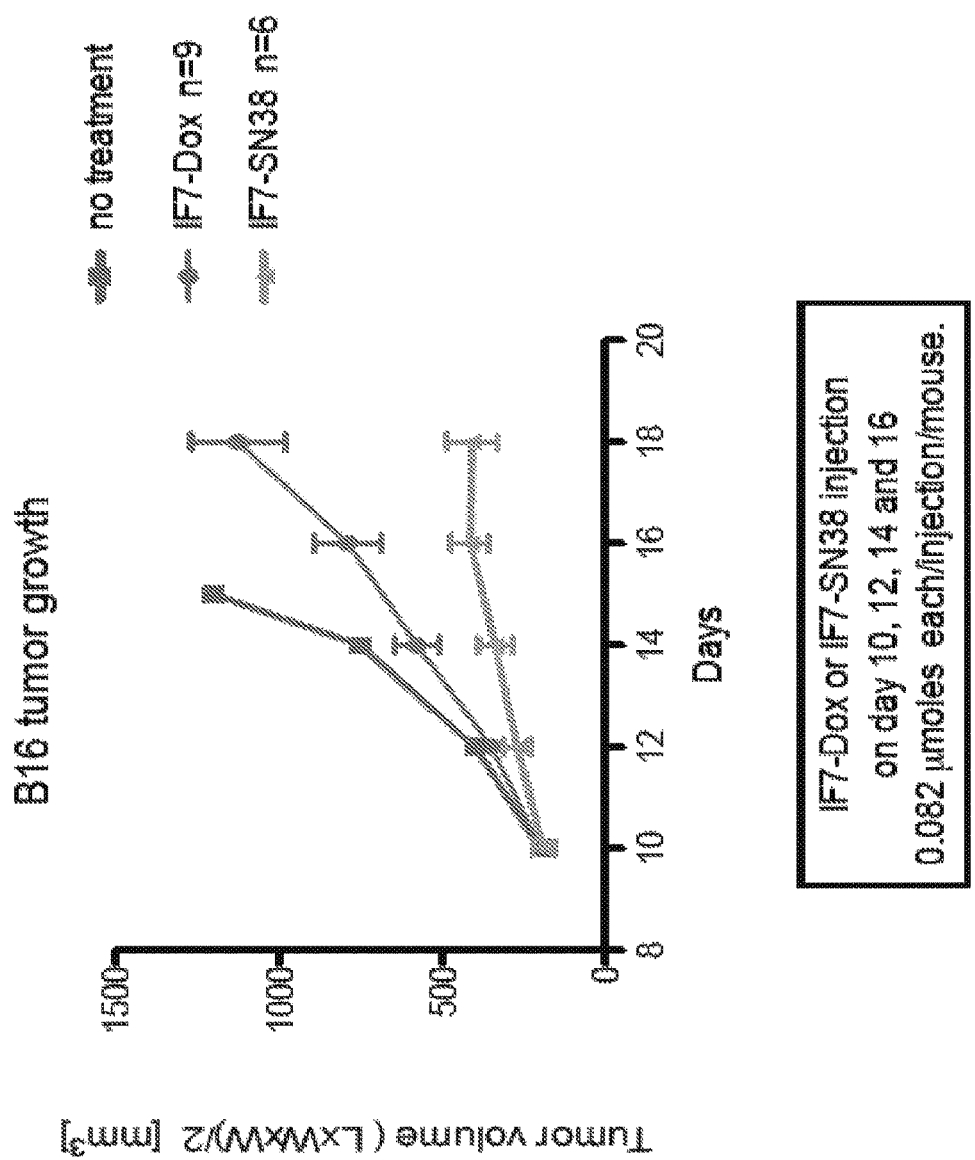
FIG. 9 is a graph of tumor volume (in mm$^3$) versus time (in days) for B16 solid tumors in mice. Treatment with IF7-Dox (doxorubicin), IF7-SN38, and a control (no treatment) are compared. While both drugs suppressed tumor growth, anti-tumor activity by IF7-SN38 was superior to IF7-Dox.

For the results shown in FIG. 9, mouse melanoma B16F1 cells ($2\times10^5$ cells/100 ul serum-free DMEM) were injected subcutaneously into the dorsal flank of C57BL/6 female mice (8-10 weeks old). Ten days later, mice were divided randomly into 3 groups, which received 100 µl 5% glucose containing 0.082 µmoles of IF7-Dox or IF7-SN38 each on days 10, 12, 14 and 16. Tumor sizes were measure using a caliper.

vii. Statistical Analysis.

Statistical analyses were performed using SPSS (Chicago, Ill.) and Microsoft Excel (Redmond, Wash.) programs. All values in figures and text are expressed as means±standard deviation (SD) of n observations, where n is the number of animals analyzed. Data sets were compared with Student's unpaired t-test (two tailed) or Mann-Whitney's U test. A p value≤0.05 was considered significant.

REFERENCES

1. Ruoslahti, E. Rajotte, D. An address system in the vasculature of normal tissues and tumors. Annu Rev Immunol 2000; 18: 813-27.
2. Neri, D. Bicknell, R. Tumour vascular targeting. Nat Rev Cancer 2005; 5: 436-46.
3. Bellone, M., Mondino, A. Corti, A. Vascular targeting, chemotherapy and active immunotherapy: teaming up to attack cancer. Trends Immunol 2008; 29: 235-41.
4. Hatakeyama, S., Sugihara, K., Nakayama, J., Akama, T. O., Wong, S. M., Kawashima, H., Zhang, J., Smith, D. F., Ohyama, C., Fukuda, M. Fukuda, M. N. Identification of mRNA splicing factors as the endothelial receptor for carbohydrate-dependent lung colonization of cancer cells. Proc Natl Acad Sci USA 2009; 106: 3095-100.
5. Oh, P., Li, Y., Yu, J., Durr, E., Krasinska, K. M., Carver, L. A., Testa, J. E. Schnitzer, J. E. Subtractive proteomic mapping of the endothelial surface in lung and solid tumours for tissue-specific therapy. Nature 2004; 429: 629-35.
6. Fukuda, M. N., Ohyama, C., Lowitz, K., Matsuo, O., Pasqualini, R., Ruoslahti, E. Fukuda, M. A peptide mimic of E-selectin ligand inhibits sialyl Lewis X-dependent lung colonization of tumor cells. Cancer Res 2000; 60: 450-6.
7. Zhang, J., Nakayama, J., Ohyama, C., Suzuki, M., Suzuki, A., Fukuda, M. Fukuda, M. N. Sialyl Lewis X-dependent lung colonization of B16 melanoma cells through a selectin-like endothelial receptor distinct from E- or P-selectin. Cancer Res 2002; 62: 4194-8.
8. Fukuda, M. N. Screening of peptide-displaying phage libraries to identify short peptides mimicking carbohydrates. Methods Enzymol 2006; 416: 51-60.
9. Hakomori, S. Glycosylation defining cancer malignancy: new wine in an old bottle. Proc Natl Acad Sci USA 2002; 99: 10231-3.
10. Nakamori, S., Kameyama, M., Imaoka, S., Furukawa, H., Ishikawa, O., Sasaki, Y., Kabuto, T., Iwanaga, T., Matsushita, Y. Irimura, T. Increased expression of sialyl Lewisx antigen correlates with poor survival in patients with colorectal carcinoma: clinicopathological and immunohistochemical study. Cancer Res 1993; 53: 3632-7.
11. Taki, T., Ishikawa, D., Ogino, K., Tanaka, M., Oku, N., Asai, T., Popa, I. Portoukalian, J. A new approach for drug discovery from glycobiology and phage-displayed peptide library technology. Biochim Biophys Acta 2008; 1780: 497-503.
12. Scott, J. K., Loganathan, D., Easley, R. B., Gong, X. Goldstein, I. J. A family of concanavalin A-binding peptides from a hexapeptide epitope library. Proc Natl Acad Sci USA 1992; 89: 5398-402.
13. Lehr, H. A., Leunig, M., Menger, M. D., Nolte, D. Messmer, K. Dorsal skinfold chamber technique for intravital microscopy in nude mice. Am J Pathol 1993; 143: 1055-62.
14. Vasilevskaya, I. A., Rakitina, T. V. O'Dwyer, P. J. Geldanamycin and its 17-allylamino-17-demethoxy analogue antagonize the action of Cisplatin in human colon adenocarcinoma cells: differential caspase activation as a basis for interaction. Cancer Res 2003; 63: 3241-6.
15. Mandler, R., Wu, C., Sausville, E. A., Roettinger, A. J., Newman, D. J., Ho, D. K., King, C. R., Yang, D., Lippman, M. E., Landolfi, N. F., Dadachova, E., Brechbiel, M. W. Waldmann, T. A. Immunoconjugates of geldanamycin and anti-HER2 monoclonal antibodies: antiproliferative activity on human breast carcinoma cell lines. J Natl Cancer Inst 2000; 92: 1573-81.
16. Eiseman, J. L., Lan, J., Lagattuta, T. F., Hamburger, D. R., Joseph, E., Covey, J. M. Egorin, M. J. Pharmacokinetics and pharmacodynamics of 17-demethoxy 17-[[(2-dimethylamino)ethyl]amino]geldanamycin (17DMAG, NSC 707545) in C.B-17 SCID mice bearing MDA-MB-231 human breast cancer xenografts. Cancer Chemother Pharmacol 2005; 55: 21-32.
17. Solit, D. B., Zheng, F. F., Drobnjak, M., Munster, P. N., Higgins, B., Verbel, D., Heller, G., Tong, W., Cordon-Cardo, C., Agus, D. B., Scher, H. I. Rosen, N. 17-Allylamino-17-demethoxygeldanamycin induces the degrada- 18. Mitsiades, C. S., Mitsiades, N. S., McMullan, C. J., Poulaki, V., Kung, A. L., Davies, F. E., Morgan, G., Akiyama, M., Shringarpure, R., Munshi, N. C., Richardson, P. G., Hideshima, T., Chauhan, D., Gu, X., Bailey, C., Joseph, M., Libermann, T. A., Rosen, N. S. Anderson, K. C. Antimyeloma activity of heat shock protein-90 inhibition. Blood 2006; 107: 1092-100.
19. Solit, D. B., Basso, A. D., Olshen, A. B., Scher, H. I. Rosen, N. Inhibition of heat shock protein 90 function down-regulates Akt kinase and sensitizes tumors to Taxol. Cancer Res 2003; 63: 2139-44.
20. Clarke, P. A., Hostein, I., Banerji, U., Stefano, F. D., Maloney, A., Walton, M., Judson, I. Workman, P. Gene expression profiling of human colon cancer cells following inhibition of signal transduction by 17-allylamino-17-demethoxygeldanamycin, an inhibitor of the hsp90 molecular chaperone. Oncogene 2000; 19: 4125-33.
21. Panaretou, B., Siligardi, G., Meyer, P., Maloney, A., Sullivan, J. K., Singh, S., Millson, S. H., Clarke, P. A., Naaby-Hansen, S., Stein, R., Cramer, R., Mollapour, M., Workman, P., Piper, P. W., Pearl, L. H. Prodromou, C. Activation of the ATPase activity of hsp90 by the stress-regulated cochaperone aha1. Mol Cell 2002; 10: 1307-18.
22. Meyer-Losic, F., Nicolazzi, C., Quinonero, J., Ribes, F., Michel, M., Dubois, V., de Coupade, C., Boukaissi, M., Chene, A. S., Tranchant, I., Arranz, V., Zoubaa, I., Fruchart, J. S., Ravel, D. Kearsey, J. DTS-108, A Novel Peptidic Prodrug of SN38: In vivo Efficacy and Toxicokinetic Studies. Clin Cancer Res 2008; 14: 2145-53.
23. Schnitzer, J. E., Liu, J. Oh, P. Endothelial caveolae have the molecular transport machinery for vesicle budding, docking, and fusion including VAMP, NSF, SNAP, annexins, and GTPases. J Biol Chem 1995; 270: 14399-404.
24. Schnitzer, J. E. Caveolae: from basic trafficking mechanisms to targeting transcytosis for tissue-specific drug and gene delivery in vivo. Adv Drug Deliv Rev 2001; 49: 265-80.
25. Izumoto, S., Tsuboi, A., Oka, Y., Suzuki, T., Hashiba, T., Kagawa, N., Hashimoto, N., Maruno, M., Elisseeva, O. A., Shirakata, T., Kawakami, M., Oji, Y., Nishida, S., Ohno, S., Kawase, I., Hatazawa, J., Nakatsuka, S., Aozasa, K., Morita, S., Sakamoto, J., Sugiyama, H. Yoshimine, T. Phase II clinical trial of Wilms tumor 1 peptide vaccination for patients with recurrent glioblastoma multiforme. J Neurosurg 2008; 108: 963-71.
26. Arap, W., Pasqualini, R. Ruoslahti, E. Cancer treatment by targeted drug delivery to tumor vasculature in a mouse model. Science 1998; 279: 377-80.
27. Murphy, E. A., Majeti, B. K., Barnes, L. A., Makale, M., Weis, S. M., Lutu-Fuga, K., Wrasidlo, W. Cheresh, D. A. Nanoparticle-mediated drug delivery to tumor vasculature suppresses metastasis. Proc Natl Acad Sci USA 2008; 105: 9343-8.
28. Oku, N., Asai, T., Watanabe, K., Kuromi, K., Nagatsuka, M., Kurohane, K, Kikkawa, H., Ogino, K., Tanaka, M., Ishikawa, D., Tsukada, H., Momose, M., Nakayama, J. Taki, T. Anti-neovascular therapy using novel peptides homing to angiogenic vessels. Oncogene 2002; 21: 2662-9.
29. Donate, F., Parry, G. C., Shaked, Y., Hensley, H., Guan, X., Beck, I., Tel-Tsur, Z., Plunkett, M. L., Manuia, M., Shaw, D. E., Kerbel, R. S. Mazar, A. P. Pharmacology of the novel antiangiogenic peptide ATN-161 (Ac-PHSCN-NH2): observation of a U-shaped dose-response curve in several preclinical models of angiogenesis and tumor growth. Clin Cancer Res 2008; 14: 2137-44.
30. Oh, P., Borgstrom, P., Witkiewicz, H., Li, Y., Borgstrom, B. J., Chrastina, A., Iwata, K., Zinn, K. R., Baldwin, R., Testa, J. E. Schnitzer, J. E. Live dynamic imaging of caveolae pumping targeted antibody rapidly and specifically across endothelium in the lung. Nat Biotechnol 2007; 25: 327-37.
31. del Rio, G., Castro-Obregon, S., Rao, R., Ellerby, H. M., and Bredesen, D. E. 2001. APAP, a sequence-pattern recognition approach identifies substance P as a potential apoptotic peptide. FEBS Lett 494:213-219.
32. Ellerby, H. M., Arap, W., Ellerby, L. M., Kain, R., Andrusiak, R., Rio, G. D., Krajewski, S., Lombardo, C. R., Rao, R., Ruoslahti, E., et al. 1999. Anti-cancer activity of targeted pro-apoptotic peptides. Nat Med 5:1032-1038.

The invention claimed is:

1. A composition comprising a linear peptide and a moiety, wherein the linear peptide comprises an amino acid sequence that can bind to a carbohydrate receptor on a cell, wherein:
   the amino acid sequence comprises IFLLWQRX (SEQ ID NO:25), IFLLWQRXX (SEQ ID NO:26), IFLLWQRXXX (SEQ ID NO:27), IFLLWQRXXXX (SEQ ID NO:20), or IFLLWQRXXXXX (SEQ ID NO:28), wherein the subsequence IFLLWQR (amino acids 1 to 7 of SEQ ID NO:28) in the amino acid sequence is an annexin-1 binding compound and has one or more conservative amino acid substitutions,
   wherein each X can independently be selected from all, any set of 8, any set of 7, any set of 6, any set of 5, any set of 4, any set of 3, any set of 2, or any 1 of the amino acids R, S, T, H, D, E, N and Q,
   wherein the linear peptide is a targeting peptide and wherein the moiety is selected from the group consisting of detectable agents and therapeutic agents.

2. The composition of claim 1, wherein the carbohydrate receptor is annexin 1.

3. The composition of claim 1, wherein the amino acid sequence can selectively bind the carbohydrate receptor.

4. The composition of claim 1, wherein the cell is a tumor cell.

5. The composition of claim 1, wherein each X is R.

6. The composition of claim 1, wherein the amino acid sequence consists of IFLLWQRX (amino acids 1 to 8 of SEQ ID NO:20), IFLLWQRXX (amino acids 1 to 9 of SEQ ID NO:20), IFLLWQRXXX (amino acids 1 to 10 of SEQ ID NO:20), IFLLWQRXXXX (amino acids 1 to 11 of SEQ ID NO:20), or IFLLWQRXXXXX (SEQ ID NO:20).

7. The composition of claim 1, wherein the peptide comprises at least 9 amino acids.

8. The composition of claim 1, wherein the moiety is covalently linked to the peptide.

9. The composition of claim 8, wherein the moiety is linked to the carboxy terminal end of the peptide.

10. The composition of claim 8, wherein the moiety is linked to an amino acid within the peptide.

11. The composition of claim 1, further comprising a linker connecting the moiety and the peptide.

12. The composition of claim 1, further comprising a pharmaceutically acceptable carrier.

13. The composition of claim 1, wherein the composition further comprises an anti-cancer agent.

* * * * *

UNITED STATES PATENT AND TRADEMARK OFFICE
CERTIFICATE OF CORRECTION

Page 1 of 1

PATENT NO. : 9,610,359 B2
APPLICATION NO. : 13/515930
DATED : April 4, 2017
INVENTOR(S) : Michiko Fukuda, Kazuhiro Sugihara and Naohira Kanayama It is certified that error appears in the above-identified patent and that said Letters Patent is hereby corrected as shown below:

In the Specification

In Column 1, Lines 15 through 20, please replace:
"This invention was made with government support under NIH grant P01CA071932 (MF and MNF), DoD Breast Cancer Research IDEA grant DAMD 17-02-1-0311 (MNF), and a Susan Komen Breast Cancer Research grant BCTR0504175 (MNF). The government has certain rights in this invention."
With:
"This invention was made with government support under P01 CA071932 awarded by the National Institutes of Health, and DAMD17-02-1-0311 awarded by the Army Research Laboratory - Army Research Office. The government has certain rights in the invention."

Signed and Sealed this
Tenth Day of December, 2024

Katherine Kelly Vidal
*Director of the United States Patent and Trademark Office*